US007166475B2

(12) United States Patent
Colyer et al.

(10) Patent No.: US 7,166,475 B2
(45) Date of Patent: Jan. 23, 2007

(54) COMPOSITIONS AND METHODS FOR MONITORING THE MODIFICATION STATE OF A PAIR OF POLYPEPTIDES

(75) Inventors: John Colyer, West Yorkshire (GB); Roger K. Craig, Cheshire (GB); Antonio Maschio, Winchester (GB); Mokdad Mezna, Leeds (GB)

(73) Assignee: Cyclacel Ltd., Dundee (GB)

( * ) Notice: Subject to any disclaimer, the term of this patent is extended or adjusted under 35 U.S.C. 154(b) by 0 days.

(21) Appl. No.: 09/259,658

(22) Filed: Feb. 26, 1999

(65) Prior Publication Data
US 2003/0032054 A1 Feb. 13, 2003

(51) Int. Cl.
*G01N 33/543* (2006.01)
*G01N 33/553* (2006.01)

(52) U.S. Cl. ............ 436/518; 436/165; 436/172; 436/525; 436/527; 356/317; 356/318; 422/57

(58) Field of Classification Search ............ 435/6, 435/69.1, 193, 320.1, 7.2, 15, 7.1, 4, 63, 435/64, 7.4, 21, 7.8, 254.21, 29, 7.9, 7.71, 435/7.72, 7.7, 194, 188; 530/350, 387.3; 536/235; 436/537, 544, 546
See application file for complete search history.

(56) References Cited

U.S. PATENT DOCUMENTS

| | | | | |
|---|---|---|---|---|
| 4,478,934 A | * | 10/1984 | Sato et al. ............... 435/7 |
| 5,082,786 A | | 1/1992 | Nakamoto |
| 5,185,248 A | * | 2/1993 | Barbacid et al. .......... 435/15 |
| 5,194,393 A | * | 3/1993 | Hugl et al. .............. 436/525 |
| 5,208,111 A | * | 5/1993 | Decher et al. ........... 428/420 |
| 5,215,887 A | | 6/1993 | Saito |
| 5,225,064 A | | 7/1993 | Henkens et al. |
| 5,316,754 A | * | 5/1994 | Vlassara et al. ........... 424/2 |
| 5,341,215 A | * | 8/1994 | Seher .................... 356/445 |
| 5,416,003 A | * | 5/1995 | Lawrence et al. ......... 435/18 |
| 5,439,797 A | * | 8/1995 | Tsien et al. ............ 435/7.21 |
| 5,478,755 A | * | 12/1995 | Attridge et al. .......... 436/518 |
| 5,484,735 A | * | 1/1996 | Davis et al. ............. 436/548 |
| 5,565,352 A | * | 10/1996 | Hochstrasser et al. ... 435/255.1 |
| 5,578,477 A | * | 11/1996 | Tamanoi ................ 435/193 |
| 5,582,995 A | * | 12/1996 | Avruch et al. ............ 435/71 |
| 5,605,152 A | | 2/1997 | Slate et al. |
| 5,631,169 A | * | 5/1997 | Lakowicz et al. ........ 436/537 |
| 5,637,463 A | * | 6/1997 | Dalton et al. ............. 435/6 |
| 5,682,884 A | | 11/1997 | Hill et al. |
| 5,710,009 A | * | 1/1998 | Fitzpatrick et al. ....... 435/7.9 |
| 5,736,337 A | * | 4/1998 | Avruch et al. .......... 435/7.1 |
| 5,744,313 A | * | 4/1998 | Williams et al. ........ 435/7.1 |
| 5,753,436 A | * | 5/1998 | Bronstein et al. .......... 435/6 |
| 5,755,953 A | | 5/1998 | Henning et al. |
| 5,763,571 A | * | 6/1998 | Avruch et al. ........... 530/324 |
| 5,767,075 A | * | 6/1998 | Avruch et al. ........... 514/12 |
| 5,773,592 A | * | 6/1998 | Mills .................... 534/573 |
| 5,776,717 A | * | 7/1998 | Cao ..................... 435/15 |
| 5,789,541 A | * | 8/1998 | Rando .................. 530/326 |
| 5,795,729 A | * | 8/1998 | Lee .................... 435/24 |
| 5,837,478 A | * | 11/1998 | Gallatin et al. .......... 435/7.24 |
| 5,837,822 A | * | 11/1998 | Gallatin et al. .......... 530/387.3 |
| 5,849,174 A | | 12/1998 | Sanghera et al. |
| 5,849,495 A | * | 12/1998 | Bronstein et al. .......... 435/6 |
| 5,851,791 A | * | 12/1998 | Vierstra et al. .......... 435/168.1 |
| 5,863,726 A | * | 1/1999 | Harley et al. ............ 435/6 |
| 5,880,268 A | * | 3/1999 | Gallatin et al. .......... 530/387.3 |
| 5,891,638 A | * | 4/1999 | Ibanez et al. ........... 435/6 |
| 5,932,421 A | * | 8/1999 | Ginsberg et al. ......... 435/6 |
| 5,948,620 A | * | 9/1999 | Hurd et al. ............. 435/6 |
| 5,962,289 A | * | 10/1999 | Kilburn et al. .......... 435/179 |
| 5,962,637 A | * | 10/1999 | Shone et al. ........... 530/329 |
| 5,965,699 A | * | 10/1999 | Schmidt et al. ......... 530/326 |
| 5,965,789 A | * | 10/1999 | Lubon et al. ........... 800/14 |
| 5,976,815 A | * | 11/1999 | Ibanez et al. ........... 435/7.2 |
| 5,977,303 A | * | 11/1999 | Aversa et al. .......... 530/350 |

(Continued)

FOREIGN PATENT DOCUMENTS

| | | |
|---|---|---|
| EP | 0392808 | 10/1990 |
| EP | 628819 | * 12/1994 |
| WO | 90/14431 | * 11/1990 |
| WO | WO95/34646 | 12/1995 |
| WO | WO96/20211 | 7/1996 |
| WO | WO96/21040 | 7/1996 |
| WO | WO96/35806 | 11/1996 |
| WO | WO97/28261 | 8/1997 |
| WO | WO97/44481 | 11/1997 |
| WO | WO9820024 | 5/1998 |
| WO | WO98/39471 | 9/1998 |
| WO | 9911774 | * 3/1999 |
| WO | WO99/11774 | 3/1999 |

OTHER PUBLICATIONS

Manne, V et al, Drug Development REsearch, vol. 34, 1995, pp. 121-137, Ras farnesylation as a target for novel antitumor agents:Potent and selective farnexyl diphosphate analog inhibitors of farnesyltransferase.*

SpA scintillation proximity assay, Cytostar-T scintillating microplate, Nov. 1997, Issue No. 35, Proximity News, Scintillation Proximity Assay (SPA) Bibliography, Amersham Life Science,pp. 1-8, listing of references for protein-protein interactions.*

(Continued)

*Primary Examiner*—Mark Navarro
*Assistant Examiner*—Ginny Allen Portner
(74) *Attorney, Agent, or Firm*—Elizabeth N. Spar; Kathleen M. Williams; Edwards Angell Palmer & Dodge

(57) ABSTRACT

This invention relates to a method for analyzing a sample comprising: immobilising a polypeptide to a physical support; contacting the immobilised polypeptide with a test sample which may contain an agent capable of modifying the immobilised polypeptide; contacting the immobilised polypeptide with a binding partner polypeptide, wherein the binding of this partner polypeptide to the immobilised polypeptide is at least partly dependent on the modification state of the immobilised polypeptide; and measuring the association of the binding partner polypeptide to the immobilised polypeptide.

4 Claims, No Drawings

U.S. PATENT DOCUMENTS

| | | | | | |
|---|---|---|---|---|---|
| 5,981,167 | A | * | 11/1999 | Taremi et al. | 435/4 |
| 5,981,200 | A | * | 11/1999 | Tsien et al. | 435/7.4 |
| 5,989,843 | A | * | 11/1999 | Gallatin et al. | 435/5 |
| 5,990,277 | A | * | 11/1999 | Levitzki et al. | 530/330 |
| 6,001,619 | A | * | 12/1999 | Beach et al. | 435/193 |
| 6,010,848 | A | * | 1/2000 | Delvecchio et al. | 435/5 |
| 6,037,136 | A | * | 3/2000 | Beach | 435/7.4 |
| 6,103,692 | A | * | 8/2000 | Avruch et al. | 514/12 |
| 6,110,691 | A | * | 8/2000 | Wang et al. | 435/7.1 |
| 6,117,641 | A | * | 9/2000 | Berlin et al. | 435/7.1 |
| 6,140,067 | A | * | 10/2000 | Anderson et al. | 435/26 |
| 6,146,842 | A | * | 11/2000 | Josiah et al. | 435/15 |
| 6,235,466 | B1 | * | 5/2001 | Branch et al. | 435/5 |
| 6,242,173 | B1 | * | 6/2001 | Mann et al. | 435/4 |
| 6,243,980 | B1 | * | 6/2001 | Bronstein et al. | 435/7.1 |
| 6,251,621 | B1 | * | 6/2001 | Lawrence et al. | 435/18 |
| 6,261,793 | B1 | * | 7/2001 | Whyte et al. | 435/15 |
| 6,268,123 | B1 | * | 7/2001 | Faff | 435/5 |
| 6,322,970 | B1 | * | 11/2001 | Little et al. | 435/6 |
| 6,410,255 | B1 | * | 6/2002 | Pollok et al. | 435/4 |
| 6,475,809 | B1 | * | 11/2002 | Wagner et al. | 436/518 |
| 6,569,833 | B1 | * | 5/2003 | Fahraeus et al. | 514/13 |
| 6,573,094 | B1 | * | 6/2003 | Harper et al. | 435/325 |
| 6,613,878 | B1 | * | 9/2003 | Cox et al. | 530/328 |
| 6,630,311 | B1 | * | 10/2003 | Epps et al. | 435/7.1 |
| 6,682,898 | B1 | * | 1/2004 | Wu et al. | 435/7.1 |
| 6,682,942 | B1 | * | 1/2004 | Wagner et al. | 436/518 |
| 6,714,875 | B1 | * | 3/2004 | Nash et al. | 702/23 |
| 6,808,874 | B1 | * | 10/2004 | Griffiths | 435/4 |
| 6,810,362 | B1 | * | 10/2004 | Adachi et al. | 702/187 |
| 2003/0104504 | A1 | * | 6/2003 | Colyer et al. | 435/7.92 |

OTHER PUBLICATIONS

Leftheris, K et al, J. Med. Chem, 1996, vol. 39, pp. 224-236, Developmnet of Highly Potent Inhibitors of Ras Farnesyltransferase Processing and in vivo activity.*

Kohl, Nancy E., Farnesyltransferase Inhibitors, Preclinical Development, pp. 91-102, Annals New York Academy of Sciences, 1999, vol. 886.*

Omer, CA et al, CaIA2X-competitive inhibitors of farnesyltransferase as anti-cancer agents, TIPS, Nov. 1997, vol. 18, pp. 437-445.*

Qian, Y et al, Farnesyltransferase as a target for anticancer drug design, Biopoly, vol. 43, pp. 25-41, 1997.*

Lebowitz, Peter F. et al, Molecular and Cellular Biology, Dec. 1995, vol. 15(12), pp. 6613-6622, Evidence that Farnesyltransferase inhibitors suppress RAs transformation by interfering with Rho activity.*

Avruch, J et al, The Endocrine Society, pp. 127-155, Recent progress in Hormone Research, vol. 56,Ras activation of the Raf kinase (abstract only).*

Adler, et al., in *Methods in Enzymology*, 27:675-796 (1973).
Atherton, et al., *J. Chem. Soc.*, 538-546 (1981).
Biou, et al., *Science*, 263:1404-1410 (1994).
Blenis and Erikson, *Proc. Natl. Acad Sci. USA*, 82:7621-7625 (1985).
Carrington, et al., *Journal of Virology*, 62:2313-2320 (1988).
Casey and Seabra, *J. Biol. Chem.*, 271:5289-5292 (1996).
Cesareni, er al., *Proc. Natl. Acad. Sci. USA*, 79:6313-6317 (1982).
Cox, *Methods Enzymol.*, 250:105-121 (1995).
Crick, *Acta. Cyrstallogr.*, 6:689-697 (1953).
Drago and Colyer, *J. Biol. Chem.*, 269:25073-25077 (1994).
Fushman, et al., *J. Biol. Chem.*, 273:2835-2843 (1998).
Gonzalez, et al., *Nature Structural Biol.*, 3:1011-1018 (1996).
Hahn, et al., *PNAS (USA)*, 89, 2679-2683 (1992).
Haltiwanger, et al., *J. Biol. Chem.*, 265:2563-2568 (1990).
Hanson and Schulman, *Ann. Rev. Biochem.*, 61:559 (1992).
Harbury, et al., *Nature*, 371:80-83 (1994).
Härtlein, er al., *Nucleic Acids Res.*, 15:1005-1017 (1987).
Hattori, et al., *Proc. Natl. Acad. Sci. USA*, 85:9148-9152 (1988).
Hayashi, et al., *J. Biol. Chem.*, 248:2296-2302 (1973).
Hicks, et al., *Folding and Design*, 2:149-158 (1997).
Hinnebusch, *Proc. Natl. Acad. Sci. USA*, 81:6442-6446 (1982).
Horiuchi, et al., *Mol. Cell. Biol.*, 12:4515 (1992).
Itoh, et al., *J. Biol. Chem.*, 268:3025 (1993).
Jovin and Jovin, *Cell Structure and Function by Microspectrofluorometry*, Kohen and Hirschberg, eds., Academic Press (1989).
Kemp and Pearson, *TIBS*, 15:342-346 (1990).
Klauck, et al., *Science*, 271:1589-1592 (1996).
Konishi, et al., *Biochem. Biophys. Res. Comm.*, 205:1770-1775 (1994).
Lakowicz, *Principles of Fluorescence Spectroscopy*, Plenum Press, NY (1983).
Larsson and Cerutti, *J. Biol. Chem.*, 263:17452-17458 (1988).
Lovejoy, et al., *Science*, 259:1288-1293 (1993).
Lumb and Kim, *Biochemistry*, 34:8642-8648 (1995).
Lumb, et al., *Biochemistry*, 33:7361-7367 (1994).
Matthias, et al., *Nucl. Acids Res.*, 17:6418 (1989).
Mátyus, *J. Photochem. Photobiol. B.:Bio.*, 12:323-337 (1992).
Merrifield, *J. Am. Chem. Soc.*, 85:2149-2154 (1963).
Miller, *Ann. Rev. Microbiol.*, 42:177-199 (1988).
Milligan, et al., *Trends in Biochemical Sciences*, 20:181-186 (1995).
Nautiyal, et al., *Biochemistry*, 34:11645-11651 (1995).
Nemenoff, et al., *Arch. Biochem. Biophys.*, 245:196-203 (1986).
Novak-Hofer and Thomas, *J. Biol. Chem.*, 259:5995-6000 (1984).
O'Shea, et al., *Science*, 243:538-542 (1989).
Palen & Traugh, *J. Biol. Chem.*, 262:3518-3523 (1987).
Parks, et al., *Analytical Biochemistry*, 216:413-417 (1994).
Pelech, et al., *Proc. Natl. Acad. Sci. USA*, 83:5968-5972 (1986).
Puls, et al., *Proc. Natl. Acad. Sci. USA*, 94:6191-6196 (1997).
Ron and Mochly-Rosen, *Proc. Natl. Acad. Sci. USA*, 92:492-496 (1995).
Sambrook, et al., *Molecular Cloning: A Laboratory Manual*, 2nd Ed., Cold Spring Harbor Laboratory Press, Cold Spring Harbor, NY (1989).
Schumacher, et al., *Science*, 271:1854-1857 (1996).
Shirataki, et al., *J. Biol. Chem.*, 266:20672-20677 (1991).
Spatola, in *Chemistry and Biochemistry of Amino Acids, Peptides and Proteins*, Winstein, ed., Marcel Dekker, NY, 267 (1983).
Stebbins, et al., *Nature*, 373:636-640 (1995).
Stone, et al., *J. Biol. Chem.*, 253:1137-1148 (1978).
Studier, et al., *Methods in Enzymol.*, 185:60-89 (1990).
Su, et al., *Biochemistry*, 33:15501-15510 (1994).
Thornberry and Lazbnik, "Caspases: enemies within", *Science*, 281:1312-1316 (1998).
Thornberry, et al., *J. Biol. Chem.*, 272:17907-17911.
Van Straaten, et al., *Proc. Natl. Acad. Sci. USA*, 80:3183-3187 (1983).
Vaughn, et al., *In Vitro*, 13:213-217 (1977).
Wang, et al., *J. Biol. Chem.*, 272:17542-17550 (1997).

* cited by examiner

SEQUENCE LISTING

<160> NUMBER OF SEQ ID NOS: 59

<210> SEQ ID NO 1
<211> LENGTH: 43
<212> TYPE: PRT
<213> ORGANISM: Artificial Sequence
<220> FEATURE:
<223> OTHER INFORMATION: Description of Artificial Sequence:Protein
      binding motif.

<400> SEQUENCE: 1

His His His His His His Gly Gly Ile Ala Gln Leu Glu Gln Glu Ile
 1               5                  10                  15

Ala Gln Leu Glu Gln Glu Asn Ala Gln Leu Glu Gln Glu Ile Ala Gln
            20                  25                  30

Leu Glu Gln Glu Ile Ala Lys Leu Glu Gln Glu
        35                  40

<210> SEQ ID NO 2
<211> LENGTH: 35
<212> TYPE: PRT
<213> ORGANISM: Artificial Sequence
<220> FEATURE:
<223> OTHER INFORMATION: Description of Artificial Sequence:Protein
      binding motif.

<400> SEQUENCE: 2

Ile Ala Gln Leu Lys Gln Lys Ile Ala Gln Leu Lys Gln Lys Asn Ala
 1               5                  10                  15

Gln Leu Lys Gln Lys Ile Ala Gln Leu Lys Gln Lys Ile Cys Gln Leu
            20                  25                  30

Lys Gln Lys
        35

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence:Protein
      binding motif.
<221> NAME/KEY: SITE
<222> LOCATION: (2)
<223> OTHER INFORMATION: Xaa at position 2 can be any amino acid.

-continued

```
<400> SEQUENCE: 3

Tyr Xaa Asp Glu Asp
 1               5

<210> SEQ ID NO 4
<211> LENGTH: 41
<212> TYPE: PRT
<213> ORGANISM: Homo sapiens

<400> SEQUENCE: 4

Ile Leu Ile Ser Leu Glu Ser Glu Glu Arg Gly Glu Leu Glu Arg Ile
 1               5                  10                  15

Leu Ala Asp Leu Glu Glu Glu Asn Arg Asn Leu Gln Ala Glu Tyr Asp
             20                  25                  30

Arg Leu Lys Gln Gln His Glu His Lys
         35                  40

<210> SEQ ID NO 5
<211> LENGTH: 32
<212> TYPE: PRT
<213> ORGANISM: Saccharomyces cerevisiae

<400> SEQUENCE: 5

Met Lys Gln Leu Glu Asp Lys Val Glu Glu Leu Leu Ser Lys Asn Tyr
 1               5                  10                  15

His Leu Glu Asn Glu Val Ala Arg Leu Lys Lys Leu Val Gly Glu Arg
             20                  25                  30

<210> SEQ ID NO 6
<211> LENGTH: 39
<212> TYPE: PRT
<213> ORGANISM: Homo sapiens

<400> SEQUENCE: 6

Thr Asp Thr Leu Gln Ala Glu Thr Asp Gln Leu Glu Asp Glu Lys Ser
 1               5                  10                  15

Ala Leu Gln Thr Glu Ile Ala Asn Leu Leu Lys Glu Lys Glu Lys Leu
             20                  25                  30

Glu Phe Ile Leu Ala Ala His
         35

<210> SEQ ID NO 7
<211> LENGTH: 39
<212> TYPE: PRT
<213> ORGANISM: Homo sapiens

<400> SEQUENCE: 7

Ile Ala Arg Leu Glu Glu Lys Val Lys Thr Leu Lys Ala Gln Asn Ser
 1               5                  10                  15

Glu Leu Ala Ser Thr Ala Asn Met Leu Arg Glu Gln Val Ala Gln Leu
             20                  25                  30

Lys Gln Lys Val Met Asn His
         35

<210> SEQ ID NO 8
<211> LENGTH: 38
<212> TYPE: PRT
<213> ORGANISM: Escherichia coli
```

```
<400> SEQUENCE: 8

Val Asp Lys Leu Gly Ala Leu Glu Glu Arg Arg Lys Val Leu Gln Val
 1               5                  10                  15

Lys Thr Glu Asn Leu Gln Ala Glu Arg Asn Ser Arg Ser Lys Ser Ile
            20                  25                  30

Gly Gln Ala Lys Ala Arg
            35

<210> SEQ ID NO 9
<211> LENGTH: 32
<212> TYPE: PRT
<213> ORGANISM: Escherichia coli

<400> SEQUENCE: 9

Glu Pro Leu Arg Leu Glu Val Asn Lys Leu Gly Glu Glu Leu Asp Ala
 1               5                  10                  15

Ala Lys Ala Glu Leu Asp Ala Leu Gln Ala Glu Ile Arg Asp Ile Ala
            20                  25                  30

<210> SEQ ID NO 10
<211> LENGTH: 33
<212> TYPE: PRT
<213> ORGANISM: Thermus thermophilus

<400> SEQUENCE: 10

Asp Leu Glu Ala Leu Leu Ala Leu Asp Arg Glu Val Gln Glu Leu Lys
 1               5                  10                  15

Lys Arg Leu Gln Glu Val Gln Thr Glu Arg Asn Gln Val Ala Lys Arg
            20                  25                  30

Val

<210> SEQ ID NO 11
<211> LENGTH: 32
<212> TYPE: PRT
<213> ORGANISM: Thermus thermophilus

<400> SEQUENCE: 11

Glu Ala Leu Ile Ala Arg Gly Lys Ala Leu Gly Glu Glu Ala Lys Arg
 1               5                  10                  15

Leu Glu Glu Ala Leu Arg Glu Lys Glu Ala Arg Leu Glu Ala Leu Leu
            20                  25                  30

<210> SEQ ID NO 12
<211> LENGTH: 30
<212> TYPE: PRT
<213> ORGANISM: Escherichia coli

<400> SEQUENCE: 12

Leu Arg Gly Ala Glu Lys Leu Arg Glu Glu Leu Asp Phe Leu Lys Ser
 1               5                  10                  15

Val Phe Arg Pro Glu Ile Ile Ala Ala Ile Ala Glu Ala Arg
            20                  25                  30

<210> SEQ ID NO 13
<211> LENGTH: 26
<212> TYPE: PRT
<213> ORGANISM: Escherichia coli
```

-continued

```
<400> SEQUENCE: 13

Ala Glu Tyr His Ala Ala Arg Glu Gln Gln Gly Phe Cys Gly Arg
 1               5                  10                  15

Ile Lys Asp Ile Glu Ala Lys Leu Ser Asn
             20                  25

<210> SEQ ID NO 14
<211> LENGTH: 32
<212> TYPE: PRT
<213> ORGANISM: Saccharomyces cerevisiae

<400> SEQUENCE: 14

Met Lys Gln Ile Glu Asp Lys Ile Glu Glu Ile Leu Ser Lys Ile Tyr
 1               5                  10                  15

His Ile Glu Asn Glu Ile Ala Arg Ile Lys Lys Leu Ile Gly Glu Arg
             20                  25                  30

<210> SEQ ID NO 15
<211> LENGTH: 29
<212> TYPE: PRT
<213> ORGANISM: Artificial Sequence
<220> FEATURE:
<223> OTHER INFORMATION: Description of Artificial Sequence:Synthetic
      peptide for coiled coil protein binding.

<400> SEQUENCE: 15

Glu Trp Glu Ala Leu Glu Lys Lys Leu Ala Ala Leu Glu Ser Lys Leu
 1               5                  10                  15

Gln Ala Leu Glu Lys Lys Leu Glu Ala Leu Glu His Gly
             20                  25

<210> SEQ ID NO 16
<211> LENGTH: 32
<212> TYPE: PRT
<213> ORGANISM: Saccharomyces cerevisiae

<400> SEQUENCE: 16

Met Lys Gln Ile Glu Asp Lys Leu Glu Glu Ile Leu Ser Lys Leu Tyr
 1               5                  10                  15

His Ile Glu Asn Glu Leu Ala Arg Ile Lys Lys Leu Leu Gly Glu Arg
             20                  25                  30

<210> SEQ ID NO 17
<211> LENGTH: 25
<212> TYPE: PRT
<213> ORGANISM: Escherichia coli

<400> SEQUENCE: 17

Gln Glu Lys Thr Ala Leu Asn Met Ala Arg Phe Ile Arg Ser Gln Thr
 1               5                  10                  15

Leu Thr Leu Leu Glu Lys Leu Asn Glu
             20                  25

<210> SEQ ID NO 18
<211> LENGTH: 24
<212> TYPE: PRT
<213> ORGANISM: Escherichia coli
```

-continued

```
<400> SEQUENCE: 18

Asp Glu Gln Ala Asp Ile Cys Glu Ser Leu His Asp His Ala Asp Glu
1               5                   10                  15

Leu Tyr Arg Ser Cys Leu Ala Arg
            20

<210> SEQ ID NO 19
<211> LENGTH: 16
<212> TYPE: PRT
<213> ORGANISM: Homo sapiens

<400> SEQUENCE: 19

Leu Ile Leu Ile Cys Leu Leu Leu Ile Cys Ile Ile Val Met Leu Leu
1               5                   10                  15

<210> SEQ ID NO 20
<211> LENGTH: 5
<212> TYPE: PRT
<213> ORGANISM: Artificial Sequence
<220> FEATURE:
<221> NAME/KEY: SITE
<222> LOCATION: (1)
<223> OTHER INFORMATION: Xaa at position 1 can be  W or L.
<221> NAME/KEY: SITE
<222> LOCATION: (5)
<223> OTHER INFORMATION: Xaa at position 5 can be any amino acid.
<223> OTHER INFORMATION: Description of Artificial Sequence:Caspase
      1,4,5 cleavage site.

<400> SEQUENCE: 20

Xaa Glu His Asp Xaa
1               5

<210> SEQ ID NO 21
<211> LENGTH: 5
<212> TYPE: PRT
<213> ORGANISM: Artificial Sequence
<220> FEATURE:
<221> NAME/KEY: SITE
<222> LOCATION: (3)
<223> OTHER INFORMATION: Xaa at position 3 can be any amino acid.
<221> NAME/KEY: SITE
<222> LOCATION: (5)
<223> OTHER INFORMATION: Xaa at position 5 can be any amino acid.
<223> OTHER INFORMATION: Description of Artificial Sequence:Caspase
      2,3,7 cleavage site.

<400> SEQUENCE: 21

Asp Glu Xaa Asp Xaa
1               5

<210> SEQ ID NO 22
<211> LENGTH: 5
<212> TYPE: PRT
<213> ORGANISM: Artificial Sequence
<220> FEATURE:
<221> NAME/KEY: SITE
<222> LOCATION: (1)
<223> OTHER INFORMATION: Xaa at position 1 can be L or V.
<221> NAME/KEY: SITE
<222> LOCATION: (3)
<223> OTHER INFORMATION: Xaa at position 3 can be any amino acid.
<221> NAME/KEY: SITE
<222> LOCATION: (5)
<223> OTHER INFORMATION: Xaa at position 5 can be any amino acid.
<223> OTHER INFORMATION: Description of Artificial Sequence:Caspase
      6,8,9 cleavage site.
```

```
<400> SEQUENCE: 22

Xaa Glu Xaa Asp Xaa
 1               5

<210> SEQ ID NO 23
<211> LENGTH: 5
<212> TYPE: PRT
<213> ORGANISM: Artificial Sequence
<220> FEATURE:
<221> NAME/KEY: SITE
<222> LOCATION: (5)
<223> OTHER INFORMATION: Xaa at position 5 can be any amino acid.
<223> OTHER INFORMATION: Description of Artificial Sequence:Factor Xa
      cleavage site.

<400> SEQUENCE: 23

Ile Glu Gly Arg Xaa
 1               5

<210> SEQ ID NO 24
<211> LENGTH: 7
<212> TYPE: PRT
<213> ORGANISM: Artificial Sequence
<220> FEATURE:
<221> NAME/KEY: SITE
<222> LOCATION: (3)
<223> OTHER INFORMATION: Xaa at position 3 can be any amino acid.
<221> NAME/KEY: SITE
<222> LOCATION: (5)
<223> OTHER INFORMATION: Xaa at position 5 can be any amino acid.
<221> NAME/KEY: SITE
<222> LOCATION: (7)
<223> OTHER INFORMATION: Xaa at position 7 can be S or G.
<223> OTHER INFORMATION: Description of Artificial Sequence:TEV protease
      cleavage site.

<400> SEQUENCE: 24

Glu Asn Xaa Tyr Xaa Gln Xaa
 1               5

<210> SEQ ID NO 25
<211> LENGTH: 43
<212> TYPE: PRT
<213> ORGANISM: Artificial Sequence
<220> FEATURE:
<223> OTHER INFORMATION: Description of Artificial Sequence:Synthetic
      peptide used to assay chymotrypsin activity.

<400> SEQUENCE: 25

His His His His His His Gly Gly Ile Ala Gln Leu Glu Gln Glu Ile
 1               5                  10                  15

Ala Gln Leu Glu Gln Glu Asn Ala Tyr Leu Glu Gln Glu Ile Ala Gln
            20                  25                  30

Leu Glu Gln Glu Ile Ala Lys Leu Glu Gln Glu
        35                  40

<210> SEQ ID NO 26
<211> LENGTH: 35
<212> TYPE: PRT
<213> ORGANISM: Artificial Sequence
<220> FEATURE:
<223> OTHER INFORMATION: Description of Artificial Sequence:Synthetic
      peptide used to assay chymotrypsin activity.
```

```
<400> SEQUENCE: 26

Ile Ala Gln Leu Lys Gln Lys Ile Ala Gln Leu Lys Gln Lys Asn Ala
 1               5                  10                  15

Gln Leu Lys Gln Lys Ile Ala Gln Leu Lys Gln Lys Ile Cys Gln Leu
            20                  25                  30

Lys Gln Lys
        35

<210> SEQ ID NO 27
<211> LENGTH: 43
<212> TYPE: PRT
<213> ORGANISM: Artificial Sequence
<220> FEATURE:
<223> OTHER INFORMATION: Description of Artificial Sequence:Synthetic
      peptide used to assay thrombin activity.

<400> SEQUENCE: 27

His His His His His His Gly Gly Ile Ala Gln Leu Glu Gln Glu Ile
 1               5                  10                  15

Ala Gln Leu Glu Gln Glu Asn Arg Gln Leu Glu Gln Glu Ile Ala Gln
            20                  25                  30

Leu Glu Gln Glu Ile Ala Lys Leu Glu Gln Glu
        35                  40

<210> SEQ ID NO 28
<211> LENGTH: 35
<212> TYPE: PRT
<213> ORGANISM: Artificial Sequence
<220> FEATURE:
<223> OTHER INFORMATION: Description of Artificial Sequence:Synthetic
      peptide used to assay thrombin activity.

<400> SEQUENCE: 28

Ile Ala Gln Leu Lys Gln Lys Ile Ala Gln Leu Lys Gln Lys Asn Ala
 1               5                  10                  15

Gln Leu Lys Gln Lys Ile Ala Gln Leu Lys Gln Lys Ile Cys Gln Leu
            20                  25                  30

Lys Gln Lys
        35

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence:TEV protease
      recognition site.
<221> NAME/KEY: SITE
<222> LOCATION: (2)
<223> OTHER INFORMATION: Xaa at position 2 can be any amino acid.
<221> NAME/KEY: SITE
<222> LOCATION: (3)
<223> OTHER INFORMATION: Xaa at position 3 can be any amino acid.
<221> NAME/KEY: SITE
<222> LOCATION: (5)
<223> OTHER INFORMATION: Xaa at position 5 can be any amino acid.

<400> SEQUENCE: 29

Glu Xaa Xaa Tyr Xaa Gln Ser
 1               5

<210> SEQ ID NO 30
<211> LENGTH: 43
<212> TYPE: PRT
<213> ORGANISM: Artificial Sequence
```

```
<220> FEATURE:
<223> OTHER INFORMATION: Description of Artificial Sequence:Synthetic
      peptide used to assay TEV protease.

<400> SEQUENCE: 30

His His His His His His Gly Gly Ile Ala Gln Leu Glu Gln Glu Ile
 1               5                  10                  15

Ala Gln Leu Glu Gln Glu Asn Ala Tyr Leu Gln Ser Glu Ile Ala Gln
            20                  25                  30

Leu Glu Gln Glu Ile Ala Lys Leu Glu Gln Glu
        35                  40

<210> SEQ ID NO 31
<211> LENGTH: 35
<212> TYPE: PRT
<213> ORGANISM: Artificial Sequence
<220> FEATURE:
<223> OTHER INFORMATION: Description of Artificial Sequence:Synthetic
      peptide used to assay TEV protease.

<400> SEQUENCE: 31

Ile Ala Gln Leu Lys Gln Lys Ile Ala Gln Leu Lys Gln Lys Asn Ala
 1               5                  10                  15

Gln Leu Lys Gln Lys Ile Ala Gln Leu Lys Gln Lys Ile Cys Gln Leu
            20                  25                  30

Lys Gln Lys
        35

<210> SEQ ID NO 32
<211> LENGTH: 7
<212> TYPE: PRT
<213> ORGANISM: Artificial Sequence
<220> FEATURE:
<221> NAME/KEY: SITE
<222> LOCATION: (3)
<223> OTHER INFORMATION: Xaa at position 3 can be any amino acid.
<221> NAME/KEY: SITE
<222> LOCATION: (6)
<223> OTHER INFORMATION: Xaa at position 6 can be any amino acid.
<223> OTHER INFORMATION: Description of Artificial Sequence:Protein
      kinase A modification site.

<400> SEQUENCE: 32

Arg Arg Xaa Arg Arg Xaa Ser
 1               5

<210> SEQ ID NO 33
<211> LENGTH: 5
<212> TYPE: PRT
<213> ORGANISM: Artificial Sequence
<220> FEATURE:
<221> NAME/KEY: SITE
<222> LOCATION: (2)
<223> OTHER INFORMATION: Xaa at position 2 can be any amino acid.
<221> NAME/KEY: SITE
<222> LOCATION: (3)
<223> OTHER INFORMATION: Xaa at position 3 can be any amino acid.
<221> NAME/KEY: SITE
<222> LOCATION: (5)
<223> OTHER INFORMATION: Xaa at position 5 can be any amino acid.
<223> OTHER INFORMATION: Description of Artificial Sequence:CaM kinase
      II modification site.
```

```
<400> SEQUENCE: 33

Arg Xaa Xaa Ser Xaa
 1               5

<210> SEQ ID NO 34
<211> LENGTH: 6
<212> TYPE: PRT
<213> ORGANISM: Artificial Sequence
<220> FEATURE:
<221> NAME/KEY: SITE
<222> LOCATION: (2)
<223> OTHER INFORMATION: Xaa at position 2 can be any amino acid.
<221> NAME/KEY: SITE
<222> LOCATION: (4)
<223> OTHER INFORMATION: Xaa at position 4 can be any amino acid.
<221> NAME/KEY: SITE
<222> LOCATION: (5)
<223> OTHER INFORMATION: Xaa at position 5 can be any amino acid.
<223> OTHER INFORMATION: Description of Artificial Sequence:S6 kinase
      modification site.

<400> SEQUENCE: 34

Arg Xaa Arg Xaa Xaa Ser
 1               5

<210> SEQ ID NO 35
<211> LENGTH: 36
<212> TYPE: PRT
<213> ORGANISM: Artificial Sequence
<220> FEATURE:
<223> OTHER INFORMATION: Description of Artificial Sequence:Peptide
      derived from GCN4 which contains a phosphorylation site.

<400> SEQUENCE: 35

Arg Met Lys Gln Leu Glu Asp Lys Val Glu Glu Leu Leu Ser Lys Thr
 1               5                  10                  15

Tyr His Leu Glu Asn Glu Val Ala Cys Leu Lys Lys Leu Val Gly Glu
                20                  25                  30

Arg Ala Ala Lys
            35

<210> SEQ ID NO 36
<211> LENGTH: 36
<212> TYPE: PRT
<213> ORGANISM: Artificial Sequence
<220> FEATURE:
<223> OTHER INFORMATION: Description of Artificial Sequence:Peptide
      derived from GCN4.

<400> SEQUENCE: 36

Arg Met Lys Gln Leu Glu Asp Gln Val Arg Arg Leu Arg Arg Lys Ser
 1               5                  10                  15

Tyr His Leu Glu Asn Glu Val Ala Cys Leu Lys Lys Leu Val Gly Glu
                20                  25                  30

Arg Ala Ala Lys
            35

<210> SEQ ID NO 37
<211> LENGTH: 36
<212> TYPE: PRT
<213> ORGANISM: Artificial Sequence
<220> FEATURE:
<223> OTHER INFORMATION: Description of Artificial Sequence:Peptide
      derived from GCN4.
```

-continued

```
<400> SEQUENCE: 37

Arg Met Lys Gln Leu Glu Asp Gln Val Arg Arg Leu Arg Arg Lys Thr
1               5                   10                  15

Tyr His Leu Glu Asn Glu Val Ala Cys Leu Lys Lys Leu Val Gly Glu
            20                  25                  30

Arg Ala Ala Lys
        35

<210> SEQ ID NO 38
<211> LENGTH: 43
<212> TYPE: PRT
<213> ORGANISM: Artificial Sequence
<220> FEATURE:
<223> OTHER INFORMATION: Description of Artificial Sequence:Synthetic
      coiled coil peptide that contains a phophorylation site.

<400> SEQUENCE: 38

His His His His His His Gly Gly Ile Ala Gln Leu Glu Gln Glu Ile
1               5                   10                  15

Arg Arg Leu Arg Arg Glu Ser Ala Gln Leu Glu Gln Glu Ile Ala Gln
            20                  25                  30

Leu Glu Gln Glu Ile Ala Lys Leu Glu Gln Glu
        35                  40

<210> SEQ ID NO 39
<211> LENGTH: 35
<212> TYPE: PRT
<213> ORGANISM: Artificial Sequence
<220> FEATURE:
<223> OTHER INFORMATION: Description of Artificial Sequence:Synthetic
      peptide used to form a coiled coil oligomer.

<400> SEQUENCE: 39

Ile Ala Gln Leu Lys Gln Glu Ile Ala Gln Leu Lys Gln Lys Asn Ala
1               5                   10                  15

Gln Leu Lys Gln Lys Ile Ala Gln Leu Lys Gln Lys Ile Cys Gln Leu
            20                  25                  30

Lys Gln Lys
        35

<210> SEQ ID NO 40
<211> LENGTH: 43
<212> TYPE: PRT
<213> ORGANISM: Artificial Sequence
<220> FEATURE:
<223> OTHER INFORMATION: Description of Artificial Sequence:Synthetic
      peptide used to assay CaMK-II activity.

<400> SEQUENCE: 40

His His His His His His Gly Gly Ile Ala Gln Leu Glu Gln Glu Ile
1               5                   10                  15

Ala Gln Leu Arg Gln Glu Ser Ala Gln Leu Glu Gln Glu Ile Ala Gln
            20                  25                  30

Leu Glu Gln Glu Ile Ala Lys Leu Glu Gln Glu
        35                  40

<210> SEQ ID NO 41
<211> LENGTH: 35
<212> TYPE: PRT
<213> ORGANISM: Artificial Sequence
<220> FEATURE:
<223> OTHER INFORMATION: Description of Artificial Sequence:Synthetic
      peptide used to assay CaMK-II activity.
```

```
<400> SEQUENCE: 41

Ile Ala Gln Leu Lys Gln Glu Ile Ala Gln Leu Lys Gln Lys Asn Ala
 1               5                  10                  15

Gln Leu Lys Gln Lys Ile Ala Gln Leu Lys Gln Lys Ile Cys Gln Leu
            20                  25                  30

Lys Gln Lys
        35

<210> SEQ ID NO 42
<211> LENGTH: 43
<212> TYPE: PRT
<213> ORGANISM: Artificial Sequence
<220> FEATURE:
<223> OTHER INFORMATION: Description of Artificial Sequence:Synthetic
      peptide used to assay S6 kinase activity.

<400> SEQUENCE: 42

His His His His His His Gly Gly Ile Ala Gln Leu Glu Gln Glu Ile
 1               5                  10                  15

Ala Arg Leu Arg Gln Glu Ser Ala Gln Leu Glu Gln Glu Ile Ala Gln
            20                  25                  30

Leu Glu Gln Glu Ile Ala Lys Leu Glu Gln Glu
        35                  40

<210> SEQ ID NO 43
<211> LENGTH: 35
<212> TYPE: PRT
<213> ORGANISM: Artificial Sequence
<220> FEATURE:
<223> OTHER INFORMATION: Description of Artificial Sequence:Synthetic
      peptide used to assay S6 kinase activity.

<400> SEQUENCE: 43

Ile Ala Gln Leu Lys Gln Glu Ile Ala Gln Leu Lys Gln Lys Asn Ala
 1               5                  10                  15

Gln Leu Lys Gln Lys Ile Ala Gln Leu Lys Gln Lys Ile Cys Gln Leu
            20                  25                  30

Lys Gln Lys
        35

<210> SEQ ID NO 44
<211> LENGTH: 11
<212> TYPE: PRT
<213> ORGANISM: Artificial Sequence
<220> FEATURE:
<223> OTHER INFORMATION: Description of Artificial Sequence:Synthetic
      peptide based upon p67srf glycosylation acceptor site.

<400> SEQUENCE: 44

Ser Ala Val Ser Ser Ala Asp Gly Thr Val Leu
 1               5                  10

<210> SEQ ID NO 45
<211> LENGTH: 43
<212> TYPE: PRT
<213> ORGANISM: Artificial Sequence
<220> FEATURE:
<223> OTHER INFORMATION: Description of Artificial Sequence:Synthetic
      peptide based upon p67srf glycosylation acceptor site.
```

```
<400> SEQUENCE: 45

His His His His His His Gly Gly Ile Ala Gln Leu Glu Gln Glu Ile
  1               5                  10                  15

Ala Gln Leu Ser Ala Val Ser Ser Ala Leu Gly Thr Val Leu Ala Gln
             20                  25                  30

Leu Glu Gln Glu Ile Ala Lys Leu Glu Gln Glu
         35                  40

<210> SEQ ID NO 46
<211> LENGTH: 35
<212> TYPE: PRT
<213> ORGANISM: Artificial Sequence
<220> FEATURE:
<223> OTHER INFORMATION: Description of Artificial Sequence:Synthetic
      peptide based upon p67srf glycosylation acceptor site.

<400> SEQUENCE: 46

Ile Ala Gln Leu Lys Gln Lys Ile Ala Gln Leu Lys Gln Lys Asn Ala
  1               5                  10                  15

Gln Leu Lys Gln Lys Ile Ala Gln Leu Lys Gln Lys Ile Cys Gln Leu
             20                  25                  30

Lys Gln Lys
         35

<210> SEQ ID NO 47
<211> LENGTH: 35
<212> TYPE: PRT
<213> ORGANISM: Artificial Sequence
<220> FEATURE:
<223> OTHER INFORMATION: Description of Artificial Sequence:Synthetic
      peptide used to assay chymotrypsin activity.

<400> SEQUENCE: 47

Ile Ala Gln Leu Lys Gln Lys Ile Ala Gln Leu Lys Gln Lys Asn Ala
  1               5                  10                  15

Gln Leu Lys Gln Lys Ile Ala Gln Leu Lys Gln Lys Ile Cys Gln Leu
             20                  25                  30

Lys Gln Lys
         35

<210> SEQ ID NO 48
<211> LENGTH: 43
<212> TYPE: PRT
<213> ORGANISM: Artificial Sequence
<220> FEATURE:
<223> OTHER INFORMATION: Description of Artificial Sequence:Synthetic
      peptide used to assay chymotrypsin activity.

<400> SEQUENCE: 48

His His His His His His Gly Gly Ile Ala Gln Leu Glu Gln Glu Ile
  1               5                  10                  15

Ala Gln Leu Glu Gln Glu Asn Ala Tyr Leu Glu Gln Glu Ile Ala Gln
             20                  25                  30

Leu Glu Gln Glu Ile Ala Lys Leu Glu Gln Glu
         35                  40

<210> SEQ ID NO 49
<211> LENGTH: 33
<212> TYPE: PRT
<213> ORGANISM: Artificial Sequence
<220> FEATURE:
<223> OTHER INFORMATION: Description of Artificial Sequence:Synthetic
      peptide used to assay carboxypeptidase activity.
```

```
<400> SEQUENCE: 49

His His His His His His Gly Gly Ile Ala Gln Leu Glu Gln Glu Ile
 1               5                  10                  15

Ala Gln Leu Glu Gln Glu Asn Ala Gln Leu Glu Gln Glu Ile Ala Gln
            20                  25                  30

Leu

<210> SEQ ID NO 50
<211> LENGTH: 33
<212> TYPE: PRT
<213> ORGANISM: Artificial Sequence
<220> FEATURE:
<223> OTHER INFORMATION: Description of Artificial Sequence:Synthetic
      peptide used to assay aminopeptidase activity.

<400> SEQUENCE: 50

Leu Glu Gln Glu Asn Ala Tyr Leu Glu Gln Glu Ile Ala Gln Leu Glu
 1               5                  10                  15

Gln Glu Ile Ala Lys Leu Glu Gln Glu Gly Gly His His His His His
            20                  25                  30

His

<210> SEQ ID NO 51
<211> LENGTH: 35
<212> TYPE: PRT
<213> ORGANISM: Artificial Sequence
<220> FEATURE:
<223> OTHER INFORMATION: Description of Artificial Sequence:Synthetic
      peptide used to assay exopeptidase activity.

<400> SEQUENCE: 51

Ile Ala Gln Leu Lys Gln Lys Ile Ala Gln Leu Lys Gln Lys Asn Ala
 1               5                  10                  15

Gln Leu Lys Gln Lys Ile Ala Gln Leu Lys Gln Lys Ile Cys Gln Leu
            20                  25                  30

Lys Gln Lys
        35

<210> SEQ ID NO 52
<211> LENGTH: 43
<212> TYPE: PRT
<213> ORGANISM: Artificial Sequence
<220> FEATURE:
<223> OTHER INFORMATION: Description of Artificial Sequence:Synthetic
      peptide used to assay TEV protease.

<400> SEQUENCE: 52

His His His His His His Gly Gly Ile Ala Gln Leu Glu Gln Glu Ile
 1               5                  10                  15

Ala Gln Leu Glu Gln Glu Asn Ala Tyr Leu Gln Ser Glu Ile Ala Gln
            20                  25                  30

Leu Glu Gln Glu Ile Ala Lys Leu Glu Gln Glu
        35                  40

<210> SEQ ID NO 53
<211> LENGTH: 35
<212> TYPE: PRT
<213> ORGANISM: Artificial Sequence
<220> FEATURE:
<223> OTHER INFORMATION: Description of Artificial Sequence:Synthetic
      peptide used to assay TEV protease.
```

```
<400> SEQUENCE: 53

Ile Ala Gln Leu Lys Gln Lys Ile Ala Gln Leu Lys Gln Lys Asn Ala
  1               5                  10                  15

Gln Leu Lys Gln Lys Ile Ala Gln Leu Lys Gln Lys Ile Cys Gln Leu
             20                  25                  30

Lys Gln Lys
         35

<210> SEQ ID NO 54
<211> LENGTH: 43
<212> TYPE: PRT
<213> ORGANISM: Artificial Sequence
<220> FEATURE:
<223> OTHER INFORMATION: Description of Artificial Sequence:Synthetic
      peptide used to assay thrombin activity.

<400> SEQUENCE: 54

His His His His His His Gly Gly Ile Ala Gln Leu Glu Gln Glu Ile
  1               5                  10                  15

Ala Gln Leu Glu Gln Glu Asn Arg Gln Leu Glu Gln Glu Ile Ala Gln
             20                  25                  30

Leu Glu Gln Glu Ile Ala Lys Leu Glu Gln Glu
         35                  40

<210> SEQ ID NO 55
<211> LENGTH: 35
<212> TYPE: PRT
<213> ORGANISM: Artificial Sequence
<220> FEATURE:
<223> OTHER INFORMATION: Description of Artificial Sequence:Synthetic
      peptide used to assay thrombin activity.

<400> SEQUENCE: 55

Ile Ala Gln Leu Lys Gln Lys Ile Ala Gln Leu Lys Gln Lys Asn Ala
  1               5                  10                  15

Gln Leu Lys Gln Lys Ile Ala Gln Leu Lys Gln Lys Ile Cys Gln Leu
             20                  25                  30

Lys Gln Lys
         35

<210> SEQ ID NO 56
<211> LENGTH: 43
<212> TYPE: PRT
<213> ORGANISM: Artificial Sequence
<220> FEATURE:
<223> OTHER INFORMATION: Description of Artificial Sequence:Synthetic
      peptide used to assay caspase activity.

<400> SEQUENCE: 56

His His His His His His Gly Gly Ile Ala Gln Leu Glu Gln Glu Ile
  1               5                  10                  15

Ala Gln Leu Glu Asp Glu Asn Asp Gln Leu Glu Gln Glu Ile Ala Gln
             20                  25                  30

Leu Glu Gln Glu Ile Ala Lys Leu Glu Gln Glu
         35                  40

<210> SEQ ID NO 57
<211> LENGTH: 35
<212> TYPE: PRT
<213> ORGANISM: Artificial Sequence
<220> FEATURE:
<223> OTHER INFORMATION: Description of Artificial Sequence:Synthetic
      peptide used to assay caspase activity.
```

```
<400> SEQUENCE: 57

Ile Ala Gln Leu Lys Gln Lys Ile Ala Gln Leu Lys Gln Lys Asn Ala
 1               5                  10                  15

Gln Leu Lys Gln Lys Ile Ala Gln Leu Lys Gln Lys Ile Cys Gln Leu
            20                  25                  30

Lys Gln Lys
        35

<210> SEQ ID NO 58
<211> LENGTH: 31
<212> TYPE: PRT
<213> ORGANISM: Artificial Sequence
<220> FEATURE:
<223> OTHER INFORMATION: Description of Artificial Sequence:Synthetic
      peptide used to assay geranylgeranyl transferase activity.

<400> SEQUENCE: 58

His His His His His His Gly Gly Ile Ala Gln Leu Glu Gln Glu Ile
 1               5                  10                  15

Ala Gln Leu Glu Gln Glu Asn Lys Gln Leu Glu Cys Ile Ala Leu
            20                  25                  30

<210> SEQ ID NO 59
<211> LENGTH: 23
<212> TYPE: PRT
<213> ORGANISM: Artificial Sequence
<220> FEATURE:
<223> OTHER INFORMATION: Description of Artificial Sequence:Synthetic
      peptide used to assay geranylgeranyl transferase activity.

<400> SEQUENCE: 59

Ile Ala Gln Leu Lys Gln Lys Ile Ala Gln Leu Lys Gln Lys Asn Ala
 1               5                  10                  15

Cys Leu Lys Gln Lys Ile Ala
            20
```

COMPOSITIONS AND METHODS FOR MONITORING THE MODIFICATION STATE OF A PAIR OF POLYPEPTIDES

FIELD OF THE INVENTION

The present invention relates to a method for detecting or monitoring biologically significant molecules.

BACKGROUND OF THE INVENTION

Post-translational modification of proteins has long been regarded as central to the regulation of cellular processes. Modification of proteins may affect their biological activity, or may affect their binding affinities for other cellular components, or may mark a protein for degradation, or have many other effect(s) on the protein. However, monitoring the post-translational modification state of proteins has been fraught with difficulties.

Even monitoring the abundance (for example the presence or absence) of a protein has been a laborious task, requiring extraction of proteins, followed by some kind of immuunoassay such as ELISA testing, Western-blotting, slot- or dot-blotting, immunoprecipitation or an enzyme assay for the activity of the protein. These methods are themselves time-consuming, and demand that the necessary reagents have already been prepared, such as antibodies which react with the protein of interest, or an assay which is able to read out the enzymatic activity of the polypeptide of interest. Even the preparation of these essential reagents requires significant investment of resources, and not all polypeptides have known enzymatic activities which can be readily assayed.

Monitoring the post-translational modification of various proteins has been accomplished in the past by extension of those techniques outlined above. For example, monitoring of ubiquitination of proteins has been carried out by extracting proteins from the sample to be tested, immunoprecipitating the protein of interest, Western blotting the immunoprecipitated protein, and then developing the Western blot using an anti-ubiquitin antibody. Clearly, this is a complicated procedure. In addition, there are many different isoforms of ubiquitin, and so repetition of the assay with antibodies against all the various forms of ubiquitin can increase the effort involved manifold.

Other types of modification which have in the past been monitored include phosphorylation. This may often be monitored in a manner analogous to the monitoring of ubiquitin, using phosphorylation-specific antibodies to immunoprecipitate and/or immunoblot only phosphorylated form(s) of the protein. However, the raising of phospho-specific antibodies is an expensive proposition, requiring careful screening of large numbers of different antisera. Moreover, the production of such reagents, even if attempted, is not always possible. For example, there is simply no reliable antibody available for the detection of phospho-serine or phospho-threonine. Currently, the only way of detecting these phosphorylation events is either to embark upon a programme to raise context-specific anti-phospho-antisera, which is not always feasible, or to use radioactive labelling techniques in conjunction with standard immunoprecipitation, assuming that immunoprecipitating antibodies are available to the protein which is to be tested. Clearly, it is simply not possible to use radioactive labelling when dealing with human patients.

Furthermore, parallel analysis of more than one of these parameters at a time is not possible. Each of the desired data must be tested individually, requiring larger samples of the starting material, and greater amounts of technicians' time. Building up a picture of the many variables which may be present in a disease state may require dozens of discrete tests, and concomitant expenditure of resources.

The present invention seeks to overcome such difficulties.

SUMMARY OF THE INVENTION

According to a first aspect of the present invention, there is provided a method for analysing a sample comprising the steps of:

a) providing a polypeptide pair comprising a first polypeptide and a second polypeptide capable of associating, wherein
  i) the association of the polypeptides is detectable, and
  ii) modification of at least one of the polypeptides results in modulation of the association;

b) immobilising the first polypeptide to a physical support;

c) contacting the immobilised polypeptide with the second polypeptide, and d) assaying for modification of at least one of the polypeptides by measuring the association of the second polypeptide to the first polypeptide.

As used herein, the term "sample" refers to a collection of inorganic, organic or biochemical molecules which is either found in nature (e.g., in a biological or other specimen) or in an artificially-constructed grouping, such as agents which might be found and/or mixed in a laboratory. Such a sample may be either heterogeneous or homogeneous. In particular, such a sample may contain one or more agents which are capable of modifying a polypeptide.

An immobilised polypeptide is one which is bound to a solid phase support. This binding may be covalent or via ionic bonding, hydrogen bonding, van-der-waals forces or any other non-covalent attachment, including antibody-antigen attachment, Ni-NTA attachment, avidin-biotin pairing and the use of GST tags. The solid phase may be a membrane, for example supported nitrocellulose, a bead, for example an agarose, glass or sepharose bead, a plastic substrate such as an ELISA dish or other plate, or may be a BIAcore chip or other silicon based chip. Preferably, the polypeptide is bound to the support in such a way that it is at least partly free in solution. Most preferably, the polypeptide ay be bound to the support via an N- or C-terminal linkage, for example via a C-terminal cysteine residue.

Modification of a polypeptide may include proteolysis (proteolytic cleavage), phosphorylation, dephosphorylation (phosphatase), acylation (for example fatty acylation such as farnesylation, geranylgeranylation, myristoylation, palmitoylation), glycosylation, ubiquitination, prenylation, sentrinisation, ADP-ribosylation, or the reversal of these processes where these are possible. Preferably, the immobilised polypeptide may be a substrate for one or more of these enzymatic activities. The term 'modification' as used herein may also include the binding of one or more molecules of the test sample to a polypeptide.

It will be apparent that, in accordance with the present invention, one of the polypetides is bound to a solid support. This polypeptide is referred to as the "immobilised polypeptide". Polypeptides capable of binding to, or bound to, the immobilised polypeptide are referred to as "binding partner" polypeptides.

The association between the immobilised polypeptide and the binding partner polypeptide may be measured by any suitable means. For example, a signal may be generated which may be dependent on the interaction of two polypeptides, one or both of which may be labelled. If the polypeptides interact, excitation of a fluorophore on one may result in Fluorescence Resonance Energy Transfer (FRET), and emission of light of a particular measurable wavelength from a fluorophore on the other.

The assay may be configured in such a way that modification of the immobilised polypeptide affects its capacity to bind the binding partner polypeptide. Therefore, by measuring the binding of the partner polypeptide, the modification state of the inmobilised polypeptide may be inferred.

Preferably, the assay is configured in such a way that biologically significant events are able to influence the signal.

If at least one of the first or second polypeptides is exposed to a sample containing one or more agent(s) which modifies the polypeptide(s), then this modification may be detected via its effect on the binding or association of the polypeptides.

The invention therefore provides a method according to the first aspect described above, further comprising the step of exposing at least one of the polypeptides to an agent capable of modifying the polypeptide(s).

As used herein, the term 'agent' is understood to mean a substance or group of substances which are capable, either singly or in combination, of bringing about modification of a polypeptide. Such an agent may be an enzymatic activity, or may be a chemical entity, or may be a mixture of one or more such entities.

Accordingly, the present invention provides a method for detecting and/or measuring post-translational modification of a substrate polypeptide by a sample.

In a further aspect, the invention provides a polypeptide pair comprising a first polypeptide immobilised to a support, and a second polypeptide bound to the first polypeptide, wherein:

a) at least one of the polypeptides is susceptible to modification, b) the binding of the polypeptides is detectable, and c) modification of at least one of the polypeptides results in modulation of the binding.

In a still further aspect, the invention provides a method for detecting or monitoring the activity of a modulator of a polypeptide modifying agent, comprising the steps of:

a) providing a first polypeptide, and a second polypeptide, wherein
   i) the first and second polypeptides are capable of binding to each other, and
   ii) modification of one or both of the polypeptides by the modifying agent results in modulation of the binding of the polypeptides to each other;

b) allowing the polypeptides to bind to each other, c) contacting the polypeptides with a modifying agent, d) detecting modulation of the binding of the polypeptides to determine a reference modulation of binding, e) contacting the polypetides with a modifying agent and a candidate modulator of the modifying agent, and f) detecting modulation of binding of the polypeptides, and comparing the modulation detected with the reference modulation.

The reference binding modulation is that degree of modulation, whether an increase or decrease in binding affinity or avidity, which is observed in the presence of a peptide modifying agent. The reference modulation need not be determined de novo for every analysis. It is sufficient for a reference modulation to be established such that the activity of potential modulators of peptide modifying agents can be assessed.

Modulators of peptide modifying agents may be any agents capable of upregulating or downregulating agents which themselves modify polypeptides. Thus, for example, a modulator may be an agent capable of potentiating or reducing the activity of a kinase or a phosphatase, a ubiquitin conjugating enzyme, a fatty acylation enzyme or other enzyme capable of modifying polypeptides.

The invention further provides support comprising one or more immobilised polypeptides, wherein at least one of the immobilised polypeptides is susceptible to modification, said modification being detectable by a method comprising:

a) contacting the itmobiliged polypeptide with a test sample which may contain an agent capable of modifying the immobilised polypeptide;

b) contacting the inunobilised polypeptide with a binding partner polypeptide, wherein the binding of this partner polypeptide to the immobilised polypeptide is at least partly dependent on the modification state of the immobilised polypeptide; and c) measuring the association of the binding partner polypeptide to the immobilised polypeptide.

Further features and advantages of the invention are in the following description and claims.

DESCRIPTION

According to the invention, binding of a first polypeptide to a second polypeptide is dependent upon modification, which modification may occur on one or more polypeptides.

As referred to herein, a polypeptide is susceptible to "modification" if it is capable of serving as a substrate for one or more modifying enzymes in accordance with the present invention. For example, the polypeptide may be susceptible to digestion by a specific protease enzyme, and preferably only susceptible to digestion by a specific protease enzyme. This facilitates the reduction of non-specific or background proteolysis and the use of the invention to assay specific proteolytic events. Alternatively, a polypeptide may be susceptible to phosphorylation by a specific kinase enzyme, and preferably only be susceptible to phosphorylation by a specific kinase enzyme. This facilitates the use of the invention to assay specific kinase activities. Furthermore, a polypeptide may also be susceptible to "modification" by entities other than enzymes. One or more chemical agent(s) may modify the polypeptide, either singly or in combination.

Advantageously, modification preferably occurs at a suitable site, which may be engineered into the one or more of the polypeptide(s)—an "engineered site"—or may be naturally present in one or more of the polypeptide(s)—a "natural site". However, it is also possible to design one or more polypeptide(s) such that they are potentially exposed to modification by an agent which initially recognises a site which may be distal to the polypeptide itself—such as on a further polypeptide bound to a polypeptide according to the invention.

The term "modification site" refers to an amino acid sequence which is recognised by (i.e., is a recognition site for) a modification enzyme. It is contemplated that a site comprises a small number of amino acids, typically from 2 to 10, less often up to 30 amino acids, and furer that a site comprises fewer than the total number of amino acids present in the polypeptide.

An engineered modification gite may be placed within a polypeptide of the invention at a position such that formation of an association between the isolated polypeptide and its binding partner is dependent upon the intactness of the site, Preferably, it does not overlap with an amino acid which is part of a label, to ensure that any detectable interaction is due to dissociation and not label loss.

It is contemplated that the position at which an engineered site is to reside may initially be determined by random placement of the site within the polypeptide, followed by testing by methods described herein of the ability of the polypeptide to associate with its intended binding partner(s), or not, depending upon the intactness or otherwise of the site. A pair of polypeptides, of which at least one comprises a site so placed that association of the polypeptides is dependent on cleavage at this site, is useful in the present invention.

Clearly, a polypeptide which is susceptible to "modification" may be subject to or may be the target of modification by any "modification enzymes" such as proteases, kinases, phosphatases, farnesyl transferases, ADP-ribosylating enzymes, glycosylating enzymes, prenylating enzymes, geranylgeranyl transferases, ubiquitinating enzymes, sentrinisation enzymes, fatty acylation enzymes, myristoylation enzymes, palmitoylation enzymes or any other polypeptide modifing enzyme.

Recognition or substrate sites for one or more of these enzymes may be engineered sites or natural sites as described above.

Examples of suitable substrate sites for these agents are well known to those skilled in the art, and examples of such sites are described below.

As used herein, the term "polypeptide" refers to a polymer in which the monomers are amino acids and are joined together through peptide or disulphide bonds. "Polypeptide" refers to an amino acid chain or a fragment thereof, such as a selected region of protein that is of interest in a binding interaction, or a synthetic amino acid chain, or a combination thereof. "Polypeptide" thus refers to an amino acid sequence between about 2 and about 500 amino acids in length, preferably about 4 to about 300, more preferably about 6 to about 200 amino acids, and even more preferably about 10 to about 50 or 100 amino acids in length, most preferably about 20 to about 30 amino acids in length. Additionally, amino acids other than naturally-occurring amino acids, for example β-alanine, phenyl glycine or homoarginine, may be included. Commonly-encountered amino acids which are not gene-encoded may also be used in the present invention. All of the amino acids used in the present invention may be either the D- or L-optical isomer. The D-isomers are preferred for use in a specific context, further described below. In addition, other peptidomimetics are also useful, e.g. in linker sequences of polypeptides of the present invention (see Spatola, 1983, in *Chemistry and Biochemistry of Amino Acids, Peptides and Proteins*, Weinstein, ed., Marcel Dekker, New York, p. 267).

"Naturally-occurring" as used herein, as applied to a polypeptide or polynucleotide, refers to the fact that the polypeptide or polynucleotide can be found in nature. One such example is a polypeptide or polynucleotide sequence that is present in an organism (including a virus) that can be isolated form a source in nature. Once the polypeptide is engineered as described herein it is no longer naturally occurring but is derived from a naturally occurring polypeptide.

"Polynucleotide" refers to a polymeric form of nucleotides of 2 up to 1,000 bases in length, or even more, either ribonucleotides or deoxyribonucleotideg or a modified form of either type of nucleotide. The term includes single and double stranded forms of DNA. The term is synonymous with "oligonucleotide".

As used herein, the term "associates" or "binds" refers to polypeptides as described herein having a binding constant sufficiently strong to allow detection of binding by a detection means, such as FRET or surface plasmon resonance. Preferably, the polypeptides, when associated or bound, are in physical contact with each other and have a dissociation constant (Kd) of about 10 µM or lower. The contact region may include all or parts of the two molecules. Therefore, the terms "substantially dissociated" or "dissociated" or "substantially unbound" or "unbound" refer to the absence or loss of contact between such regions, such that the binding constant is reduced by an amount which produces a discernible change in a signal compared to the bound state, including a total absence or loss of contact, such that the proteins are completely separated, as well as a partial absence or loss of contact, so that the body of the proteins are no longer in close proximity to each other but may still be tethered together or otherwise loosely attached, and thug have a dissociation constant greater than 10 μM (Kd). In many cases, the Kd will be in the mM range.

The term "complex", as used herein, refers to the polypeptides, peptides, proteins, domains or subunits in the associated or bound state. More than one molecule of each of the two or more polypeptides may be present in a complex, and molecules other than the two or more polypeptides may also be present in a complex, according to the methods of the invention. In all of these situations, the invention requires merely that the complex should be capable of moving between an associated and a dissociated state in response to modification of a component thereof.

As used herein the term "dissociation" refers to the ability of a polypeptide modifying agent, as defined above, to prevent or reverse the association of at least two polypeptides, as defined above, by at least 10%, preferably by 25–50%, highly preferably by 75–90% and, most preferably, by 95–100% relative to the association observed in the absence of modification under the same experimental conditions.

The association between the polypeptides may be measured for example by Fluorescent Resonance Energy Transfer (FRET), wherein the immobilised polypeptide harbours a fluorescent label moiety, and the binding partner polypeptide harbours a second such moiety, and where excitation at an appropriate wavelength may result in absorption of photons by one label, followed by FRET, and emission at a second wavelength characteristic of the second fluorophore, this emission being measured and corresponding to the amount of binding partner polypeptide which is associated with the immobilised polypeptide. Alternatively, this association may be measured in one of many other ways which are described more fully below.

The "detectable signal" or "measuring of association" referred to herein may be any detectable manifestation attributable to the presence of a label and will depend on the means selected for label detection. For example, in the event that the label is detected by FRET, a label will be present on at least two polypeptide components of the bound complex such that association and dissociation thereof can be monitored by measurement of energy transfer between the labels. However, if the label is detected for example by fluorescence correlation spectroscopy (FCS), which relies on the measurement of the rate of diffusion of a label, only a single labelled polypeptide is required. In the case of FCS detection, the labelled polypeptide is the binding partner polypeptide and is detectable in the free, unbound state as being mobile; when complexed to the immobilised polypeptide, it is immobile.

The "label" according to the invention preferably comprises a light emitting detection means, and the light emitting detection means advantageously emits light of at least a fluorescent wavelength emission. It is preferred that the light emitting detection means comprises two different fluorophores or fluorescent tags or groups.

A "fluorescent tag" or "fluorescent group" refers to either a fluorophore or a fluorescent protein or fluorescent fragment thereof, or refers to a fluorescent amino acid such as tryptophan which may be incorporated into a polypeptide. "Fluorescent protein" refers to any protein which fluoresces when excited with appropriate electromagnetic radiation. This includes proteins whose amino acid sequences are either natural or engineered.

It is additionally preferred that the fluorophores comprise fluorescein and tetramethylrhodamine or another suitable pair. In another preferred embodiment, the label comprises two different fluorescent proteins. It is preferred that fluorescent proteins comprise any protein selected from the group consisting of green fluorescent protein (GFP), blue fluorescent protein, red fluorescent protein and other engineered forms of GFP.

Preferably, the polypeptide comprises a cysteine amino acid through which the label is attached via a covalent bond. More preferably, the label may be attached via a primary anilne group such as via a lysine residue. As will be apparent to a person skilled in the art, it is preferable to avoid using the same chemistry for both labelling and immobilising polypeptides of the invention. For example, if the polypeptide is immobilised via cysteine residues, the label is advantageously attached via lysine residues.

Preferably, the measuring is performed by fluorescent resonance energy transfer (FRET), fluorescence anisotropy or fluorescence correlation spectroscopy, or by measuring the binding of a fluorescent partner polypeptide to an immobilised polypeptide.

It is preferred that the fluorescence emitting means comprise two different fluorophores, and particularly preferred that the fluorophores comprise fluorescein and tetramethylrhodamine or another suitable pair.

As used herein with regard to fluorescent labels for use in FRET, the term "appropriate combination" refers to a choice of reporter labels such that the emission wavelength spectrum of one (the "donor" moiety) is within the excitation wavelength spectrum of the other (the "acceptor" moiety).

The invention may be configured to exploit a number of non-fluorescent labels. In a first embodiment, the polypeptide multimer is an enzyme which is capable of participating in an enzyme-substrate reaction which has a detectable endpoint. The enzyme may be cleaved into two or more components, such that upon multimer formation the components reassemble to form a functional enzyme. Enzyme function may be assessed by a number of methods, including scintillation counting and photospectroscopy. In a further embodiment, the invention may be configured such that the label is a redox enzyme, for example glucose oxidase, and the signal generated by the label is an electrical signal.

Modification of one or more polypeptides according to the invention is required to inhibit multimer formation and enzyme component assembly, thus reducing enzyme activity.

In a second embodiment, an enzyme is used together with a modulator of enzyme activity, such as an inhibitor or a cofactor. Binding of the enzyme and its inhibitor or cofactor results in modulation of enzymatic activity, which is detectable by conventional means.

The invention also encompasses a pair of polypeptides, at least one of which is immobilised, which associate to form a complex, the pair comprising a first polypeptide comprising at least one binding domain, at least one site susceptible to modification, and a label, whereby the modification of at least one polypeptide is detectable via binding of the binding domain with a second polypeptide; and a second polypeptide which is capable of binding to the first polypeptide, wherein complex formation is detectable via the label.

The invention also provides an immobilised polypeptide complex, or a constituent polypeptide thereof, which is susceptible to post-translational modification such that modification leads to association or dissociation of the constituent polypeptides from the complex. The dissociation or association of the polypeptides in the complex is detectable (further described below). For example, the association of the complex is detectable through the interaction of labels placed on two or more polypeptides, this interaction changes depending on whether or not the polypeptides are associated or bound to one another. For example, where the labels are fluorescent labels, fluorescence resonance energy transfer (FRET) is observable when the labels are in close proximity in a complex. FRET is absent or otherwise modulated when the complex dissociates.

Methods of detection without use of label are known in the art. These include detection using surface plasmon resonance to detect changes in the mass of the immobilised polypeptide, which would occur if binding of the partner polypeptide increased or decreased. Such measurements may be made for example using a BIACORE machine.

The invention additionally provides a method of screening for a candidate modulator of enzymatic activity of a modification enzyme, the method comprising mixing in an appropriate buffer an appropriate amount of a polypeptide susceptible to modification, wherein the polypeptide binds to at least a second polypeptide, and wherein at least one polypeptide is suitably labelled with detection means for monitoring association/dissociation between the polypeptides; and a sample of material whose enzymatic activity is to be tested; and monitoring the modification of the polypeptide.

Modulation of the association of the polypeptides to form a complex is indicative of a modulation in the activity of the modification enzyme, and therefore of the activity of the candidate modification enzyme modulator.

"Modulation" refers to the capacity to either increase or decrease a measurable signal by at least 10%, 15%, 20%, 25%, 50%, 100% or more; such increase or decrease is dependent on modification of at least one polypeptide component of a complex.

As used herein, the interchangeable terms "biological specimen" and "biological sample" refer to a whole organism or a subset of its tissues, cells or component parts (e.g. body fluids, including but not limited to blood, mucus, lymphatic fluid, synovial fluid, cerebrospinal fluid, saliva, amniotic fluid, amniotic cord blood, urine, vaginal fluid and semen). "Biological sample" further refers to a homogenate, lysate or extract prepared from a whole organism or a subset of its tissues, cells or component parts, or a fraction or portion thereof. Lastly, "biological sample" may refer to a medium, such as a nutrient broth or gel in which an organism has been propagated, which contains cellular components, such as proteins or nucleic acid molecules.

As used herein, the term "organism" refers to all cellular life-forms, such as prokaryotes and eukaryotes, as well as non-cellular, nucleic acid-containing entities, such as bacteriophage and viruses.

It is highly preferred that a method of the methods described above comprises real-time observation of association of an isolated polypeptide and its binding partner or of an isolated pair of polypeptides.

As used herein in reference to monitoring, measurements or observations in assays of the invention, the term "real-time" refers to that which is performed contemporaneously with the monitored, measured or observed events and which yields a result of the monitoring, measurement or observation to one who performs it simultaneously, or effectively so, with the occurrence of a monitored, measured or observed event. Thus, a "real time" assay or measurement contains not only the measured and quantitated result, such as fluorescence, but expresses this in real time, that is, in hours, minutes, seconds, milliseconds, nanoseconds, picoseconds, etc. Shorter times exceed the instrumentation capability; further, resolution is also limited by the folding and binding kinetics of polypeptides.

As used herein, the term "contacting" refers to the act of placing two reagents in such a relationship that they may potentially interact in order to produce a chemical or biological effect. Preferably, the process of contacting involves admixing the reagents at an appropriate concentration in solution or suspension, either in liquid or solid phases, or both, in an appropriate buffer.

As used herein, the term "appropriate buffer" refers to a medium which permits activity of the modification enzyme used in an assay of the invention, such as a low-ionic-strength buffer or other biocompatible solution (e.g., water, containing one or more of physiological salt, such as simple saline, and/or a weak buffer, such as Tris or phosphate, or others as described hereinbelow), a cell culture medium, of which many are known in the art, or a whole or fractionated cell lysate; provided that it is compatible with the binding of the components of the assay of the invention, and with the selected signal employed. For example, the buffer advantageously does not include agents which quench fluorescence, if the signal is a fluorescent signal. An "appropriate buffer" permits digestion of polypeptides according to the invention and, preferably, inhibits degradation and maintains biological activity or the reaction components. Inhibitors of degradation, such as nuclease inhibitors (e.g., DEPC) are well known in the art. Lastly, an appropriate buffer may comprise a stabilising substance such as glycerol, sucrose or polyethylene glycol.

As used herein, the term "appropriate concentration" refers to an amount of reagent (for example, a labelled polypeptide of the invention) which is sufficient for the intended reaction to proceed in a detectable manner. For instance, in the case of a labelled polypeptide, an appropriate concentration may be considered to be that concentration at which the label emits a signal within the detection limits of a measuring device used in an assay of the invention. Such an amount is great enough to permit detection of a signal, yet small enough that a change in signal emission is detectable (e.g., such that a signal is below the upper limit of the device).

Therefore, the invention relates to a method for detecting or monitoring the activity of a modulator of a modification enzyme, comprising the steps of:

a) providing a first polypeptide, and a second polypeptide, wherein at least one of the polypeptides is immobilised on a solid support; and ii) the first and second polypeptides are capable of binding to each other in a detectable manner, and modification of one or both of the polypeptides by the modification enzyme results in modulation of the binding of the polypeptides to each other and therefore of the detectable signal;

b) allowing the polypeptides to bind to each other and induce a detectable signal;

c) contacting the polypeptides with a modification enzyme;

d) detecting modulation of the detectable signal as a result of the modulation of the binding of the polypeptides to determine a reference signal modulation;

e) contacting the polypeptides with a modification enzyme and a candidate modulator of the modification enzyme; and f) detecting modulation of the detectable signal as a result of the modulation of the binding of the polypeptides, and comparing the modulation detected with the reference signal modulation.

A "reference signal modulation" is the amount by which a detectable signal is modulated, as defined above, in response to the activity of a modification enzyme in accordance with the invention. For example, therefore, the signal may be modulated, that is increased or decreased, by 10%, 15%, 20%, 25%, 50%, 100% or more. The reference signal modulation may be calculated at any time, and used as a standard value; it need not be recalculated every time the assay is performed. Comparison of detected signal modulation values with the reference signal modulation preferably manifest themselves as increases or decreases in the percentage modulation with respect to the reference value.

The assay permits the assessment of the activity of compounds, whether naturally-occurring or synthesised, to modulate the activity of a modification enzyme. It thus permits the use of the invention to detect or monitor processes which rely on modification activity or result in or from modification activity, such as post-translational modifications of proteins. The invention preferably relates to a method for detecting or monitoring phosphorylation of a protein, comprising the foregoing steps.

The term "modulator" thus refers to a chemical compound (naturally occurring or synthesised), such as a biological macromolecule (e.g., nucleic acid, protein, non-peptide, or organic molecule), or an extract made from biological materials such as bacteria, plants, fungi, or animal (particularly mammalian) cells or tissues, or even an inorganic element or molecule. Modulators are evaluated for potential activity as inhibitors or activators (directly or indirectly) of a biological process or processes (e.g., agonist, partial antagonist, partial agonist, antagonist, antineoplastic agents, cytotoxic agents, inhibitors of neoplastic transformation or cell proliferation, cell proliferation-promoting agents, and the like) by inclusion in screening assays described herein. The activities (or activity) of a modulator may be known, unknown or partially-known. Such modulators can be screened using the methods described herein.

The term "candidate modulator" refers to a compound to be tested by one or more screening method(s) of the invention as a putative modulator. Usually, various predetermined concentrations are used for screening such as 0.01 μM, 0.1 μM, 1.0 μM, and 10.0 μM, as described more fully below. Test compound controls can include the measurement of a signal in the absence of the test compound or comparison to a compound known to modulate the target.

"Modulation" refers to the capacity to either increase or decease the activity of a modification enzyme by at least 10%, 15%, 20%, 25%, 50%, 100% or more; such increase or decrease may be contingent on the occurrence of a specific event, such as activation of a signal transduction pathway, and/or may be manifest only in particular cell types.

The range of modifications which can be accommodated within this basic assay are very great and include proteolysis, phosphorylation, dephosphorylation, glycosylation, acylation (including fatty acylation, farnesylation and geranylgeranylation), ubiquitination, prenylation, sentrinisation, or ADP-ribosylation (and the reversal of these reactions where possible).

In a still further aspect, the invention provides the use of an immobilised polypeptide complex according to the preceding aspects of the invention for the detection or monitoring of a protease activity.

Peptide or protein substrates peculiar to different enzymes can be immobilised to discrete areas of the same physical support, thereby providing a means of examining the activity of a number of enzymes from the same sample in parallel. Examples of suitable supports include miniature arrays of macromolecules, for example miniature arrays ('chips') bearing polypeptides or peptidomimetics.

To increase the specificity of the invention further, the protein substrate and binding partner can be made using D-amino acids with the exception of the residues which comprise the enzyme's interaction and/or modification site, these would be L-amino acids. Most enzymes will not recognise D-amino acid sequences as substrates and thus the likelihood of post-translational modification at unplanned sites is reduced. This refinement is likely to be applicable to assays of the invention.

The principle of the assay is illustrated for example in the following flowchart (Flowchart 1). Peptide (or protein) sequences, each containing at least a single modification site for a different enzyme are immobilised at discrete locations on a physical support. A binding partner sequence (or, if necessary, a range of binding partner sequences) is able to associate with these substrate peptides in a modification dependent manner. Association occurs with the unmodified form of the substrate peptide exclusively, but assays with the reverse characteristics can also be configured.

Exposure of the immobilised polypeptides to an enzyme solution results in the modification of one or more of said polypeptides. Modification of the polypeptide(s) reduces the association with the binding partner polypeptide. This change in association can be measured by any of a variety of techniques as described herein. By placing a range of substrate sequences on the physical support, a range of enzymatic activities or agents can be simultaneously assayed.

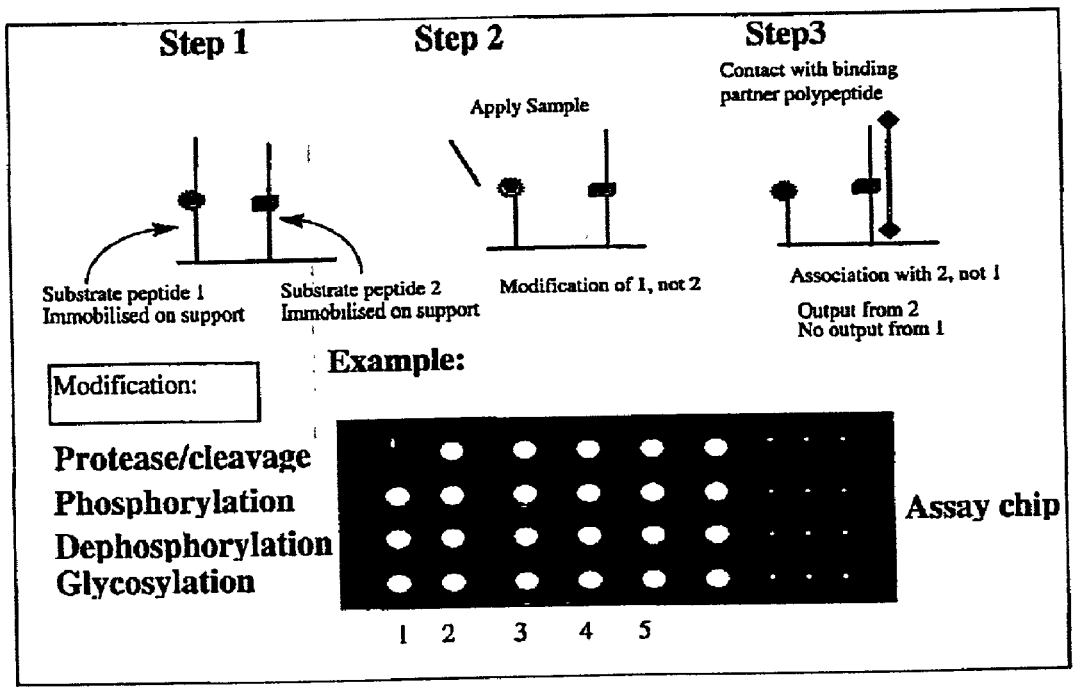
Flowchart 1

According to the invention, any two amino acid sequences capable of interacting with each other in a modification sensitive manner may be employed. The modification site may be natural, i.e. present in at least one of the partner sequences in nature; engineered into the sequence (created by alteration of a natural sequence); or engineered de novo into a wholly synthetic sequence (not known in nature). Binding of these partner structures should occur in one state of modification, but with less stability or not at all in the other.

For example, sequences of coiled-coil structure can be used in this invention.

```
template
                                            (SEQ ID NO. 1)
HHHHHHGGIAQLEQEIAQLEQENAQLEQEIAQLEQEIAKLEQE partner
                                            (SEQ ID NO. 2)
       IAQLKQKIAQLKQKNAQLKQKIAQLKQKICQLKQK
```

With the modification site(s) being on the template peptide, the amino acid sequence of the partner peptide may be varied in order to enhance the stability of binding to the template polypeptide.

Modes of Measurement

Association of binding partners may be measured by:

Mass: monitor increase in molecular mass of the hybrid species (e.g. use surface plasmon resonance)

Radioactivity: monitor radiolabelled binding partner (e.g. use phosphorimager or photosensitive emulsion) monitor either radiolabelled partner (e.g. use scintillation proximity assay)

Fluorescence: e.g., binding partner is labelled fluorescently: measure fluorescence directly e.g., use two different fluorophores, one on each of the polypeptides: measure FRET between two fluorescent polypeptides Immunology: e.g., use labelled antibody to the binding partner e.g., use labelled antibody to hapten on binding partner e.g., use labelled antibody to immobilised polypeptide (association of binding partner polypeptide masks antibody binding site on immobilised polypeptide)

Mobility: labelled binding partner becomes more immobile upon association: e.g., use fluorescence anisotropy and/or fluorescence correlation spectroscopy Enzymatic: reassociation of two parts of an enzyme Generally, the nomenclature used herein and the laboratory procedures in cell culture, molecular genetics, and nucleic acid chemistry and hybridisation described below are those well known and commonly employed in the art. Standard techniques are used for recombinant nucleic acid methods, polynucleotide synthesis, and microbial culture and transformation (e.g., electroporation, lipofection). Generally, enzymatic reactions and purification steps are performed according to the manufacturer's specifications. The techniques and procedures are generally performed according to conventional methods in the art and various general references (see generally, Sambrook et al., *Molecular Cloning A Laboratory Manual,* 2d ed. (1989) Cold Spring Harbor Laboratory Press, Cold Spring Harbor, N.Y., which is incorporated herein by reference) which are provided throughout this document. The nomenclature used herein and the laboratory procedures in analytical chemistry, organic synthetic chemistry, and pharmaceutical formulation described herein are those well known and commonly employed in the art. Standard techniques are used for chemical syntheses, chemical analyses, pharmaceutical formulation and delivery, and treatment of patients.

The present invention may be configured in a number of ways. Exemplary embodiments of the invention are set forth below.

Design and Construction of Polypeptides

Polypeptides useful in the present invention are capable of associating, either with similar or different polypeptides, to form a polypeptide complex in accordance with the invention. Such polypeptides may be naturally-occurring polypeptides, modified naturally-occurring polypeptides, or artificial polypeptides. Naturally-occurring polypeptides may be isolated from natural sources or, preferably, synthesised by peptide synthesis or produced using recombinant DNA expression technology. Synthetic or partially synthetic polypeptides may be synthesised by peptide synthesis or using recombinant DNA technology and, if necessary, nucleic acid synthesis techniques. Various techniques for the synthesis of nucleic acids and peptides are known in the art and may be applied to the present invention.

In a preferred embodiment, labelled polypeptides may be produced via the expression of recombinant nucleic acid molecules comprising an in-frame fussion of sequences encoding a desired polypeptide and a fluorescent protein moiety either in vitro (e.g., using a cell-free transcription/translation system, as described below, or instead using cultured cells transformed or transfected using methods well known in the art) or in vivo, for example in a transgenic animal including, but not limited to, insects, amphibians and mammals. A recombinant nucleic acid molecule of use in the invention may be constructed and expressed by molecular methods well known in the art, and may additionally comprise sequences including, but not limited to, those which encode a tag (e.g., a histidine tag) to enable easy purification, a secretion signal, a nuclear localisation signal or other primary sequence signal capable of targeting the construct to a particular cellular location, if it is so desired.

Assays may be configured such that a number of modifications can be monitored using unique, modified polypeptides peculiar to each assay and one common polypeptide, which is important in the automation of assays.

Moreover, where only one polypeptide is susceptible to a single modification, only one modification event is possible per complex. This situation can result in increased output of the assay, as effectively every modification event which takes place will have an affect on the readout.

The structural requirements for a polypeptide useful in the present invention may be defined as follows. Firstly, the polypeptide requires a binding site which will permit it to bind to other polypeptides to form a complex. Polypeptides are known to be able to associate in a number of ways, and domains which mediate polypeptide association are known in the art. For example, coiled coils, acid patches, zinc fingers, calcium hands, WD40 motifs, SH2/SH3 domains and leucine zippers are all polypeptide domains known to mediate protein-protein interactions, as are other domains known to those skilled in the art. Some examples of polypeptide interacting domains which may be suitable for use in this invention are presented in the following table:

TABLE 1

| Class | Subclass | Partner 1 | Example positions for engineered sites | Partner 2 | Possible positions for engineered sites |
|---|---|---|---|---|---|
| INTRA-MOLECULAR | | PKC pseudo-RACK site [a] | | PKC RACK binding site [a] | |
| | | Hemolin domains 1, 2 M63398 | | Hemolin domains 3, 4 M63398 | |
| HOMO-OLIGOMER | | PKA RIIb M31158 | 1–36 | PKA RIIb M31158 | 1–36 |
| | | MetJ monomer M12869 | 20–29, 52–66 | MetJ monomer M12869 | 20–29, 52–66 |
| | | Phospholamban M60411 | 18–31 | Phospholamban M60411 | 18–31 |
| HETERO-OLIGOMER | SH2 [§] | Src K03218 | 150–247 | RACK1 M24194 | |
| | | Src J00844 | 147–244 | AFAP110 L20303 | |
| | | RasGAP M23379 (human) | 181–272, 351–441 | EphB2 L25890 (mouse) AF025304 (human) | juxta-membrane region, including 604–613 (mouse) |
| | SH3 | ArgBP2 AF049884 | 436–484, 614–664 | Arg ** | pro rich region 2 |
| | | CRKL X59656 | 123–296 | Abl 1 X16416 | 782–1019 |
| | PDZ | nNOS U17327 | 1–195 | PSD 95 U83192 | 138–294 |
| | | PTP-BL Z32740 | 1352–1450, 1756–1855 | RIL Y08361 | 249–330 (LIM domain) |
| | PH | RAC protein kinase b_ M77198 | 1–108 | PKC z_ [¥] | 1–250 |
| | | bARK X61157 | 556–670 | Gbg_ [w] | WD40 repeats 5 and 6 |
| | PTB [f] | IRS 1 S62539 | 157–267 | IL4-R X52425 | 489–499 |
| | | Cbl X57110 | 1–357 | ZAP 70 L05148 | 284–299 |
| | WW | Nedd4 D42055 | 218–251, 375–408, 448–481, 500–533 | Amiloride-sensitive Na+ channel b subunit L36593 g subunit L36592 | C-terminal P2 region |
| | AKAP | AKAP 79 M90359 | 388–409 | PKA RIIb M31158 | 1–36 |
| | | AKAP 79 M90359 | 31–52 | PKC a, b1, b2 [z] | |
| | | AKAP 79 M90359 | 81–102 | Calcineurin (A subunit) M81483 | |
| | | Gravin U81607 | 1537–1563 | PKA RIIb M31158 | 1–45 |
| | | Gravin U81607 | 265–556 | PKC b2 [Å] | |
| | RACK | RACK1 M24194 | | PKCb1 X06318, M27545 | 186–198, 209–226 |
| | | b'COP X70476 | | PKCe X65293, S46030 | 2–145 |

TABLE 1-continued

| Class | Subclass | Partner 1 | Example positions for engineered sites | Partner 2 | Possible positions for engineered sites |
|---|---|---|---|---|---|
| | YXDED | ZIP⁻ Y08355 | 41–105 | PKC z | 79–145 | a Ron, D., Mochly-Rosen, D., Proceedings of the National Academy of Sciences, USA 1995, 92 492–496.
§ The SH2 domain is modified such that the addition or removal of a phosphate group from a tyrosine residue is no longer a determinant of binding. This is achieved by thiophosphorylation of the Tyr residue in an in vitro assay to yield a permanently phosphorylated protein. Alternatively, it is possible to mimic phosphorylation by the mutation of the key Tyr residue to Glu or Asp.
** Wang, B., Golemis, E. A., Kruh G. D., Journal of Biological Chemistry 1997, 272: 17542–17550
¥ Konishi, H., Kuroda, S., Kikkawa, U., Biochemical and Biophysical Research Communications 1994, 205 1770–1775. Fushman, D., Najmabadi-Haske, T., Cahill, S., Zheng, J., LeVine III, H., Cowburn, D., Journal of Biological Chemistry 1998, 273 2835–2843.
f Again, the PTB domain is modified such that the addition or removal of a phosphate group from a tyrosine residue is no longer a determinant of binding. This is achieved by thiophosphorylation of the Tyr residue in an in vitro assay to yield a permanently phosphorylated protein. Alternatively, it is possible to mimic phosphorylation by the mutation of the key Tyr residue to Glu or Asp.
z Klauck, T. M., Faux, M. C., Labudda, K., Langeberg, L. K., Jaken, S., Scott, J. D., Science 1996, 271 1589–92
Δ Nauert, J. B., Klauck, T. M., Langeberg, L. K., Scott, J. D., Current Biology 1997, 752–62
⁻ Puls, A., Schmidt, S., Grawe, F., Stabel, S., Proceedings of the National Academy of Sciences USA 1997, 94 6191–6196.

ZIP contains more than one protein binding motif (YXDED motif (SEQ ID NO. 3), ZZ zinc finger) and is known to bind to several proteins other than PKC z (including p62 and EBIAP) and also to self-associate (this self association is in competition with PKC z binding). These multiple interactions should be considered when designing an assay according to the present invention.

The coiled-coil domain is structurally conserved among many proteins that interact to form homo- or heterodimeric oligomers. The leucine zipper provides an example of one such protein structural motif. It is found in, among other examples, a nuclear protein that functions as a transcriptional activator of a family of genes involved in the General Control of Nitrogen (GCN4) metabolism in S. cerevisiae. The protein is able to dimerise and bind promoter sequences containing the recognition sequence for GCN4, thereby activating transcription in times of nitrogen deprivation.

Coiled-coils are a-helical oligomers or bundles with between 1 and 5 polypeptide strands with the following characteristics: (i) a sequence hallmark of a predominance of hydrophobic residues (in particular alanine, isoleucine, leucine, methionine or valine) spaced 3 and 4 residues apart in the primary sequence which is repeated three or more times in near or exact succession (canonical heptad coiled-coil repeat, abbreviated to $(3,4)_n$ where n=3 or greater). The hydrophobic residues are present at the 'a' and 'd' positions within a heptad when the amino acids are identified as positions a,b,c,d,e,f and g by order of sequence. In addition, spacing of hydrophobic residues in patterns of 3,4,4 and 3,4,3 (hendecad repeat) have recently been reported (Hicks et al., 1997, *Folding and Design*, 2: 149–158) and are compatible with the coiled-coil structure. (ii) In structural terms coiled-coil helical bundles have between 2 and 5 helices which are offset at roughly 20° to adjacent strands with the hydrophobic sidechains interdigitating in the interface between helices in what is termed the "knobs into holes" packing (Crick, 1953, *Acta. Crystallogr.*, 6: 689–697). Natural and non-natural coiled-coils can have parallel and/or antiparallel helices. Both homotypic (multiple strands of identical sequence) and heterotypic bundles have been described.

Leucine zipper sequences conform to the coiled-coil rules above and typically have leucine residues at the 'd' position of the canonical heptad repeat. These leucine residues represent a single face of the helix. Interdigitating with these leucine residues are other hydrophobic amino acids, frequently valine, isoleucine or leucine residues. The combination of these residues forms a continuous hydrophobic face which associates with an equivalent region in an associating subunit. Alternatively the hydrophobic face can be discontinuous due to interruptions in the heptad repeat sequence. This, however, does not interfere with the ability of these coiled-coils to interact. The stability of the dimer thus formed is conferred by the hydrophobic interactions between the leucine residues and the interdigitating hydrophobic residues. Hydrogen bonds that form between residues present on the two interacting helices, particularly at the e and g positions, also contribute to the stability of the dimer. The coiled-coil domain of GCN4 has been shown to dimerise as an isolated peptide (Gonzalez et al., 1996, *Nature Structural Biology*, 3: 1011–1018).

Examples of naturally-occurring coiled-coils are as follows:

Coiled-coil class and example:

fgabcdefgabcdefgabcdefgabcdefgabcdefgabcdeg

```
Parallel two-stranded
tropomyosin
TMPA_RABIT, 10-279 (270)
(J.BIOL.CHEM. 253, 1137-1148, 1978)

dystrophin
                                    (SEQ ID NO. 4)
ILISLESEERGELERILADLEEENRNLQAEYDRLKQQHEHK
SWISS PROT:P11532 (HUMAN)
(Trends Biol. Sci., 20,133-135, 1995)

GCN4*
                                    (SEQ ID NO. 5)
MKQLEDKVEELLSKNYHLENEVARLKKLVGER
GCN4_YEAST, 250-281 (32)
(Proc. Natl. Acad. Sci. U.S.A., 81, 6442-6446,
1982)

cFOS*
```

-continued (SEQ ID NO. 6)
TDTLQAETDQLEDEKSALQTEIANLLKEKEKLEFILAAH
FOS_HUMAN, 162–199 (39),
(Proc. Natl. Acad. Sci, U.S.A., 80: 3183–3187, 198)

cJUN*
(SEQ ID NO. 7)
IARLEEKVKTLKAQNSELASTANMLREQVAQLKQKVMNH
AP1_HUMAN, 277–315 (39)
(Proc. Natl. Acad. Sci. U.S.A., 85: 9148–9152, 1988

Seryl-tRNA synthetase, E.coli*
(SEQ ID NO. 8)
VDKLGALEERRKVLQVKTENLQAERNSRSKSIGQAKAR
SYS_ECOLI, 27–64 (38)

(SEQ ID NO. 9)
EPLRLEVNKLGEELDAAKAELDALQAEIRDIA
NUCLEIC ACIDS RES., 15, 1005–1017,1987
SYS_ECOLI, 69–100 (32)

Seryl-tRNA synthetase,
Thermus thermophilus*
(SEQ ID NO. 10)
DLEALLALDREVQELKKRLQEVQTERNQVAKRV
(SEQ ID NO. 11)
EALIARGKALGEEAKRLEEALREKEARLEALL
SYS_THERM, 26–58 (33)
(Science, 263: 1404–141
SYS_THERM, 67–98 (32)

Transcript cleavage factor GreA*
(SEQ ID NO. 12)
LRGAEKLREELDFLKSvFRPEIIAAIAEAR
GREA_ECOLI, 8–37 (30)

(SEQ ID NO. 13)
AEYHAAREQQGFCEGRIKDIEAKLSN
(Nature, 373: 636–640, 1995)
GREA_ECOLI, 46–71 (26)

Parallel three-stranded
GCN4 Zip mutant pII*
(SEQ ID NO. 14)
MKQIEDKIEEILSKIYHIENEIARIKKLIGER
GCN4 Zip mutant pII*
(Nature, 371: 80–83)

Antiparallel three-stranded
synthetic peptide coil-Ser*
(SEQ ID NO. 15)
EWEALEKKLAALESKLQALEKKLEALEHG
(Science, 259: 1288–1293)

Parallel four-stranded
GCN4 Zip mutant pLl*
(SEQ ID NO. 16)
MKQIEDKLEEILSKLYHIENELARIKKLLGER
(Nature, 371: 80–83)

Antiparallel four-stranded
Repressor of primer ROP*
(SEQ ID NO. 17)
QEKTALNMARFIRSQTLTLLEKLNE
ROP_ECOLI, 4–28 (25)

(SEQ ID NO. 18)
DEQADICESLHDHADELYRSCLAR
(Proc. Natl. Acad. Sci. U.S.A., 79: 6313–6317 1982)
ROP_ECOLI, 32–55 (24)

Parallel five-stranded
Phospholamban
(SEQ ID NO. 19)
LILICLLLICIIVMLL
PPLA_HUMAN, 37–52 (16)
(JBC 271, 5941–5946, 1996)

antiparallel two-stranded

The binding domains may be similar or different, i.e. homomultimeric or heteromultimeric. The rules for the design of hetero-multimeric coiled coils are well detailed in the literature (including Peptide 'Velcro': design of a heterodimeric coiled coil, O'Shea, E. K., Lumb, K. J. & Kim, P. S., Current Biology (1993) 3 658–667; A designed heterotrimeric coiled coil, Nautiyal, S., Woolfson, D. N., King, D. S. & Alber T., Biochemistry (1995) 34 11645–11651; A buried polar interaction imparts structural uniqueness in a designed heterodimeric coiled coil, Lumb, K. J. & Kim P. S., Biochemistry (1995) 34 8642–8648). The use of a 'designer' coiled coil has benefit in providing control over the potential modification sites present other than those inserted to monitor the reaction of interest.

Of course, polypeptides may also associate via interactions, not necessarily involving canonical domains such as coiled-coils, which may be specific to the polypeptides in question.

In a preferred embodiment, one or more polypeptides in each multimer may comprise a label. Suitable fluorescent labels include fluorophores and fluorescent proteins. As used herein, the terms "fluorophore" and "fluorochrome" refer interchangeably to a molecule which is capable of absorbing energy at a wavelength range and releasing energy at a wavelength range other than the absorbance range. The term "excitation wavelength" refers to the range of wavelengths at which a fluorophore absorbs energy. The term "emission wavelength" refers to the range of wavelength that the fluorophore releases energy or fluoresces.

A non-limiting list of chemical fluorophores of use in the invention, along with their excitation and emission wavelengths, is presented in Table 2.

TABLE 2

| Fluorophore | Excitation (nm) | Emission (nm) | Colour |
| --- | --- | --- | --- |
| PKH2 | 490 | 504 | green |
| PKH67 | 490 | 502 | green |
| Fluorescein (FITC) | 495 | 525 | green |
| Hoechst 33258 | 360 | 470 | blue |
| R-Phycoerythrin (PE) | 488 | 578 | orange-red |
| Rhodamine (TRITC) | 552 | 570 | red |
| Quantum RedÔ | 488 | 670 | red |
| PKH26 | 551 | 567 | red |
| Texas Red | 596 | 620 | red |
| Cy3 | 552 | 570 | red |

Examples of fluorescent proteins which vary among themselves in excitation and emission maxima are listed in Table 1 of WO 97/28261 (incorporated herein by reference). These (each followed by [excitation max./emission max.] wavelengths expressed in nanometers) include wild-type Green Fluorescent Protein [395(475)/508] and the cloned mutant of Green Fluorescent Protein variants P4 [383/447], P4-3 [381/445], W7[433(453)/475(501)], W2 [432(453)/480], S65T [489/511], P4-1 [504(396)/480], S65A [471/504], S65C [479/507], S65L [484/510], Y66F [360/442], Y66W [458/480], I0c [513/527], W1B [432(453)/476(503)], Emerald [487/508] and Sapphire [395/511]. This list is not exhaustive of fluorescent proteins known in the art; additional examples are found in the Genbank and SwissProt public databases.

A number of parameters of fluorescence output are envisaged including 1) measuring fluorescence emitted at the emission wavelength of the acceptor (A) and donor (D) and determining the extent of energy transfer by the ratio of their emission amplitudes;

2) measuring the fluorescence lifetime of D;

3) measuring the rate of photobleaching of D;

4) measuring the anistropy of D and/or A; or 5) measuring the Stokes shift monomer:eximer fluorescence.

Other labels may be used, however, depending on the detection method employed to monitor the signal generated by the label. Labels may be attached in a number of ways, such as by direct labelling at suitable amino acids, such as cysteines or lysines, with chemical labels, or by fusion with a polypeptide label such as a fluorescent polypeptide. Techniques for labelling polypeptides are generally known in the art and may be applied to the present invention.

Preferably, one or more of the polypeptides in each complex according to the invention may be susceptible to modification. As noted above, susceptibility to modification indicates that the polypeptide may be subjected to proteolytic degradation under the appropriate conditions, which in a preferred embodiment means that the polypeptide is cleaved by a protease at a recognition site for the protease enzyme. Alternatively, however, the polypeptide may be susceptible to digestion by an exoprotease, from the N or C terminus. Alternatively, the polypeptide may be susceptible to acylation under the appropriate conditions. In a highly preferred embodiment, the polypeptide may be susceptible to phosphorylation under appropriate conditions. Peptides may be rendered susceptible to modification by inclusion within the peptide sequence of a recognition site for a modification enzyme. This may be performed using peptide synthesis techniques as described above.

Polypeptides according to the invention should be constructed such that the protease cleavable site is positioned such that cleavage thereof disrupts binding of the polypeptide in the context of the multimer. Thus, polypeptides which have been subjected to protease cleavage should dissociate from the multimer. Preferably, the protease does not cleave then polypeptide in such a manner that the label becomes detached therefrom without the binding abilities thereof being disrupted. Location of the protease cleavable site may be determined empirically. As a guide, however, the site should be placed within or proximal to the binding domain which is responsible for the multimerisation of the polypeptide.

In the case of coiled coil binding domains, Lumb et al (Subdomain folding of the coiled coil leucine zipper from the bZIP transcriptional activator GCN4, Lumb, K. J., Carr, C. M. & Kim, P. S., Biochemistry (1994) 33 7361–7367) teach that the loss of ten residues from the N-terminus or seven from the N- and six from the C-terminus is sufficient to destabilise the coiled coil peptide sequence known as GCN4-p1 (Evidence that the leucine zipper is a coiled coil, O'Shea, E. K., Rutkiowski, R. & Kim, P. S. (1989) Science 243 538–542). Su et al provide data indicating that there is a sharp decrease in the stability of a designed coiled coil with a decrease in chain length from 23 to 19 residues (Su, J. Y., Hodges, R. S. & Kay, C. M., Biochemistry (1994) 33 15501–15510). Accordingly, cleavage sites may positioned such that the coiled coil is disrupted to an extent that it is no longer capable of directing multimerisation.

The cleavage sites of a number of proteases are known in the art, and set forth in Table 3.

TABLE 3

| Protease | Cut Site(s) | Possible/Proven Role |
|---|---|---|
| Aminopeptidase M | Hydrolysis from free N-terminus | digestion |
| Carboxypeptidase P | Hydrolysis from C-terminus | digestion |
| Carboxypeptidase Y | Hydrolysis from C-terminus | digestion |
| Caspase 1, 4, 5 | W/LEHD-X[#] | mediator of apoptosis |
| Caspase 2, 3, 7 | DEXD-X[#] | mediator of apoptosis |
| Caspase 6, 8, 9 | L/VEXD-X[#] | mediator of apoptosis |
| Chymotrypsin | Y-X, F-X, T-X, (L-X, M-X, A-X, E-X) | digestion |
| Factor Xa | IEGR-X | blood clotting cascade |
| Pepsin | F-Z, M-Z, L-Z, W-Z (where Z is a hydrophobic residue) but will cleave others | digestion |
| TEV | E(N)XYXQ-S/G~ | polyprotein processing/as a reagent |
| Thrombin | R-X | blood clotting cascade |
| Trypsin | R-X, K-X | digestion |

[#]Ideal cut sites identified by Thornberry et al in A combinatorial approach defines specificities of members of the caspase family and granzyme B, Journal of Biological Chemistry 272 17907–17911.
~Release of proteins and peptides from fusion proteins using a recombinant plant virus proteinase, Parks, T. D., Keuther, K. K., Howard, E. D., Johnston, S. A. & Dougherty, W. G., Analytical Biochemistry (1994) 216 413–417; Life Technologies Ltd.

The sequence identifiers for several of the protease cut site listed above are as follows: Caspase 1,4,5, W/LEHD-X (SEQ ID NO:20); Caspase 2,3,7 DEXD-X (SEQ ID NO:21); Caspase 6,8,9 L/VEXDX (SEQ ID NO:22); Factor Xa IEGR-X (SEQ ID NO:23); TEV E(N)XYXQ-S/G (SEQ ID NO:24).

The foregoing, or other, sites may be engineered into or close to the binding domains of polypeptides according to the invention.

In a preferred aspect of the present invention, it is desirable to engineer specificity into the polypeptide, such that it is digested only by the desired protease and only at the intended protease cleavable site. This may be achieved, for example, by the use of D-isomers of amino acids in the construction of the polypeptide. D-amino acids are resistant to protease digestion, and a polypeptide constructed of D-amino acids will withstand proteolytic attack. Moreover, use of D-amino acids does not interfere with the protein-protein interactions involved in multimerisation, such as the interaction of protein binding domains, especially coiled-coil domains, provided that D amino acids are employed in both members of a binding pair.

In order to allow digestion by the intended protease enzyme, the D-amino acid constructions of the polypeptides of the invention contain one or more parts constructed of L-arnino acids, or otherwise rendered susceptible to proteolytic digestion. For example, coiled coils constructed of D-amino acids preferably comprise inserts, constructed wholly or partly of L-amino acids, which contain the protease cleavage site. The L-amino acid insert may be of any size, and may be positioned between coiled coil repeats, or between residues of the coiled coil. Preferred are insertions between residues b-c, e-f and f-g. The insert is covalently attached to the coiled coil, through a peptide linkage to the backbone or through a sidechain.

The insert may comprise only a cleavage site, or an entire polypeptide. Functionally, the insert is sufficiently flexible to permit the coiled coil to bind to its target efficiently when the insert is intact. For example, the insert may comprise a flexible linker, such as a gly-gly linker. Molecules comprising D-amino acids are advantageously employed in in vitro assays.

Inserts as described above may be employed in D-amino acid coiled coils, in conventional L-amino acid coiled coils, or in coiled coils which are partially D and partially L in construction. Foe example, a coiled coil may be constructed such that it consist of L-amino acids on one side of the insert, and D-amino acids on the other side thereof.

Generation of a Detectable Signal

Depending on the embodiment in question, signal useful in the present invention may be generated by a number of different labels. Preferred are fluorescent labels, and particularly preferred are fluorescent labels which participate in energy transfer (FRET).

FRET is detectable when two fluorescent labels which fluoresce at different frequencies are sufficiently close to each other that energy is able to be transferred from one label to the other. FRET is widely known in the art (for a review, see Matyus, 1992, *J. Photochem. Photobiol. B: Biol.,* 12: 323–337, which is herein incorporated by reference). FRET is a radiationless process in which energy is transferred from an excited donor molecule to an acceptor molecule; the efficiency of this transfer is dependent upon the distance between the donor an acceptor molecules, as described below. Since the rate of energy transfer is inversely proportional to the sixth power of the distance between the donor and acceptor, the energy transfer efficiency is extremely sensitive to distance changes. Energy transfer is said to occur with detectable efficiency in the 1–10 nm distance range, but is typically 4–6 nm for favourable pairs of donor and acceptor.

Radiationless energy transfer is based on the biophysical properties of fluorophores. These principles are reviewed elsewhere (Lakowicz, 1983, *Principles of Fluorescence Spectroscop*, Plenum Press, New York; Jovin and Jovin, 1989, *Cell Structure and Function by Microspectrofluoroy*, eds. E. Kohen and J. G. Hirschberg, Academic Press, both of which are incorporated herein by reference). Briefly, a fluorophore absorbs light energy at a characteristic wavelength. This wavelength is also known as the excitation wavelength. The energy absorbed by a fluorochrome is subsequently released through various pathways, one being emission of photons to produce fluorescence. The wavelength of light being emitted is known as the emission wavelength and is an inherent characteristic of a particular fluorophore. Radiationless energy transfer is the quantum-mechanical process by which the energy of the excited state of one fluorophore is transferred without actual photon emission to a second fluorophore. That energy may then be subsequently released at the emission wavelength of the second fluorophore. The first fluorophore is generally termed the donor (D) and has an excited state of higher energy than that of the second fluorophore, termed the acceptor (A). The essential features of the process are that the emission spectrum of the donor overlap with the excitation spectrum of the acceptor, and that the donor and acceptor be sufficiently close. The distance over which radiationless energy transfer is effective depends on many factors including the fluorescence quantum efficiency of the donor, the extinction coefficient of the acceptor, the degree of overlap of their respective spectra, the refractive index of the medium, and the relative orientation of the transition moments of the two fluorophores. In addition to having an optimum emission range overlapping the excitation wavelength of the other fluorophore, the distance between D and A must be sufficiently small to allow the radiationless transfer of energy between the fluorophores.

FRET may be performed using proteins labelled by methods known in the art. According to the invention, two coiled-coil domains comprised either by the same or by different polypeptide molecules are differentially labelled, one with a donor and the other with an acceptor moiety, and differences in fluorescence between a test assay, comprising a protein modifying enzyme, and a control, in which the modifying enzyme is absent, are measured using a fluorimeter or laser-scanning microscope. It will be apparent to those skilled in the art that excitation/detection means can be augmented by the incorporation of photomultiplier means to enhance detection sensitivity. The differential labels may comprise either two different fluorescent moieties (e.g., fluorescent proteins as described below or the fluorophores rhodamine, fluorescein, SPQ, and others as are known in the art) or a fluorescent moiety and a molecule known to quench its signal.

In a FRET assay of the invention, the fluorescent labels are chosen such that the excitation spectrum of one of the labels (the acceptor label) overlaps with the emission spectrum of the excited fluorescent label (the donor label). The donor label is excited by light of appropriate intensity within the donor's excitation spectrum. The donor then emits some of the absorbed energy as fluorescent light and dissipates some of the energy by FRET to the acceptor fluorescent label. The fluorescent energy it produces is quenched by the acceptor fluorescent label. FRET can be manifested as a reduction in the intensity of the fluorescent signal from the donor, reduction in the lifetime of its excited state, and re-emission of fluorescent light at the longer wavelengths (lower energies) characteristic of the acceptor. When the donor and acceptor labels become spatially separated, FRET is diminished or eliminated.

One can take advantage of the FRET exhibited by two polypeptides labelled with different fluorescent labels, wherein one polypeptide is linked to a donor and another to an acceptor label, in monitoring polypeptide modification according to the present invention. Two distinct polypeptides each comprising a coiled-coil may be differentially labelled with the donor and acceptor fluorescent protein moieties, respectively.

The means by which polypeptides are assayed for association using fluorescent protein moiety labels according to the invention may be briefly summarised as follows:

Of two polypeptides which associate into a complex according to the present invention, one is labelled with a green fluorescent protein, while the other is preferably labelled with a red or, alternatively, a blue fluorescent protein. Useful donor:acceptor pairs of fluorescent proteins (see WO 97/28261) include, but are not limited to:

Donor: S72A, K79R, Y145F, M153A and T203I (excitation 395 nm; emission 511) Acceptor: S659, S72A, K79R and T203Y (wavelengths not noted), or T203Y/S65G, V68L, Q69K or S72A (excitation 515 nm; emission 527 nm).

An example of a blue:green pairing is P4-3 (shown in Table 1 of WO 97/28261) as the donor moiety and S65C (also of Table 1 of WO 97/28261) as the acceptor moiety. The polypeptides are exposed to light at, for example, 368 nm, a wavelength that is near the excitation maximum of P4-3. This wavelength excites S65C only minimally. Upon excitation, some portion of the energy absorbed by the blue fluorescent protein moiety is transferred to the acceptor moiety through FRET if the two polypeptides are in close association. As a result of this quenching, the blue fluorescent light emitted by the blue fluorescent protein is less bright than would be expected if the blue fluorescent protein existed in isolation. The acceptor moiety (S65C) may re-emit the energy at longer wavelength, in this case, green fluorescent light.

After modification, the polypeptides physically separate, accordingly inhibiting FRET. Such a system is useful, for example to monitor the activity of proteolytic enzymes that cleave polypeptides to which the fluorescent labels are fused as well as the activity of modulators or candidate modulators of those enzymes.

In particular, the invention contemplates assays in which the amount or activity of a modification agent in a sample is determined by contacting the sample with a pair of polypeptides differentially labelled with fluorescent proteins, as described above, and measuring changes in fluorescence of the donor moiety, the acceptor moiety or the relative fluorescence of both. Fusion proteins as described above can be used for, among other things, monitoring the activity of a kinase enzyme inside a cell where the invention is practised in vivo.

Advantages of fluorescent polypeptides constructed as fusions with fluorescent proteins include the greater extinction coefficient and quantum yield of many of these proteins compared with those of the Edans fluorophore. Also, the acceptor in such a construct or pair of constructs is, itself, a fluorophore rather than a non-fluorescent quencher like Dabcyl. Thus, the enzyme's substrate, i.e., the unmodified polypeptide of the construct(s) and products (i.e., the polypeptides after modification) are both fluorescent but with different fluorescent characteristics.

In particular, the substrate and modified products exhibit different ratios between the amount of light emitted by the donor and acceptor labels. Therefore, the ratio between the two fluorescence emission values measures the degree of conversion of substrate to products, independent of the absolute amount of either, the optical thickness of the sample, the brightness of the excitation lamp, the sensitivity of the detector, etc. Furthermore, Aequorea-derived or related fluorescent protein moieties tend to be resistant to degradation, e.g. by proteases. Therefore, they are likely to retain their fluorescent properties throughout the course of an experiment.

In a further embodiment, a signal may be generated by using a redox enzyme as a label. Such systems are based on glucose oxidase (GOX) sensor technology. A number of glucose sensors have been produced to determine the concentration of glucose in a biological fluid (see U.S. Pat. Nos. 5,605,152, 5,849,174, 5,215,887, 5,082,786, 577,967, 5,755,953, 5,225,064 and 5,682,884; incorporated herein by reference).

In a first aspect of the present embodiment, the invention may be configured to exploit first generation GOX technology, which is oxygen-dependent:

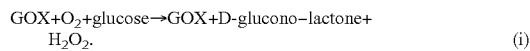

$$GOX + O_2 + \text{glucose} \rightarrow GOX + \text{D-glucono-lactone} + H_2O_2. \quad (i)$$

$$\text{D-glucono-lactone} \rightarrow \text{gluconic acid} \quad (ii)$$

There are several ways in which the glucose concentration can be coupled to a means of detection, including the following preferred techniques.

The first is to measure the decrease in pH caused by the production of gluconic acid. GOX is immobilised on an ion sensing device. On dipping into the sample fluid any glucose present leads to catalytic turnover and the production of gluconic acid.

The second method couples the turnover of GOX to that of horseradish peroxidase (HRP). HRP catalyse s the conversion of hydrogen peroxide to water, equation (iii).

$$HRP + H_2O_2 \rightarrow 2H_2O + HRP \quad (iii)$$

The redox active dye 0-dianisidine reduces $H_2O_2$. Formation of the radical cation of the dye reflects the catalytic activity of GOX and is monitored spectrophotometrically at 440 nm.

In a preferred aspect, however, second generation GOX technology is employed. This has the advantage of producing an electrical signal in response to stimulus, which is easily assayed.

An example is found in U.S. Pat. No. 5,682,884. The device described is a small, two electrode strip. One electrode is a reference electrode consisting of Ag and/or AgCl. The other is a carbon electrode. $O_2$ is replaced by a redox active mediator such as ferricyanide, $[Fe(CN)_6]^{3-}$, or a ferrocene derivative (1,1'-dimethylferrocene). The mediator and GOX are screen printed onto the carbon electrode. The sample fluid is placed over both electrodes. GOX will turn over on any glucose present (iv). The mediator acts to transfer electrons from GOX to the electrode surface (v). The potential difference produced is measured by a voltmeter or similar device.

$$GOX + \text{glucose} \rightarrow \text{D-glucano-lactone} + GOXH_2 \quad (iv)$$

$$GOXH_2 + 2[Fe(CN)_6]^{3-} \rightarrow GOX + 2[Fe(CN)_6]^{4-} \quad (v)$$

Coiled-coil technology may be combined with glucose sensing technology in a wide range of possible configurations. Such approaches involve fusing GOX to coiled-coil peptides. Basing this on the second generation assay described above, sensors are designed to operate as follows.

A polypeptide according to the invention is immobilised on the surface of a carbon electrode in a standard GOX assay. The mediator (ferricyanide or ferrocene) is screen printed on the electrode as for a standard GOX assay. The sample fluid drop is placed on the electrodes. A GOX-fusion binding partner peptide may be included in this screen print formulation or added after the sample. Either way the OGC-fusion binding partner binds to the immobilised polypeptide positioning GOX is at the surface of the electrode. Providing glucose is present, GOX will turn over passing electrons to the electrode via the mediator. Thus an output is provided conditional on binding of the binding partner polypeptide to the immobilised polypeptide. The potential difference generated is measured with a voltmeter or similar instrument. On disruption of the multimer by modification GOX is removed from the surface of the electrode and the circuit is broken. The glucose assay is advantageously configured such that it operates efficiently when the binding partner polypeptide, and so GOX, are held close to the electrode by the immobilised polypeptide.

This system couples the glucose assay to polypeptide modification events and uses it as a signal. For example, where coiled-coil dimers are disrupted by phosphorylation events, the signal is indicative of the phosphorylation state of the polypeptides. Prior to phosphorylation GOX turns over on glucose and a potential difference is observed. When phosphorylation of the peptides occurs, the dimer dissociates and enzymatic turnover is impaired, reducing the potential difference. Such a system is equally applicable to other modifications, such as proteolysis.

The system may be extended using a wide range of redox proteins and substrates in place of the glucose oxidase system. These include:

| Enzyme | Substrate |
| --- | --- |
| Pyruvate oxidase | Pyruvate |
| L-amino acid oxidase | L-amino acids |
| Aldehyde oxidase | Aldehydes |
| Xanthine oxidase | Xanthines |
| Glycollate oxidase | Glycollate |
| Sarcosine oxidase | Sarcosine |
| Lactate oxidase | Lactate |
| Glutathione reductase | NAH(P)H |
| Lipoamide dehydrogenase | NADH |
| Glucose dehydrogenase | Glucose |
| Methanol dehydrogenase | Methanol (alkanols) |
| Methylamine dehydrogenase | Methylamine |
| Lactate dehydrogenase (yeast cyt b$_2$) | Lactate |
| Horseradish peroxidase | Hydrogen peroxide |
| peroxidases | Hydrogen peroxide |
| Carbon monixide oxidoreductase | Carbon monoxide |
| Galactose oxidase | Galactose |
| Yeast cyt c | |

In a preferred aspect, the invention permits the design of a multiple assay system. Each assay produces an electrical signal allowing monitoring of the enzymatic reaction in each case. Thus a series of assays (with various enzymes) may be performed on one biological sample. Alternatively a range of substrates may be included to assay for the substrate specificity of one enzyme. Again, a polypeptide according to the invention is immobilised on the electrode surface. A binding partner polypeptide is fused to the enzyme of interest and may be included in the screen print formulation or added to the sample fluid.

Modification of Polypeptides

Digestion of polypeptides according to the invention with proteolytic enzymes may be carried out according to techniques and procedures known in the art. Thus, appropriate amounts of polypeptides according to the invention are incubated in appropriate conditions, for example with an appropriate buffer.

As used herein, the term "appropriate buffer" refers to a medium which permits activity of the protease enzyme used in an assay of the invention, and is typically a low-ionic-strength buffer or other biocompatible solution (e.g., water, containing one or more of physiological salt, such as simple saline, and/or a weak buffer, such as Tris or phosphate, or others as described hereinbelow), a cell culture medium, of which many are known in the art, or a whole or fractionated cell lysate; provided that it is compatible with the binding of the components of the assay of the invention, and with the selected signal employed. For example, the buffer advantageously does not include agents which quench fluorescence, if the signal is a fluorescent signal. An "appropriate buffer" permits modification of polypeptides according to the invention and, preferably, inhibits degradation and maintains biological activity or the reaction components. Inhibitors of degradation, such as nuclease inhibitors (e.g., DEPC) are well known in the art. Lastly, an appropriate buffer may comprise a stabilising substance such as glycerol, sucrose or polyethylene glycol.

As used herein, the term "appropriate amounts of polypeptides" refers to an amount of labelled polypeptides of the invention which emit a signal within the detection limits of a measuring device used in an assay of the invention. Such an amount is great enough to permit detection of a signal, yet small enough that a change in signal emission is detectable (e.g., such that a signal is below the upper limit of the device).

Configuration of the invention using a Homomultiner Comprising a Protease Cleavage Site In one embodiment of the present invention, the assay may be configured to use polypeptides, which are cleavable by a protease at a specific protease cleavable site.

This assay requires the formation of an oligomer of binding partners containing a proteolytic site or with a proteolytic site engineered therein which are labelled with fluorophores appropriate for FRET (or some other appropriate means of detection). The coiled coil provides a good example of such an oligomer. The sequence of the coiled coil part of the peptides in this reporter is short, such that it contains at least two heptad structures. Within this heptad structure an amino acid sequence recognised as a cleavage site for a protease is included. Cleavage of the peptide by the protease will reduce the length of the continuous coiled coil sequence, and destabilise oligomer formation. The fluorophores (F1, F2; where F1 is the donor fluorophore and F2 the acceptor) should be positioned such that they are covalently attached to separate peptides in the oligomeric complex at positions which are close in space in this complex but are not attached to a residue which affects enzyme processing of the substrate.

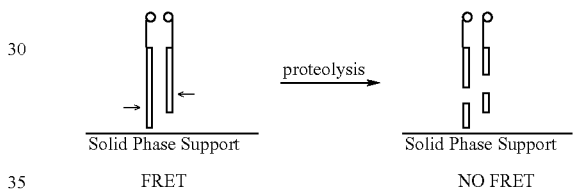

This illustrates an assay based on a homo-oligomeric assembly of peptides.

Configuration of the Invention using a Heteromultimer Comprising a Protease Cleavage Site The assay may, however, also be configured as a heteromultimeric assay in which one or more of the polypeptides comprises a protease cleavage site.

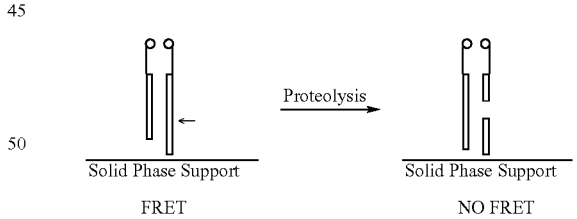

Clearly, the assay may be modified with respect to the above diagram in order to permit proteolytic degradation of more than one polypeptide in the complex. However, one of the advantages of heteromultimeric assays is that only a single polypeptide is digested.

Configuration of the Invention Using a Heteromultimer Susceptible to Proteolytic Degradation The invention may be configured to monitor the degradation of polypeptides, especially naturally-occurring polypeptides, as a result of proteolytic degradation. For instance, a polypeptide may be produced as a fusion with a further polypeptide which is to be assayed for proteolytic degradation. Protease enzymes which degrade the further polypeptide will also degrade the polypeptide of the invention, giving rise to complex dissociation.

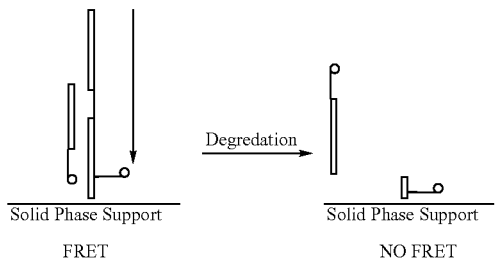

Since the complex is, in this embodiment, potentially much larger than the labelled dissociated polypeptide, the use of detection techniques reliant on label diffusion such as FCS is facilitated. Moreover, the use single labelled polypeptides, in conjunction with FCS detection, is made possible.

Configuration of Single-polypeptide Binding Domains

Single-polypeptide reagents may be configured in a number of ways, depending on the location of the labels with respect to the binding domains on the polypeptide. In a first example, the labels are positioned N- and C-terminal to the respective binding domains:

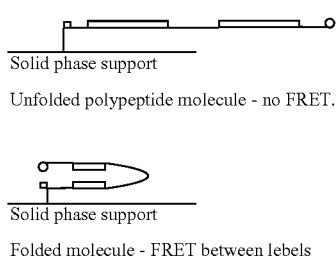

Modification of the polypeptide and loss of association between the binding domains leads to unfolding of the molecule and loss of FRET.

Configuration of the Invention Using Polypeptides Susceptible to Phosphorylation Polypeptides may be produced which associate in a phosphorylation-dependent manner. This may mean that association only occurs if one or more of the polypeptides is phosphorylated at one or more sites. Alternatively, this may mean that the polypeptides only associate if they are in the unphosphorylated state.

Preferably, the polypeptide which is susceptible to phosphorylation is immobilised and associates with a second polypeptide in the unphosphorylated state. When phosphorylation of the first polypeptide occurs, the association is measurably reduced.

In this case, by contacting the bound polypeptide pair with a sample which may contain a kinase, and allowing the kinase reaction to occur, it is possible to monitor the phosphorylation reaction by measuring the reduction in association between the first and second polypeptides. Furthermore, this measurement of association, as an assay of phosphorylation, may be taken repeatedly, providing a method for conducting real time kinase assays.

Alternatively, it may be possible to configure the assay such that the polypeptides associate only in the phosphorylated state. In this case, it would be possible to detect the phosphorylation of one or more polypeptides as an increase in association as phosphorylation occurred, or in a preferred embodiment, phosphatase activity could be monitored as a reduction in the association of polypeptides as one or more of them became increasingly dephosphorylated.

The only requirement for the configuration of the assay in this fashion is that the association of polypeptides is to some extent modulated by the phosphorylation state of one or more of said polypeptides.

Configuration Using Multiple Fluorescent Emissions

Interaction or association of polypeptides may be measured by any suitable means as set out in this application. It will be recognised by those skilled in the art that some means of detection allow the monitoring of multiple pairs of interacting polypeptides by choosing the fluorophore labels in such a way that different pairs of polypeptides are labelled with different colour flours (i.e. FRET pairs which are configured such that their absorption and/or emission spectra are different from one another).

By practising the invention in this manner, it will be possible to measure association of a first pair of polypeptides by exciting with a first excitation wavelength and monitoring a first emission wavelength, and to measure association of a second pair of polypeptides by exciting with a second excitation wavelength and monitoring a second emission wavelength, both the first and second polypeptide pairs being present in the same sample.

Clearly, two such pairs may have similar absorption wavelengths, with different emission wavelengths, or may have different absorption wavelengths with similar emission wavelengths, or may differ from one another in both their absorption and emission wavelengths. It will be understood that for the practice of the invention in this manner, the only requirement is that the flours are arranged in such a way that FRET pairs may be separately monitored or otherwise distinguished.

Clearly, the only liritation to the number of polypeptide pairs which may be monitored in solution in the same sample is the number of different combinations of suitable fluorophores which are available.

Fluorophores or FRET pairs with different absorption/emission wavelengths are well known to those skilled in the art, and some examples of these are presented in table 2.

General Techniques Useful in the Invention

In the present invention, use is made of general techniques of biochemistry and molecular biology as described, for example, in Sambrook et al. as referred to above. Generally, such techniques are useful in the design of polypeptide molecules, and complexes thereof, according to the invention; the production thereof, especially by recombinant DNA techniques; the attachment of labels to the molecules; in the incubation of molecules according to the invention with protease enzymes; and the design of assay protocols to monitor protease activity.

Design of Polypeptides

This is described in the foregoing sections on polypeptide design.

Production of Molecules

Molecules according to the invention are advantageously produced in insect cell systems. Insect cells suitable for use in the method of the invention include, in principle, any lepidopteran cell which is capable of being transformed with an expression vector and expressing heterologous proteins encoded thereby. In particular, use of the Sf cell lines, such as the *Spodoptera frugiperda* cell line IPBL-SF-21 AE (Vaughn et al., (1977) In Vitro, 13, 213–217) is preferred.

The derivative cell line Sf9 is particularly preferred. However, other cell lines, such as Tricoplusia ni 368 (Kurstack and Marmorosch, (1976) Invertebrate Tissue Culture Applications in Medicine, Biology and Agriculture. Academic Press, New York, USA) may be employed. These cell lines, as well as other insect cell lines suitable for use in the invention, are commercially available (e.g. from Stratagene, La Jolla, Calif., USA).

As well as expression in insect cells in culture, the invention also comprises the expression of polypeptides in whole insect organisms. The use of virus vectors such as baculovirus allows infection of entire insects, which are in some ways easier to grow than cultured cells as they have fewer requirements for special growth conditions. Large insects, such as silk moths, provide a high yield of heterologous protein. The protein can be extracted from the insects according to conventional extraction techniques.

Expression vectors suitable for use in the invention include all vectors which are capable of expressing foreign proteins in insect cell lines. In general, vectors which are useful in mammalian and other eukaryotic cells are also applicable to insect cell culture. Baculovirus vectors, specifically intended for insect cell culture, are especially preferred and are widely obtainable commercially (e.g. from Invitrogen and Clontech). Other virus vectors capable of infecting insect cells are known, such as Sindbis virus (Hahn et al., (1992) PNAS (USA) 89, 2679–2683). The baculovirus vector of choice (reviewed by Miller (1988) Ann. Rev. Microbiol. 42, 177–199) is Autographa californica multiple nuclear polyhedrosis virus, AcMNPV.

Typically, the heterologous gene replaces at least in part the polyhedrin gene of AcMNPV, since polyhedrin is not required for virus production. In order to insert the heterologous gene, a transfer vector is advantageously used. Transfer vectors are prepared in E. coli hosts and the DNA insert is then transferred to AcMNPV by a process of homologous recombination.

Alternatively, molecules according to the invention may be expressed in bacterial, lower eukaryote or mammalian cell systems, or in transgenic animals.

cDNA or genomic DNA encoding polypeptides according to the invention can be incorporated into vectors for expression. As used herein, vector (or plasmid) refers to discrete elements that are used to introduce heterologous DNA into cells for either expression or replication thereof. Selection and use of such vehicles is well within the skill of the artisan. Many vectors are available, and selection of appropriate vector will depend on the intended use of the vector, the size of the DNA to be inserted into the vector, and the host cell to be transformed with the vector. Each vector contains various components depending on its function and the host cell for which it is compatible. The vector components generally include, but are not limited to, one or more of the following: an origin of replication, one or more marker genes, an enhancer element, a promoter, a transcription termination sequence and a signal sequence.

Both expression and cloning vectors generally contain nucleic acid sequence that enable the vector to replicate in one or more selected host cells. Typically in cloning vectors, this sequence is one that enables the vector to replicate independently of the host chromosomal DNA, and includes origins of replication or autonomously replicating sequences. Such sequences are well known for a variety of bacteria, yeast and viruses. The origin of replication from the plasmid pBR322 is suitable for most Gram-negative bacteria, the 2m plasmid origin is suitable for yeast, and various viral origins (e.g. SV 40, polyoma, adenovirus) are useful for cloning vectors in mammalian cells. Generally, the origin of replication component is not needed for mammalian expression vectors unless these are used in mammalian cells competent for high level DNA replication, such as COS cells.

Most expression vectors are shuttle vectors, i.e. they are capable of replication in at least one class of organisms but can be transfected into another class of organisms for expression. For example, a vector is cloned in E. coli and then the same vector is transfected into yeast or mammalian cells even though it is not capable of replicating independently of the host cell chromosome. DNA may also be replicated by insertion into the host genome. DNA can be amplified by PCR and be directly transfected into the host cells without any replication component.

Advantageously, an expression and cloning vector may contain a selection gene also referred to as selectable marker. This gene encodes a protein necessary for the survival or growth of transformed host cells grown in a selective culture medium. Host cells not transformed with the vector containing the selection gene will not survive in the culture medium. Typical selection genes encode proteins that confer resistance to antibiotics and other toxins, e.g. ampicillin, neomycin, methotrexate or tetracycline, complement auxotrophic deficiencies, or supply critical nutrients not available from complex media.

Selectable markers which may be used in fungal cells, for example yeast cells, include wild-type genes which complement auxotrophic defects in for example the Uracil (e.g. URA3 gene), Lysine (e.g. LYS2 gene), Adenine (e.g. ADE2 gene), Methionine (e.g. MET3 gene), Histidine (e.g. HIS3 gene), Tryptophan (e.g. TRP1 gene), Leucine (e.g. LEU2 gene) or other metabolic pathways. In addition, counter-selection methods are well known in the art. These enable genes to be selected against by the action of a chemical precursor which is harmless unless converted to a toxic product by the action of one or more gene(s). Examples of these include; 5-fluoro-orotic acid, which is converted to a toxic compound by the action of the URA3 gene product; a-amino-adipic acid, which is converted to a toxic compound by the LYS2 gene product; allyl alcohol, which is converted to a toxic compound by alcohol dehydrogenase activity as encoded by the ADH genes, or any other suitable selective regime known to those skilled in the art. Other selective markers are based on the expression of a gene in a fungus such as yeast which overcomes the metabolic arrest induced by, or toxicity of, a chemical entity which may be added to the growth medium or otherwise presented to the cells. Examples of these may include the KAN gene(s) which confer resistance to antibiotics such as G-148, the HIS3 gene which confers resistance to 3-amino-triazole, or the ADH2 gene which can confer resistance to heavy metal ions such as cadmium, or any other suitable genes which confer resistance to toxic or growth arresting regimes.

Since the replication of vectors is conveniently done in E. coli, an E. coli genetic marker and an E. coli origin of replication are advantageously included. These can be obtained from E. coli plasmids, such as pBR322, Bluescript© vector or a pUC plasmid, e.g. pUC18 or pUC19, which contain both E. coli replication origin and E. coli genetic marker conferring resistance to antibiotics, such as ampicillin.

Suitable selectable markers for mammalian cells are those that enable the identification of cells which have taken up vectors according to the invention, such as dihydrofolate reductase (DHFR, methotrexate resistance), thymidine kinase, or genes conferring resistance to G418 or hygromycin. The mammalian cell transformants are placed under selection pressure which only those transformants which have taken up and are expressing the marker are uniquely adapted to survive. In the case of a DHFR or glutamine synthase (GS) marker, selection pressure can be imposed by culturing the transformants under conditions in which the pressure is progressively increased, thereby leading to amplification (at its chromosomal integration site) of both the selection gene and the linked DNA that encodes a polypeptide according to the invention. Amplification is the process by which genes in greater demand for the production of a protein critical for growth, together with closely associated genes which may encode a desired protein, are reiterated in tandem within the chromosomes of recombinant cells. Increased quantities of desired polypeptide are usually synthesised from thus amplified DNA.

Expression and cloning vectors usually contain a promoter that is recognised by the host organism and is operably linked to a coding sequence. Such a promoter may be inducible or constitutive. The promoters are operably linked to DNA encoding a polypeptide according to the invention by removing the promoter from the source DNA by restriction enzyme digestion and inserting the isolated promoter sequence into the vector. Both the native promoter sequence associated with the polypeptide in question, where this is naturally occurring, and many heterologous promoters may be used to direct amplification and/or expression of nucleic acids. The term "operably linked" refers to a juxtaposition wherein the components described are in a relationship permitting them to function in their intended manner. A control sequence "operably linked" to a coding sequence is ligated in such a way that expression of the coding sequence is achieved under conditions compatible with the control sequences.

Promoters suitable for use with prokaryotic hosts include, for example, the b-lactamase and lactose promoter systems, alkaline phosphatase, the tryptophan (trp) promoter system and hybrid promoters such as the tac promoter. Their nucleotide sequences have been published, thereby enabling the skilled worker operably to ligate them to DNA encoding a polypeptide according to the invention, using linkers or adaptors to supply any required restriction sites. Promoters for use in bacterial systems will also generally contain a Shine-Delgarno sequence operably linked to the DNA encoding a polypeptide according to the invention.

Preferred expression vectors are bacterial expression vectors which comprise a promoter of a bacteriophage such as phagex or T7 which is capable of functioning in the bacteria. In one of the most widely used expression systems, the nucleic acid encoding the fusion protein may be transcribed from the vector by T7 RNA polymerase (Studier et al, Methods in Enzymol. 185; 60–89, 1990). In the $E.\ coli$ BL21(DE3) host strain, used in conjunction with pET vectors, the T7 RNA polymerase is produced from the 1-lysogen DE3 in the host bacterium, and its expression is under the control of the IPTG inducible lac UV5 promoter. This system has been employed successfully for overproduction of many proteins. Alternatively the polymerase gene may be introduced on a lambda phage by infection with an int-phage such as the CE6 phage which is commercially available (Novagen, Madison, USA). other vectors include vectors containing the lambda PL promoter such as PLEX (Invitrogen, NL), vectors containing the trc promoters such as pTrcHisXpressTm (Invitrogen) or pTrc99 (Pharmacia Biotech, SE), or vectors containing the tac promoter such as pKK223-3 (Pharmacia Biotech) or PMAL (new England Biolabs, MA, USA).

Moreover, the nucleic acids encoding polypeptides according to the invention preferably include a secretion sequence in order to facilitate secretion of the polypeptide from bacterial hosts, such that it will be produced as a soluble native peptide rather than in an inclusion body. The peptide may be recovered from the bacterial periplasmic space, or the culture medium, as appropriate.

Suitable promoting sequences for use with yeast hosts may be regulated or constitutive and are preferably derived from a highly expressed yeast gene, especially a *Saccharomyces cerevisiae* gene. Thus, the promoter of the TRP1 gene, the ADHI or ADHII gene, the acid phosphatase (PH05) gene, a promoter of the yeast mating pheromone genes coding for the a- or a-factor or a promoter derived from a gene encoding a glycolytic enzyme such as the promoter of the enolase, glyceraldehyde-3-phosphate dehydrogenase (GAP), 3-phospho glycerate kinase (PGK), hexokinase, pyruvate decarboxylase, phosphofructokinase, glucose-6-phosphate isomerase, 3-phosphoglycerate mutase, pyruvate kinase, triose phosphate isomerase, phosphoglucose isomerase or glucokinase genes, the *S. cerevisiae* GAL 4 gene, the *S. pombe* nmt 1 gene or a promoter from the TATA binding protein (TBP) gene can be used. Furthermore, it is possible to use hybrid promoters comprising upstream activation sequences (UAS) of one yeast gene and downstream promoter elements including a functional TATA box of another yeast gene, for example a hybrid promoter including the UAS(s) of the yeast PH05 gene and downstream promoter elements including a functional TATA box of the yeast GAP gene (PH05-GAP hybrid promoter). A suitable constitutive PHO5 promoter is e.g. a shortened acid phosphatase PH05 promoter devoid of the upstream regulatory elements (UAS) such as the PH05 (-173) promoter element starting at nucleotide -173 and ending at nucleotide -9 of the PH05 gene.

Gene transcription from vectors in mammalian hosts may be controlled by promoters derived from the genomes of viruses such as polyoma virus, adenovirus, fowlpox virus, bovine papilloma virus, avian sarcoma virus, cytomegalovirus (CMV), a retrovirus and Simian Virus 40 (SV40), from heterologous mammalian promoters such as the actin promoter or a very strong promoter, e.g. a ribosomal protein promoter, and from the promoter normally associated the naturally occurring sequence encoding the polypeptide at issue, provided such promoters are compatible with the host cell systems.

Transcription of a DNA encoding a polypeptide according to the invention by higher eukaryotes may be increased by inserting an enhancer sequence into the vector. Enhancers are relatively orientation and position independent. Many enhancer sequences are known from mammalian genes (e.g. elastase and globin). However, typically one will employ an enhancer from a eukaryotic cell virus. Examples include the SV40 enhancer on the late side of the replication origin (bp 100–270) and the CMV early promoter enhancer. The enhancer may be spliced into the vector at a position 5' or 3' to the coding sequence, but is preferably located at a site 5' from the promoter.

Advantageously, a eukaryotic expression vector encoding a polypeptide according to the invention may comprise a locus control region (LCR). LCRs are capable of directing high-level integration site independent expression of transgenes integrated into host cell chromatin, which is of importance especially where the gene is to be expressed in the context of a permanently-transfected eukaryotic cell line in which chromosomal integration of the vector has occurred, in vectors designed for gene therapy applications or in transgenic animals.

Eukaryotic expression vectors will also contain sequences necessary for the termination of transcription and for stabilising the mRNA. Such sequences are commonly available from the 5' and 3' untranslated regions of eukaryotic or viral DNAs or cDNAs. These regions contain nucleotide segments transcribed as polyadenylated fragments in the untranslated portion of the mRNA encoding the polypeptide according to the invention.

An expression vector includes any vector capable of expressing nucleic acids that are operatively linked with regulatory sequences, such as promoter regions, that are capable of expression of such DNAs. Thus, an expression vector refers to a recombinant DNA or RNA construct, such as a plasmid, a phage, recombinant virus or other vector, that upon introduction into an appropriate host cell, results in expression of the cloned DNA. Appropriate expression vectors are well known to those with ordinary skill in the art and include those that are replicable in eukaryotic and/or prokaryotic cells and those that remain episomal or those which integrate into the host cell genome. For example, DNAs encoding a polypeptide according to the invention may be inserted into a vector suitable for expression of cDNAs in mammalian cells, e.g. a CMV enhancer-based vector such as pEVRF (Mathias, et al., (1989) Nucl. Acid. Res. 17, 6418).

Particularly useful for practising the present invention are expression vectors that provide for the transient expression of DNA encoding polypeptides according to the invention in mammalian cells. Transient expression usually involves the use of an expression vector that is able to replicate efficiently in a host cell, such that the host cell accumulates many copies of the expression vector, and, in turn, synthesises high levels of polypeptides according to the invention. For the purposes of the present invention, transient expression systems are useful e.g. for identifying mutants of polypeptides according to the invention, to identify potential phosphorylation sites, or to characterise functional domains of the protein.

Construction of vectors according to the invention employs conventional ligation techniques. Isolated plasmids or DNA fragments are cleaved, tailored, and religated in the form desired to generate the plasmids required. If desired, analysis to confirm correct sequences in the constructed plasmids is performed in a known fashion. Gene presence, amplification and/or expression may be measured in a sample directly, for example, by conventional Southern blotting, Northern blotting to quantitate the transcription of mRNA, dot blotting (DNA or RNA analysis), or in situ hybridisation, using an appropriately labelled probe which may be based on a sequence provided herein. Those skilled in the art will readily envisage how these methods may be modified, if desired.

In accordance with another embodiment of the present invention, there are provided cells containing the above-described nucleic acids. Such host cells such as prokaryote, yeast and higher eukaryote cells may be used for replicating DNA and producing polypeptides according to the invention. Suitable prokaryotes include eubacteria, such as Gram-negative or Gram-positive organisms, such as *E. coli*, e.g. *E. coli* K-12 strains, DH5a and HB101, or Bacilli. Further hosts suitable for polypeptides according to the invention encoding vectors include eukaryotic microbes such as filamentous fungi or yeast, e.g. *Saccharomyces cerevisiae*. Higher eukaryotic cells include insect and vertebrate cells, particularly mammal cells, including human cells, or nucleated cells from other multicellular organisms. In recent years propagation of vertebrate cells in culture (tissue culture) has become a routine procedure. Examples of useful mammalian host cell lines are epithelial or fibroblastic cell lines such as Chinese hamster ovary (CHO) cells, NIH 3T3 cells, HeLa cells or 293T cells. The host cells referred to in this disclosure comprise cells in in vitro culture as well as cells that are within a host animal.

DNA may be stably incorporated into cells or may be transiently expressed using methods known in the art. Stably transfected mammalian cells may be prepared by transfecting cells with an expression vector having a selectable marker gene, and growing the transfected cells under conditions selective for cells expressing the marker gene. To prepare transient transfectants, mammalian cells are transfected with a reporter gene to monitor transfection efficiency.

To produce such stably or transiently transfected cells, the cells should be transfected with a sufficient amount of polypeptides according to the invention-encoding nucleic acid to form polypeptides according to the invention. The precise amounts of DNA encoding polypeptides according to the invention may be empirically determined and optimised for a particular cell and assay.

Host cells are transfected or, preferably, transformed with the above-captioned expression or cloning vectors of this invention and cultured in conventional nutrient media modified as appropriate for inducing promoters, selecting transformants, or amplifying the genes encoding the desired sequences. Heterologous DNA may be introduced into host cells by any method known in the art, such as transfection with a vector encoding a heterologous DNA by the calcium phosphate coprecipitation technique or by electroporation. Numerous methods of transfection are known to the skilled worker in the field. Successful transfection is generally recognised when any indication of the operation of this vector occurs in the host cell. Transformation is achieved using standard techniques appropriate to the particular host cells used.

Incorporation of cloned DNA into a suitable expression vector, transfection of eukaryotic cells with a plasmid vector or a combination of plasmid vectors, each encoding one or more distinct genes or with linear DNA, and selection of transfected cells are well known in the art (see, e.g. Sambrook et al. (1989) Molecular Cloning: A Laboratory Manual, Second Edition, Cold Spring Harbor Laboratory Press).

Transfected or transformed cells are cultured using media and culturing methods known in the art, preferably under conditions, whereby polypeptides according to the invention encoded by the DNA is expressed. The composition of suitable media is known to those in the art, so that they can be readily prepared. Suitable culturing media are also commercially available.

Labelling of Polypeptides

Many amino acid residues have chemistry allowing labelling with commercially available fluorescent or other labels. The most useful of these are those with ionisable side chains—aspartic acid, glutamic acid, lysine, arginine, cysteine, histidine and tyrosine. The labelling reagent may be a group conferring the desired property such as fluorescence, and preferably includes a group involved in the conjugation of said label to the target polypeptide. The most commonly used functional groups in this context are those which react with amines by either acylation or alkylation. These include isothiocyanates, isocyanates, acyl azides, NHS esters and many others. Also common is the use of thiol-directed groups such as haloacetates and maleimides. These label primarily at the free sulfhydryl group of cysteine residues.

A number of protocols have been devised to achieve labelling at a specific site in a synthesised peptide. These are well known to those skilled in the art, and many are detailed in Bioconjugate Techniques, G. T. Hermanson, Academic Press 1996. It is possible to bias reactions to achieve specific labelling on one functional group and to reduce promiscuous reaction of the label with other sites in the polypeptide. Alternatively, labelling of the molecule may be concurrent with synthesis. This may be achieved either by the use of a labelled amino acid in the synthesis process or by the specific deprotection and labelling of the residue of interest before deprotection of other potentially reactive residues at the completion of the synthesis.

Incubation of polypetides in Assays According to the Invention

Buffer/ionic strength—the incubation solution may comprise an appropriate buffer (as defined above) of an ionic strength suitable for the formation of a folded reporter molecule structure (likely to be 0–150 mM. of a suitable salt).

Concentration—peptides may be present at a concentration sufficiently high to allow formation of the folded reporter molecule and detection of the assay output (within the limits of instrumentation) but not so high that the detector is saturated.

Temperature—the temperature selected will preferably be suitable for both formation of the reporter multimer and also activity of any biological agents included in the assay (for example 4–40° C.).

Preferably, each of these parameters is empirically determined as the behaviour of the reporter molecule may be sequence dependent.

Configuration of the Invention Using Enzymatic Reporter

If the polypeptides of the invention comprise two or more parts of an enzymatic activity, it is possible to configure the assay in such a way that, when the polypeptides associate with one another, this enzymatic activity is reconstituted. In such a case, the association of the polypeptides may be measured by monitoring the modulation of this enzymatic activity.

This monitoring may be via some kind of biosensor, for example using Glucose oxidase as the enzyme as part of a miniature electrical sensor circuit.

Alternatively, the polypeptides of the invention may be designed in such a way that, when they associate, they reform an inhibitor of an enzymatic activity. In this case, the association of the polypeptides may be measured by monitoring the modulation of said enzymatic activity. For example, PKC activity may be monitored, and this activity may be modulated by association of polypeptides according to the invention reforming PKC inhibitor (PKCi).

The invention is described below, for the purpose of illustration only, in the following examples. Modifications of the techniques described herein will be apparent to those skilled in the art.

Methods of the Invention:

Purification of Enzymes

The enzymes described can be purified from natural sources or from cells/micro-organisms engineered to heterologously express these enzymes. All enzymes used to illustrate this invention are commercially available; details of cut and modification sites are shown in Table 3. The recombinant forms of these enzymes are sometimes expressed with extra tags (such as the 6-histidine extension) for the purpose of purification.

Synthesis of peptides

Peptides are synthesised by Fmoc or Tboc chemistry according to the methods of Atherton et al (1981) *J. Chem. Soc,* 538–546 and Merrifield, R. B (1963) *J. Am. Chem. Soc,* 85, 2149–2154 respectively. Following deprotection and cleavage from the resin, peptides are desalted by gel filtration chromatography and analysed by mass spectrometry, HPLC and Edman degradation sequencing using standard methodologies.

1. Heterologous Expression of Peptides

Peptides can be synthesised from the heterologous expression of cDNA sequences for domains of interest can be modified to include sequences for modification as appropriate, or synthetic gene of the same. Expression can be in prokaryotic or eukaryotic cells using a variety of plasmid vectors capable of instructing heterologous expression. Purification of these products is achieved by destruction of the cells (e.g. French Press) and chromatographic purification of the products. This latter procedure can be simplified by the inclusion of an affinity purification tag at one extreme of the peptide, separated from the peptide by a protease cleavage site (other than that of interest) if necessary.

Heterologous expression of the peptides as described above can also be adapted to facilitate in vitro or in vivo assay of modification events. The cDNA or synthetic gene used codes for the peptide to be expressed fused to a variant of GFP, at the N or C terminus. Two plasmids or a plasmid carrying two genes can be introduced such that two peptides are expressed, capable of forming a dimer and fused with different GFP variants capable of FRET. Thus, on expression of the two peptides, a dimer forms and FRET is observed. Modification events destroy the dimer and FRET is lost. The expression of the peptides in the cell to be investigated removes the need for microinjection of the reporter peptides.

Labelling of Peptides

Peptides are labelled with thiol reactive or primary amine reactive derivatives of fluorescein and tetramethylrhodamine or other suitable FRET partners (see table 2; Molecular Probes, Eugene, OR, USA) using procedures described by Hermanson, G. T (1996) *Bioconjugate Techniques*, Academic Press. London.

Fluorescent peptides are subsequently separated from the non-labelled peptides and the unreacted fluorophores by gel filtration or reverse phase chromatography.

Proteolytic Cleavage of Peptides

1. Chymotrypsin—Chymotrypsin is a small proteolytic enzyme (MW 21.600 Da) found in the gastrointestinal tract. It catalyses the hydrolysis of digestive proteins to large peptides. The cleavage of peptides is on the C terminal side of Y-X, F-X, W-X, L-X, M-X, A-X, D-X, E-X,. The peptide structures of this invention are adapted to provide a label molecule on the template which carries the modification site as well as the tag for immobilisation onto a physical support. The reporter molecule enables monitoring of cleavage by chymotrypsin.

2.

3. The following peptides are used to assay chymotrypsin activity according to the invention:

4.

5. Immobilised substrate polypeptide:
HHHHHHGGIAQLEQEIAQLEQENAY-LEQEIAQLEQEIAKLEQE (SEQ ID NO. 25)

Y represents the cleavage site for chymotrypsin with the cut occurring between Y and L residues, K represents the fluorophore modification site and the 6 His residues are used for immobilisation of the polypeptide.

Binding partner polypeptide:
IAQLKQKIAQLKQKNAQLKQKI-
AQLKQKICQLKQK (SEQ ID NO. 26)

C represents the label attachment site.

Lyophilised chymotrypsin is dissolved in 1 mM HCl. Peptides (0.001–100 µM) are cleaved by chymotrypsin (1:200–1:20 w/w) in 50 mM HEPES, pH 7.0, 10 mM $CaCl_2$ and 100 mM NaCl at 1–40 C for periods of time ranging from 0 to 24 hours.

Thrombin is a serine protease enzyme (37,000 Da), which selectively cleaves Arg—Gly bonds in fibrinogen. It is involved in the blood coagulation cascade, cleaving fibrinogen to fibrin which forms the blood clot. The activation of protein kinase C (PKC) by thrombin results in the blockade of the coagulation cascade and ultimately thrombin production. Thrombin also plays an important role in promoting mitosis in fibroblasts, chemotaxis in monocytes and neurite retraction in neurons.

The following polypeptides are used for the assay of thrombin activity according to the invention:

Immobilised substrate polypeptide:
HHHHHHGGIAQLEQEIAQLEQEN-
RQLEQEIAQLEQEIAKLEQE (SEQ ID NO. 27)

R represent the cleavage site for thrombin with the cut occurring between R and Q residues, the 6 His residues are used for immobilisation, and K represents the fluorophore attachment site.

Binding partner polypeptide:
IAQLKQKIAQLKQKNAQLKQKI-
AQLKQKICQLKQK (SEQ ID NO. 28)

C represents the label attachment site.

Peptides (0.001–100 µM) are cleaved by thrombin (1:100–1:10 w/w) in 50 mM Tris-HCl, pH 7.0, 100 mM NaCl, 2.5 mM $CaCl_2$, 0.1% 2-mercaptoethanol at 1–40 C for periods of time ranging from 0 to 24 hours.

6. Tobacco Etch Virus (TEV) protease—the enzyme is a 27,000 Da protein which plays an important role in processing the precursor of viral polyprotein (Mutational analysis of Tobacco Etch Virus polyprotein processing: cis and trans proteolytic activities of polyproteins containing the 49-kilodalton proteinase, Carrington, J. C., Cary, S. M. & Dougherty, W. G. (1988) *J. Virol,* 62 2313–2320). This enzyme is commonly used in processing and cleavage of specific tags which were inserted specifically to aid purification of targeted recombinant proteins. (Release of proteins and peptides from fusion proteins using a recombinant plant virus proteinase, Parks, T. D., Leuther, K. K., Howard, E. D., Johnston, S. A. & Dougherty, W. G. (1994) *Anal Biochem* 216 413–417). The seven amino acid recognition site sequence EXXYXQS (SEQ ID NO. 29) allows for highly specific cleavage with minimal undesirable cleavage of the recombinant protein of interest.

7.

8. TEV protease is assayed in this invention using the following peptides:

9.

10. Immobilised substrate peptide:
HHHHHHGGIAQLEQEIAQLEQENAY-
LQSEIAQLEQEIAKLEQE (SEQ ID NO. 30)

Residues in bold represent the consensus sequence for TEV site with the cleavage occurring between Q and S residues. K represents the fluorophore modification site. The 6 His residues are used for immobilisation.

Binding partner polypeptide:
IAQLKQKIAQLKQKNAQLKQKI-
AQLKQKICQLKQK (SEQ ID NO. 31)

C represents the label attachment site.

Peptides (0.001–100 µM) are cleaved by TEV (1:300–1:30 w/w) in 50 mM Tris-HCl (pH 7), 0.5 mM EDTA, 1 mM DTT or 42.2 mM $K_2HPO_4$, 7.8 mM $KH_2PO_4$, 0.5 mM EDTA pH 7.0 at 1–40 C for periods of time ranging from 0 to 24 hours.

Aminopeptidase M—Peptides (0.001–100 µM) are cleaved by Aminopeptidase M (1:50–1:500 w/w) in 42.2 mM $K_2HPO_4$, 7.8 mM $KH_2PO_4$ pH 7.0 at 1–40 C for periods of time ranging from 0 to 24 hours.

Carboxypeptidase Y—Peptides (0.001–100 µM) are cleaved by Carboxypeptidase Y (1:100–1:10 w/w) in 50 mM sodium citrate pH 6.0 or 42.2 mM $K_2HPO_4$, 7.8 mM $KH_2PO_4$, 150 mM NaCl at 1–40 C for periods of time ranging from 0 to 24 hours.

Carboxypeptidase P—Peptides (0.001–100 µM) are cleaved by Carboxypeptidase P (1:100–1:10) in 50 mM sodium citrate pH 4.0 or 42.2 mM $K_2HPO_4$, 7.8 mM $KH_2PO_4$, 150 mM NaCl at 1–40 C for periods of time ranging from 0 to 24 hours.

In each case reactions are monitored in a 1 cm cell in a JASCO 715 spectropolarimeter, the CD at 222 nm is observed to follow any change in structure of the peptides present (Circular Dichroism and Optical Rotary Dispersion of proteins and polypeptides, Alder, A. J., Greenfield, N. J. & Fasman G. D., in *Methods in Enzymology* (1973) 27, 675–796). To confirm the timecourse of the reaction samples are quenched in 1 mM PMSF or by other suitable means and analysed by mass spectrometry using standard methods.

Fluorescence Measurements of Proteolysis in vitro in Real Time

Fluorophore labelled peptides (in a 1:6 molar ratio of fluorescein-labelled (pepF) to tetramethylrhodamine-labelled (pepR) peptide) are mixed. Samples are analysed in a fluorimeter using excitation wavelengths relevant to pepF (~450 nm) and emission wavelengths relevant to pepF (~516 nm) and pepR (~580 nm). A ratio of emission from pepR over that from pepF following excitation at a single wavelength is used to determine the efficiency of FRET between fluorophores, and hence their spatial proximity. Typically the measurements are performed at 0–37 C as a function of time following the addition of the relevant protease in appropriate buffer as detailed above.

Reporter Group Proteolysis in Living Cells

PepF:PepR (where pepF and pepR represent reporter sequences specific for caspase activity) are microinjected into live cells (e.g. Jurkat or HeLa cells). The ratio of emission from pepR/pepF is measured as described above via a photomultiplier tube focused on a single cell. Induction of apoptosis is achieved by treating with anti-Fas monoclonal antibody or TNF-a plus cycloheximide respectively as described in Apoptotic cleavage of a-Fodrin by and ICE/Ced-3 protease, Journal of Biological Chemistry (1996) 271 31277–31282. Caspase activity is monitored as a change in the ratio of pepR/pepF fluorescence.

Immobilisation of Template Peptides on HisSorb and Biacore Supports

In these examples, immobilisation of peptides on HisSorb and Bicacore supports is based on the specifically engineered 6 histidine residues tail in the peptide or protein of interest, this tail binds specifically to the Ni-Nitrilotriacetic acid ligand bound to an appropriate support. 200 µl aliquots of peptides (0.1–100 mM) in a charge phase with $Ni^+$ buffer containing 50 mM potassium phosphate, pH 7.2, 150 mM NaCl are added to microplate wells, incubated for 1–2 hours at room temperature or overnight at 4 C. The unbound peptide is removed by washing the plates (soaking the wells) 4 times with buffer and drying by tapping on paper towels.

Preparation of Cell Lysates

A selection of cell cultures such as BHK fibroblasts, Swiss 3T3, or HeLa cells can be utilised to provide lysates. Cells are grown according to standard methods and then lysed by lytic agents such as digitonin or saponin. The cells are then centrifuged and the lysates are resuspended in appropriate buffers which are suitable for measurements of enzymic activities of interest.

Detection of Enzyme Activities on His-Sorb Support:

Cell lysates are added to the microplate wells containing the immobilised peptide template which has the modification site(s), incubated for periods ranging from 1 second to 24 hours. The plates are then washed with buffer and the measure of activity of cellular enzymes is judged by addition of the common partner to the wells (The FRET measurements indicate the presence or lack of modification).

TABLE 4

| Protease | Cut/Modification Site(s) | Possible/Proven Role |
|---|---|---|
| Chymotrypsin | Y-X, F-X, W-X, * L-X, M-X, A-X, D-X, E-X | Digestion |
| TEV | E(N)XYXQ-S/G** | Polyprotein processing/as a reagent |
| Thrombin | R-X* | blood coagulation cascade |
| Protein kinase A (Catalytic subunit) | RRXRRXS$ | Multiple functions |
| CaM kinase II | RXXSX$ | Multiple functions |
| S6 kinase | RXRXXS$ | Multiple functions |
| Aminopeptidase M | porcine kidney | |
| Carboxypeptidase P | Penicillium janthinellum | |
| Carboxypeptidase Y | yeast | Hayashi, R., Moore, S. & Stein, W.H., Journal of Biological Chemistry (1973) 248 2296–2302 |

*Unless otherwise stated cut sites are taken from data in the Boehringer Mannheim catalogue
**Parks, T.D. et al. (1994) Anal Biochem 216 413–417
$Kemp, B. E. and Pearson, R. B. (1990) TIBS. 15, 342–346.

The sequence identifiers for several of the protease cut/modification sites listed above are as follows: TEV E(N)XYXQ-S/G (SEQ ID NO:24); Protein kinase A RRXRRXS (SEQ ID NO:32); CaM kinase II RXXSX (SEQ ID NO:33); S6 kinase RXRXXS (SEQ ID NO:34).

EXAMPLE 1

Assay of Phosphorylation of a Polypeptide

In this example, the assay of the invention is used to detect modification of a polypeptide by chemical phosphorylation.

'Zip 3' is a polypeptide which has a phosphorylation site in the centre of the molecule, and has the following amino acid sequence:

R MKQLEDK VEELLSK TYHLENE VACLKKL VGERAAK (SEQ ID NO. 35)

This sequence is derived from amino acids 249–281 of GCN4 (Genbank Accession No. K02205; the sequence AAK has been added to the C-terminus of that polypeptide sequence, $N_{264}$ has been changed to T and $R_{273}$ has been changed to C. The threonine residue (shown here in bold type) is the residue which is to be phosphorylated. The cysteine residue (also shown in bold type) provides the site for attachment of thiol-directed fluorescent labels.

In the unphosphorylated state, Zip 3 has a coiled-coil (a-helical) tertiary structure.

In the unphosphorylated state, molecules of Zip 3 associate with each other.

It is shown that phosphorylation of Zip3 at the central threonine residue destabilises its coiled-coil structure. The experiments are summarised as follows:

The circular dichroism (measured in units of ellipticity) of proteins at 222 nm provides a measure of the amount of a-helix present in the structure, with a large, negative ellipticity indicting a high level of helicity. The coiled-coil has a distinctive a-helical CD spectrum with minima at 222 nm and 208 nm (O'Shea et al., 1989, Science, 243: 538–542). The CD spectra of the unmodified Zip3 and its phosphorylated form ('Zip3P') are determined at a sample concentration of 10 μM in 150 mM KCB, 42.2 mM $K_2HPO_4$, 7.8 mM $KH_2PO_4$, pH 7.0 at 20° C.; spectra are recorded using a 1 mm pathlength cell in a Jasco J-715 spectropolarimeter with a Jasco PTC-348W Peltier temperature control unit. Peptide concentration is determined by tyrosine absorbance at 280 nm in 6M GuHCl. The CD spectrum of Zip3 which is observed is that of a classic coiled-coil (O'Shea et al., 1989, supra), while that of Zip3P is indicative of random coil, unfolded. The ellipticities of Zip3 and Zip3P at 222 nm with increasing temperature are measured. The steep portion of the sigmoid curve for Zip3 indicates the unfolding of the molecule. It is clear that this leucine zipper peptide begins to unfold at around 35° C. and is completely unfolded by 70° C. The ellipticity of Zip3P fluctuates around a small negative value, demonstrating that this structure is unfolded even at the starting temperature of 1° C. and remains unfolded at all temperatures considered.

Peptides are labelled using a method adapted from one known in the art (Hermanson, 1996, Bioconjugate Techniques, Academic Press). 20 mM fluorescein iodoacetamide (FAM) in DMSO and 0.23 mM peptide in 20 mM TES buffer, pH 7.0 are prepared. These are mixed in a molar ratio of (0.9:1.0, label:peptide) and incubated at 4° C. in the dark for a minimum of 2 hours.

This method is also applied to labelling of a peptide with rhodamine maleimide at a ratio of (0.9:2.0, label:peptide); This method is also applied to labelling of a peptide using rhodamine iodoacetamide at a ratio of (0.9:1.0, label:peptide). Labelling is assessed by reverse phase HPLC (C18 column; solvent A: $H_2O/0.1\%$ TFA; solvent B: acetonitrile/0.1% TFA) and MALDI-TOF mass spectrometry. Zip3 peptides labelled with fluorescein (Zip3F) and rhodamine (Zip3R) are thus generated.

It is demonstrated that FRET occurs between fluorophores attached to unphosphorylated peptides which interact with each other, but that FRET does not occur between fluorophores attached to phosphorylated peptides which do not interact with each other (as evidenced by loss of structure in CD experiments).

Fluorescence at 516 nm is measured for labelled Zip3 polypeptides in a 1 cm pathlength cell at peptide concentrations of 0.08 μM Zip3F and 0.48 μM Zip3R in 50 mM kcb, 42.2 mM $K_2HPO_4$, 7.8 mM $KH_2PO_4$, pH 7.0 at 37° C. in a PII fluorimeter system with temperature controlled by a waterbath. Upon addition of Zip3R to Zip3F, fluorescence in the region of fluorescein emission decreases. This is accompanied by an increase in fluorescence detectable in the rhodamine emission region. These data demonstrate that energy transfer is taking place and that at least some of the energy emitted by the fluorescein is directly exciting the rhodamine label on the partner peptide. The fluorescence at 516 nm shows no decrease upon addition of Zip3PR (the phosphorylated form of Zip3R, added at time 500 seconds) to Zip3PF (the phosphorylated form of Zip3F). In addition, no FRET is observed when Zip3F is mixed with Zip3PR, indicating that when even one peptide partner is phosphorylated, neither formation of the coiled-coil structure nor protein:protein heterodimerisation (with respect to fluorophore composition), can occur.

These results show that FRET does not occur between the phosphorylated molecules, or between a phosphorylated and an unphosphorylated molecule.

These results show that monitoring of FRET between labelled polypeptides is used successfully in the invention to assay the phosphorylation state of peptides.

EXAMPLE 2

Assaying the Activity of a Polypeptide Modification Enzyme

In Example 1, the utility of interacting modifiable polypeptides as reporters of protein phosphorylation using FRET was demonstrated.

In the present Example, the application of such polypeptides to the assay of the activity of a polypeptide modification enzyme is illustrated.

Two variants of the peptide Zip4 (derived from amino acids 249–281 of GCN4; Genbank Accession No. K02205) are synthesised. The amino acid sequence of these peptides (Zip4S and Zip4T) is as follows:

```
Zip4S
                                            (SEQ ID NO. 36)
R MKQLEDQ VRRLRRK SYHLENE VACLKKL VGERAAK (as
Zip3, but also E_{258} ® R, E_{259} ® R, L_{261} ® R, S_{262}
® R and N_{264} ® S), and Zip4T
                                            (SEQ ID NO. 37)
R MKQLEDQ VRRLRRK TYHLENE VACLKKL VGERAAK (as
Zip4S, but S_{264} ® T).
```

The underlined arginine residues form the recognition site for PKA (Pearson and Kemp, 1991, *Methods Enzymol.*, 200: 62–81).

A timecourse of phosphorylation of these peptides by PKA is run in 50 mM histidine/HCl (pH 7.0), 5 mM $MgSO_4$, 5 mM NaF, 0.05 mM EGTA, 120 mM kcb with 0.2 mM ATP (30.9 cpm/pmol $^{32}$P-ATP) and 0.5 µM PKA. The results show that Zip 4S is a good substrate for the PKA enzyme, with a rate of phosphorylation comparable to that seen with a known substrate (PL919Y, a Phospholamban peptide; Drago and Colyer, 1994, *J. Biol. Chem.*: 269: 25073–25077). Zip4T is also phosphorylated, at a slower rate, with full phosphorylation achieved in 30 minutes in this assay. In this assay, the difference in cpm recovered between the Zip4 peptides and PL919Y is due to the difference in recovery of these peptides on P81 paper. The plateau indicates full phosphorylation.

A set of timecourses of phosphorylation is performed on Zip4S using PKA and $Ca^{2+}$/Calmodulin-dependent Protein Kinase (CaMK-II), together with positive and negative controls for CaMK-II (these controls confirm that the preparation of CaMK-II posesses the expected characteristics of that enzyme). PKA phosphorylation is performed in 50 mM histidine/HCl (pH 7.0), 5 mM $MgSO_4$, 5 mM NaF, 0.05 mM EGTA, 120 mM kcb with 0.2 mM ATP (39.72 cpm/pmol $^{32}$P-ATP) and 0.25 µM PKA. CaMK-II phosphorylation is performed in 50 mM histidine/HCl (pH 7.0), 5 mM $MgSO_4$, 5 mM NaF, 120 mM kcb, 0.5 mM $Ca^{2+}$, 0.037 mg/ml calmodulin with 0.2 mM ATP (39.72 cpm/pmol $^{32}$P-ATP) and 10% crude CaMK-II. In the $Ca^{2+}$-free experiment, $Ca^{2+}$ is replaced by 0.05 mM EGTA. The results indicate that the phosphorylation site in Zip4S is recognised only by C-PKA. CaMK-II is unable to phosphorylate Zip4S, while PKA mediates complete phosphorylation of that protein. Such specificity of a modification site in a polypeptide according to the invention is a clear advantage for use of the invention in an intracellular assay, or for measuring the activity of a particular polypeptide modifying agent in a complex mixture such as a cell lysate.

As in Example 1, circular dichroism is used to assess the tertiary structure of the Zip4 polypeptides and the disruption of that structure by phosphorylation. Both of the Zip4 peptides are found to be less thermostable than Zip3 when assayed under the same conditions (see Example 1), which is likely due to the introduction of a positively charged region to form the PKA recognition site. Zip4T was more stable than was Zip4S. Thermal denaturation (performed as described above; see Example 1) of enzymatically phosphorylated Zip4S shows that this modification disrupts alpha-helical coiled-coil formation and leads to an unfolded polypeptide in solution. This is confirmed by the CD spectra of Zip4S and Zip4SP at 1° C.

Fluorescence is used to report on the phosphorylation status of these peptides. A loss of emission at 516 nm is seen on addition of Zip4SR to Zip4SF, as FRET occurs when the differentially-labelled polypeptide partners are allowed to associate. Emission at around 575 nm also increases; whilst part of this increase may be attributable to direct excitation of the rhodamine label, the increase is consistently above that seen in the phosphorylated scan, suggesting that at least a proportion of the increase is due to excitation by FRET. On addition of PKA, emission at 516 nm returned to above the level produced by Zip4SF alone, while emission at 573 nm decreases slightly; this decrease accounts for the amount of FRET-derived emission which is lost. No loss of FRET is observed on addition of PKA in the absence of ATP.

Calculation of the ratio of fluorescence output is helpful in avoiding error due to variation in local concentrations of reporter in the system.

Initial inspection of the data in these experiments leads to a calculation of the ratio of fluorescence outputs at 573 nm and 516 nm; FRET is seen as an increase in the 573/516 nm ratio. A decrease is seen in the ratio following phosphorylation by PKA, although the value does not return fully to the baseline because of the contribution of the 573 nm emission produced by direct excitation of the rhodamine label.

These results demonstrate the applicability of this invention to the assay of enzymatic modification activity on a target substrate site present on a polypeptide according to the invention, and further indicate that Zip4S is a suitable molecule upon which to base an assay system of the invention.

EXAMPLE 3

Detection of Polypeptide Modification by Chemical Phosphorylation.

Pep 1 is a polypeptide which has a phosphorylation site in the centre of the molecule and has the following amino acid sequence:
HHHHHHGGIAQLEQEIRRLRRE-
SAQLEQEIAQLEQEIAKLEQE (SEQ ID NO. 38) (Pep 1)

This sequence is based on a wholly synthetic coiled coil structure according to O'Shea. E. K. et al, (1993). *Current Biology* 3, 658–667 and Nautiyal. S. at al, (1995) *Biochem-*

*istry* 34, 11645–11651. The sequence has poly-histidine insert added to its N terminus for immobilisation purposes and the two glycine residues are added as a spacer. The amino acid sequence in bold is inserted as a specific PKA recognition site and the underlined lysine residue is inserted for labelling purposes.

Pep 2 is a polypeptide which has no kinase modification sites and is synthesised to form a heterodimeric partner with Pep 1. The underlined cysteine residue is inserted for a label attachment purposes.

IAQLKQEIAQLKQKNAQLKQKIAQLKQKICQLKQK (SEQ ID NO. 39) (Pep 2)

In the unphosphorylated state Pep 1 associates with its partner Pep 2 to form a coiled coil oligomer.

In the phosphorylated state Pep 1 will not bind to Pep 2, thus coiled coil structures are not formed.

Biacore Assays for Immobilised Peptides

A Ni-NTA derivatised sensor chip (which is commercially available) is first washed with buffer containing 50 mM potassium phosphate, pH 7.2; 150 mM NaCl and 50 mM $NiSO_4$. Subsequently Pep 1 (0.01–100 μM in PBS buffer) which has the poly histidine tag is applied to the sensor chip. This binds specifically to the Ni-NTA support. The sensorgram shows a rise indicative of mass increase and therefore establish a new baseline. Once this baseline is stable, cell lysate (solubilised in PBS buffer), which is to be tested for PKA activity is passed onto the sensor chip for periods of time ranging from 5 sec to 30 min. Again the sensorgram shows a rise indicative of mass increase and reaches a new steady state. The sample is removed by washing with PBS buffer and the sensorgram signal falls to a baseline little different to the previous baseline.

Once this signal is stable, the partner peptide Pep 2 (0.01–100 μM in PBS buffer) is then applied to the sensor chip. At this stage the sensorgram is recorded for the change in mass When Pep 1 is unphosphorylated, Pep 2 associates with Pep 1, Thus giving an increase in mass which is observed via a positive signal of the sensorgram. This is indicative of the absence of PKA.

If Pep 1 is phosphorylated by PKA, however, Pep 2 does not associate with Pep 1, Thus no change in signal or mass is observed. This indicates the presence of PKA.

In order to perform this assay, a number of general techniques and test procedures are used. These are set out below, and find use in other embodiments of assays of this type.

Labelling of Peptides

Peptides are labelled using a method adapted from one known in the art (Hermanson, 1996, *Bioconjugate techniques*, Academic Press). 20 mM fluorescein iodoacetamide (FAM) in DMSO and 0.23 mM peptide in 20 mM TES buffer, pH 7.0 are prepared. These are mixed in a molar ratio of 0.9:1.0 (label:peptide) and incubated at 4 C in the dark for a minimum of 2 hours.

The method is also applied to labelling of a peptide with rhodamine maleimide and rhodamine iodoacetamide at a ratio of 0.9:1.0 (label:peptide). Labelling is assessed by reverse phase HPLC (C18 column; solvent A: $H_2O$/0.1% TFA; solvent B: acetonitrile/0.1% TFA) and MALDI-TOF mass spectrometry. Pep 1 peptide labelled with fluorescein (Pep 1F) and Pep 2 peptide labelled with rhodamine (Pep 2R) are thus generated.

Immobilisation of Substrate Peptides on Ni-NTA

Immobilisation of Pep 1 peptide on the Ni-NTA derivatised sensor chip is based on the specifically engineered 6-histidine residue tag in Pep 1. This tail binds specifically to the $Ni^{2+}$ ions attached to NTA. The Nitrilotriacetic acid ligand is bound to the chip according to manufacturers instructions; Pep 1 (0.01–100 μM in PBS buffer) is added to the microtitre wells (The capacity of binding is determined by the degree of derivatisation of Ni-NTA) and incubated for 1 to 2 hours at room temperature or overnight at 4 C. The unbound peptide is then removed by washing the sensor chip wells four times with PBS buffer. Excess wash buffer is removed.

Preliminary solution phase experiments to monitor the modification of the polypeptides prior to immobilisation on physical support are run to monitor the association/dissociation of coiled coil structure. These assays are done in two modes as follows:

FRET Measurements

Pep 1 and Pep 2 labelled as described above are assayed for association or dissociation upon addition of the modifying agent by FRET as follows:

Pep 1F (peptide labelled with fluorescein) is added at a concentration of 50 μM to a fluorimeter cuvette containing 2 ml of 50 mM potassium phosphate pH 7.2 in the presence of 120 mM kcb, 5 mM NaF, 5 mM $MgSO_4$, 0.05 mM EGTA and 2 mM ATP, and incubated for 10 minutes to reach thermal equilibrium at 37° C.

Fluorescence emission of fluorescein is measured at 520 nm by exciting at appropriate wavelength (450 nm). Pep 2R (Pep 2 labelled with rhodamine) at concentrations equal to that of Pep 1F (50 μM) is added and the fluorescence emission of Pep 1F and Pep 2R are monitored.

In the unmodified state Pep 2 associates with Pep 1 causing the fluorophores to approach each other. Thus, some of the energy emitted by fluorescein attached to Pep 1 is absorbed by rhodamine attached to pep2 peptide leading to fluorescence decrease.

Addition of PKA (1.0 μM) to Pep 1F either prior to or after the addition of Pep 2R leads to the phosphorylation of PEP 1 preventing its association with Pep2 R, and any alteration of the fluorescein fluorescence observed.

CD Measurements

The circular dichroism (measured in units of ellipticity) of proteins at 222 nm provides a measure of the amount of -helix present in the structure, with a large, negative ellipticity indicating a high level of helicity. The coiled coil has a distinctive -helical CD spectrum with minima at 222 nm and 208 nm (O'Shea et al. 1989. *Science,* 243, 538–542). The CD spectra of the unmodified peptide Pep 2 and its phosphorylated partner Pep 1 are determined at a sample concentration of 10 μM in 50 mM Tris.HCl, pH 7.2 and 120 mM kcb at 37 C.

Assaying PKA Activity on Substrates Immobilised to the Ni-NTA Derivatised Supports Time course of PKA activity on substrate peptides immobilised onto Ni-NTA derivatised supports is run in two modes as follows:

A. Pep 1F is immobilised on a Ni-NTA microplate, as described above. Excess Pep2R (100 μl of 1 μM peptide) is added to each well and incubated for 5 min at room temperature. Excess Pep 2R solution is removed by aspiration and 50 μl of potassium phosphate buffer pH 7.2; 150 mM NaCl, 5 mM NaF, 5 mM $MgSO_4$ and 0.5 mM ATP is added. FRET is measured by excitation at 450 nm and emission at 580 and 520 nm. The ratio of 580/520 is used to record FRET. Phosphorylation of Pep 1F is initiated by the addition of 1.0 μM PKA and the time course of phosphorylation followed by FRET 580/520 (excitation at 450 nm) over a 5 minute period.

B.

C. Pep 1F is immobilised on a Ni-NTA microplate, as described above. Phosphorylation of Pep 1F is initiated by the addition of 1.0 μM PKA, incubated for different time periods (0 sec–1 hour) at room temperature in a buffer containing 50 μl of potassium phosphate buffer pH 7.2; 150 mM NaCl, 5 mM NaF, 5 mM MgSO$_4$ and 0.5 mM ATP. Phosphorylation is then stopped by the addition of a specific PKA inhibitor and the solution reagents by aspiration. The wells are washed 4 times with buffer. Excess Pep 2R (100 μl of 1 μM peptide) is added to each well and incubated for 5 min at room temperature. Excess Pep 2R solution is removed by aspiration and FRET is measured by excitation at 450 nm and emission at 580 and 520 nm. The ratio of 580/520 is used to record FRET.

1.

2. In unphosphorylated (Unmodified Pep 1F) state Pep2R binds to Pep 1F leading to increase in FRET (seen as a decrease in the emission of the donor fluorophore, due to its absorbance by the acceptor fluorophore).

3.

4. On exposure to PKA, Pep1F is phosphorylated and there is no association between Pep 1F and Pep 2R, and thus no FRET.

EXAMPLE 4

Assay of Calmodulin-dependent Protein Kinase II(CaMK-II):

CaMK-II is an enzyme which consists of subunits of 50,000, 58,000–60,000 Da in a 3:1 ratio. It is a multifunctional enzyme which is dependent on Ca$^{2+}$ and calmodulin for its activity. It is involved in mediating various cellular processes in response to second messenger signalling stimuli including gene expression, neurotransmitter synthesis and release, calcium homeostasis, ion channel function, carbohydrate metabolism and cytoskeletal function (Hanson, P. I. & Schulman, H. (1992) *Annu. Rev. Biochem.* 61, 559) The consensus sequence required for recognition for CaMK-II is RXXSX (SEQ ID NO. 33).

The following peptides are used in the assay according to the invention to monitor CaMK-II activity:

Immobilised substrate polypeptide:
HHHHHHGGIAQLEQEIAQLRQE-SAQLEQEIAQLEQEIAKLEQE (SEQ ID NO. 40)

The residues in bold represent the recognition site, K is the fluorophore labelling site, and the 6 His residues are used for immobilisation.

Binding partner polypeptide:
IAQLKQEIAQLKQKNAQLKQKIAQLKQKICQLKQK (SEQ ID NO. 41)

C represents the label attachment site.

The peptides are labelled as in Example 1.

The substrate peptide is immobilised as in Example 3.

Phosphorylation of immobilised peptides (0.01–100 μM) by CaM kinase II is carried out in 50 mM Histidine buffer pH 7.0, 10 mM MgSO$_4$, 120 mM kcb, 5 mM Sodium Fluoride, in the presence or absence of Ca$^{2+}$/CaM. The reaction is initiated by the addition of 0.2 mM ATP at 30–37 C for periods ranging from 0–60 minutes.

The binding partner polypeptide (0.01–100 μM) is then added.

Association of the peptides, and hence phosphorylation of the substrate polypeptide, is measured using FRET as in Example 2.

EXAMPLE 5

Assay of S6 kinase

S6 Kinase is a single polypeptide chain (57,000 Da), playing an important role in protein synthesis. It exerts its function by phosphorylating the S6 P70 ribosomal protein. In response to various hormonal stimuli such as insulin (Novak-Hofer, I., & Thomas, G. (1984) *J. Biol. Chem.* 25, 5995–600., Nemenoff, R. A., Gunsalus, J. R., and Avruch, J. (1986) *Arch. Biochem. Biophys.* 245, 196–203)., growth factors (Novak-Hofer, I., & Thomas, G. (1984) *J. Biol. Chem.* 25, 5995–600., Belnis, J., & Erikson, R. L. (1985) *Proc. Natl. Acad. Sci. U.S.A.* 82 ,7621–7625., Pelech, S., Olwin, B. B., and Krebs, E. G. (1986) *Proc. Natl. Acad. Sci. U.S.A.* 83 5968–5972., oxidative stress (Larsson, R, & Cerutti, P. (1988) *J. Biol. Chem.* 263, 17452–17458). The S6 undergoes phosphorylation which triggers an enhanced protein synthesis (Palen, E., & Traugh, J. A. (1987) *J. Biol. Chem,* 262, 3518–3523). The consensus sequence required for recognition by S6 kinase is RXRXXS (SEQ ID NO. 34).

1.

The following peptides are used in this invention to assay S6 kinase activity:

2.

3. Immobilised substrate polypeptide:
HHHHHHGGIAQLEQEIARLRQE-SAQLEQEIAQLEQEIAKLEQE (SEQ ID NO. 42)

The residues in bold represent the recognition site, K is the fluorophore labelling site and the 6 His residues are used for immobilisation.

Binding partner polypeptide
IAQLKQEIAQLKQKNAQLKQKIAQLKQKICQLKQK (SEQ ID NO. 43)

C represents the label attachment site.

The peptides are labelled as in Example 1.

The substrate peptide is immobilised as in Example 3.

Immobilised peptides (0.01–100 μM) are incubated in a buffer containing 20 mM MOPS pH 7.2, 25 mM -glycerol phosphate, 1 mM Sodium orthovanadate and 1 mM dithiothrietol, in the presence of a cocktail of kinase inhibitors for PKA, PKC and CaM kinase known in the art. The reaction is initiated by the addition of 500 μM Mg-ATP.

The binding partner polypeptide (0.01–100 μM) is then added.

Association of the peptides, and hence phosphorylation of the substrate polypeptide, is measured using FRET as in Example 2.

EXAMPLE 6

Assay of Glycosylation

The peptide sequence shown below is based upon the p67$^{SRF}$ glycosylation acceptor site S-316 (Reason et al., 1992, supra) and the adaptor of that sequence, which have been modified to improve their compliance with a coiled-coil sequence pattern:

p67<sup>SRF</sup> (313–324): SAVSSADGTVL (SEQ ID NO. 44)

Zip5: HHHHHHGGIAQLEQEIAQL*SAVSS*ALGTVLAQLEQEIAKLEQE (SEQ ID NO. 45)

In this Zip5 peptide, the site of O-glycosylation is S-316 ('a' position of heptad 3), the sequence is based on that of p67$^{SRF}$ (313–323) sequence except for (D$_{319}$®L), and has undergone an extension of its sequence with sequence which complies with the canonical coiled-coil sequence to complete five heptads, and has an N-terminal 6-His residue extension in order to immobilise the peptide as in Example 3.

Binding partner polypeptide:
IAQLKQKIAQLKQKNAQLKQKI-AQLKQKICQLKQK (SEQ ID NO. 46)

Fluorophores are attached to the single Cys residue (shown in bold) in each partner polypeptide as in Example 1, the Zip5 polypeptide is immobilised as in Example 3, and FRET analysis is conducted as in Example 2.

These polypeptides form stable oligomers in the absence of a glycosylated serine as assessed by FRET.

O-glycosylation of Zip5 occurs upon exposure of this peptide to a source of a protein-modifying enzyme which mediates O-Glycosylation of peptides (e.g. uridine diphospho-N-acetylglucosanine:peptide b N-acetylglucosaminyltransferase) under the appropriate conditions (defined in Haltiwanger et al., 1990, *J. Biol. Chem.*, 265:2563–2568) causes modification of the Ser residue shown in bold and, consequently, the dissociation of these polypeptides and loss of FRET.

EXAMPLE 7

Chymotrypsin Assay

Chymotrypsin is a digestive enzyme found in the small intestine. Peptides based on a heterodimeric coiled coil provide a reporter molecule able to monitor cleavage by chymotrypsin.

Peptide 1 is synthesised by automated peptide synthesis.
IAQLKQKIAQLKQKNAQLKQKI-AQLKQKICQLKQK Peptide 1 (SEQ ID NO. 47)

The cysteine residue, shown in bold, provides a site for attachment of a thiol-directed fluorescent label.

This peptide is capable of binding to the immobilisable partner polypeptide, peptide A:
HHHHHHGGIAQLEQEIAQLEQENAY-LEQEIAQLEQEIAKLEQE Peptide A (SEQ ID NO. 48)

The tyrosine residue (shown here in bold type) is the residue at which chymotrypsin cleaves. The lysine residue (also shown in bold type) provides the site for attachment of thiol-directed fluorescent labels. The 6-His residues are used for immobilisation of the polypeptide as in Example 3.

The circular dichroism (measured in units of ellipticity) of proteins at 222 nm provides a measure of the amount of a-helix present in the structure, with a large, negative ellipticity indicting a high level of helicity. The coiled-coil has a distinctive a-helical CD spectrum with minima at 222 nm and 208 nm (O'Shea et al., 1989, *Science*, 243: 538–542). The CD spectra of the unmodified Peptide A and its chymotrypsin-digested form (Peptide AD) are determined at a sample concentration of 10 μM in 150 mM Kcb, 42.2 mM K$_2$HPO$_4$, 7.8 mM KH$_2$PO$_4$, pH 7.0 at 20° C.; spectra are recorded in a 1 mm pathlength cell in a Jasco J-715 spectropolarimeter with a Jasco PTC-348W Peltier temperature control unit. In all experiments described herein, peptide concentration is determined by tyrosine absorbance at 280 nm in 6M GnHCl. The spectrum of Peptide A which is observed is that of a classic coiled-coil (O'Shea et al., 1989, supra), while that produced by Peptide AD is indicative of random, unfolded polypeptide.

A time-course digestion of Peptide A with chymotrypsin is analysed by MALDI-TOF mass spectrometry. On the protein matrix (MS, denoted SA on each spectrogram) the Peptide A substrate as 4245 Da is evident. It is degraded completely over two hours to a fragment of 2155 Da (which is the N-terminal fragment, cleaved at the Y—H bond). The C-terminal fragment appears to be cleaved at a second site (after L-26) generating a product of 1100 Da, although the final peptide fragment of about 990 Da is not observed in the MS.

Peptides are then labelled using a method adapted from one known in the art (Hermanson, 1996, *Bioconjugate Techniques*, Academic Press). 20 mM fluorescein iodoacetamide (FAM) in DMSO and 0.23 mM peptide in 20 mM TES buffer, pH 7.0 are prepared. These are mixed in a molar ratio of (0.9:1.0, label:peptide) and incubated at 4° C. in the dark for a minimum of 2 hours. Initially, this method is also applied to labelling with rhodamine maleimide at a ratio of (0.9:2.0, label:peptide); however, in other experiments, good labelling has been obtained using rhodamine iodoacetamide at a ratio of (0.9:1.0, label:peptide). Labelling is assessed by reverse phase HPLC (C18 column; solvent A: H$_2$O/0.1% TFA; solvent B: acetonitrile/0.1% TFA) and MALDI-TOF mass spectrometry. Peptide A labelled with fluorescein (Peptide AF) and rhodamine (Peptide AR) are thus generated.

Immobilisation of peptide A on HisSorb supports is based on the specifically engineered 6-Histidine residue tag in peptide A. This tail binds specifically to the Ni-Nitrilotriacetic acid ligand. The Ni-Nitrilotriacetic acid ligand is bound to microtitre plate wells according to manufacturers instructions (see Example 3); 200 μl aliquots of peptides (0.1–100 mM) in a charge phase with Ni$^+$buffer containing 50 mM potassium phosphate, pH 7.2, 150 mM NaCl are added to microtitre plate wells and incubated for 1–2 hours at room temperature. This incubation also works overnight at 4 C. The unbound peptide is removed by washing the microtitre plate wells 4 times with buffer. Excess wash buffer is removed by gently tapping the inverted plates on paper towels.

FRET occurs between fluorophores attached to undigested peptides, which interact with each other, but not between digested peptides, which do not interact (evidenced by loss of structure in CD experiments). Only the fluorescence emission quench of the donor fluorophore is displayed in these experiments.

Fluorescence at 516 nm is measured for labelled Peptide A in a 1 cm pathlength cell at peptide concentrations of 0.08 μM Peptide AF and 0.48 μM Peptide AR in 50 mM kcb, 42.2 mM K$_2$HPO$_4$, 7.8 mM KH$_2$PO$_4$, pH 7.0 at 37° C. in a PTI fluorimeter system with temperature controlled by a waterbath. Upon addition of Peptide AR to Peptide AF, fluorescence in the region of fluorescein emission decreases. This is accompanied by an increase in fluorescence detected in the rhodamine emission region. These data suggest that energy transfer is taking place and that some of the energy emitted by the fluorescein is directly exciting the rhodamine label on the partner peptide. The fluorescence at 516 nm shows no decrease upon addition of Peptide ADR (the digested form of Peptide AR, added at time 500 seconds) to Peptide ADF (the digested form of Peptide AF). In addition, no FRET is observed when Peptide AF is mixed with Peptide ADR, indicating that when even one polypeptide partner is digested, formation of the coiled-coil structure and, hence, protein:protein heterodimerisation (with respect to fluorophore composition), cannot occur.

For in situ immobilised peptide digestion, lyophilised chymotrypsin is dissolved in 1 mM HCl. Polypeptides immobilised as in Example 3 are cleaved by chymotrypsin (1:50 w/w) in 50 mM HEPES, pH 7.0, 10 mM CaCl$_2$, 100 mM NaCl at 37 C for 2 hours. The reaction is monitored as described in Example 3. Addition of chymotrypsin to peptides AF and AR eliminates FRET, as a result of disruption of coiled coil formation.

Together, these results, that FRET does not occur between the digested molecules or between a digested and an undigested molecule, indicated that FRET using labelled, immobilised polypeptides comprising a coiled-coil, may be used successfully in the invention to report on the digestion of polypeptides by proteolytic enzymes.

EXAMPLE 8

Amino- and Carboxypeptidases

Exopeptidases are important in the breakdown of peptides after initial digestion by endopeptidases such as chymotrypsin or trypsin. The end product of attack by such enzymes are free amino acids or dipeptides. An assay for this type of proteolysis relies upon the fluorophores being far from the initial site of proteolysis such that digestion ultimately results in a fragment which is too small to remain within the coiled coil multimer, at which point FRET is lost. An unblocked N-terminus is essential for activity of aminopeptidases.

According to the invention, assays for amino- and carboxypeptidase digestion are set up comprising as the reporter peptides peptides N and C:

```
                                          (SEQ ID NO. 49)
HHHHHHGGIAQLEQEIAQLEQENAQLEQEIAQL   Peptide C (SEQ ID NO. 50)
LEQENAYLEQEIAQLEQEIAKLEQEGGHHHHHH   Peptide N
```

For both peptides, the partner peptide peptide D is used:
IAQLKQKIAQLKQKNAQLKQKI-
AQLKQKICQLKQK Peptide D (SEQ ID NO. 51)

Peptides D, N and C are labelled as set forth in Example 1, at the C and K residues as before.

Substrate peptides are then immobilised on Biacore supports as described in Example 3.

In a first experiment, fluorescein-labelled peptides N and C are assayed for FRET in the presence of rhodamine-labelled peptide D. In both cases, FRET is observed. Addition of carboxypeptidase abolishes FRET for the peptide C-D pair; however, FRET for the peptide N-D pair is not affected.

Addition of aminopeptidase leads to the destabilisation of the peptide N-D pair, and the complete loss of FRET.

EXAMPLE 9

TEV (tobacco etch virus) protease

This protease is important in the processing of the precursor polyprotein of TEV (Mutational analysis of Tobacco Etch Virus polyprotein processing: as and trans proteolytic activities of polyproteins containing the 49-kilodaltonproteinase, Carrington, J. C., Cary, S. M. & Dougherty, W. G., Journal of Virology (1988) 62 2313–2320). In the laboratory it is commonly used in the cleavage of affinity tags from recombinant proteins after the purification process (Release of proteins and peptides from fusion proteins using a recombinant plant virus proteinase, Parks, T. D., Leuther, K. K., Howard, E. D., Johnston, S. A. & Dougherty, W. G., Analytical Biochemistry (1994) 216 413–417). The seven amino acid recognition site allows highly specific cleavage and makes undesirable cleavage of the recombinant protein unlikely.

The peptides used are:
HHHHHHGGIAQLEQEIAQLEQENAY-
LQSEIAQLEQEIAKLEQE Peptide 2 (SEQ ID NO. 52)

The partner peptide is
IAQLKQKIAQLKQKNAQLKQKI-
AQLKQKICQLKQK Peptide 3 (SEQ ID NO. 53)

Peptide 2 is constructed to contain the TEV protease cleavage site, and labelled at an inserted unique lysine residue. Immobilisation is carried out as in Example 3.

The proteolytic reactions are performed as follows:

TEV peptides are immobilised, as described, and cleaved with TEV (1:100 w/w) in 50 mM Tris.HCl (pH 7.0) at 37 C for 2 hours. The TEV activity is assessed by monitoring FRET as in Example 3.

EXAMPLE 10

Thrombin

Thrombin is the final enzyme in the blood clotting cascade, cleaving fibrinogen to fibrin. Its effects are, in part, regulated by a negative feedback mechanism in which thrombin activates protein C which ultimately switches off the cascade and therefore thrombin production. This enzyme is also important in promoting mitosis in fibroblasts, chemotaxis in monocytes and neurite retraction in neurons. A heterodimeric coiled coil is provided to monitor cleavage by thrombin in the manner described above. In order to have cleavage at one site only it is necessary to eliminate all arginine residues other than hat at the intended cleavage site from the peptide (as in Peptide 3 below).

HHHHHHGGIAQLEQEIAQLEQEN-
RQLEQEIAQLEQEIAKLEQE Peptide 3 (SEQ ID NO. 54)

Thrombin cuts between the bold arginine residue (R) and glutamine (Q). The peptide is labelled at the bold lysine residue.

The partner peptide used is peptide 33, labelled at the cysteine shown in bold:
IAQLKQKIAQLKQKNAQLKQKI-
AQLKQKICQLKQK peptide 33 (SEQ ID NO. 55)

Peptides are immobilised as described in Example 3 and cleaved with thrombin (1:50 w/w) in 50 mM Tris.HCl, pH 7.0, 100 mM NaCl, 2.5 mM CaCl$_2$, 0.1% b-mecaptoethanol, at 37 C for 2 hours. The activity of the thrombin is monitored by assessing FRET as in Example 3.

FRET is observed between peptides 3 and 33, labelled with fluorescein and rhodamine respectively, in the absence of thrombin. Incubation with thrombin as above abolishes FRET, due to disruption of the coiled coil and loss of association between the polypeptides.

EXAMPLE 11

Caspases

The caspases (Caspases: enemies within, Thornberry, N. A. & Lazebnik, Y. (1998) Science 281 1312–1316) are a family of proteases with an absolute requirement for cleavage after aspartic acid. They are synthesised as inactive proenzymes and cleaved either autocatalytically or by another member of the family to form an active heterodimer of a large and a small subunit. This family of enzymes play a role in inflammation but, more importantly, several members of the family provide signals triggering apoptosis of the cell and others are directly involved in cell disassembly itself. The role of caspases in the apoptotic process includes the inactivation of proteins protective against apoptosis such as the Bcl-2 proteins, the destruction of proteins with a key role in cell structure such as the lamins and the deregulation of proteins by the disruption of links between regulatory and effector domains. A loss of control of apoptosis leading either to excessive or inadequate cell death plays a role in many disease processes including cancers, neurodegenerative disorders and auto-immune disease. Evidence is already available suggesting that caspase inhibitors are able to protect against inappropriate cell death.

A heterodimeric coiled coil reporter molecule is provided to monitor cleavage by members of the caspase family (e.g. for Caspase 2, 3, 7 below) in the manner described above. The immobilised peptide has the following structure:

HHHHHHGGIAQLEQEIAQLE-
DENDQLEQEIAQLEQEIAKLEQE Peptide 4 (SEQ ID NO. 56)

And the binding partner is:
IAQLKQKIAQLKQKNAQLKQKI-
AQLKQKICQLKQK Peptide 44 (SEQ ID NO. 57)

The procedure of Example 10 is repeated with Peptides 4 and 44, using caspase 2 in place of thrombin, and identical results are obtained.

EXAMPLE 12

Fatty Acylation

As discussed above, the assay format according to the invention can be used to measure post-translational modification events which have proteolysis as an integral step. The molecular basis of these assays is the destabilisation of the binding partnership following the proteolytic event which, if coincident with the covalent addition of another group (farnesylic acid etc.), provides an indirect reporter function for these classes of post-translational modification.

The post-translational modification of proteins with fatty acids includes the attachment of myristic acid to the primary amino group of an N-terminal glycine residue (Milligan, G., Parenti, M., & Magee, A. I. (1995) 'The dynamic role of palmitoylation in signal transduction.' Trends in Biochemical Sciences 20, 181–186), the attachment of palmitic acid to cysteine residues (Milligan et. al. 1995), farnesylic acid attachment to cysteine residues (Cox, A. D. (1995) 'Mutation and analysis of prenylation signal sequences.' Methods in Enzymology 250, 105–121) and the covalent attachment of geranylgeranylic acid to cysteine residues (Cox, A. D. (1995) 'Mutation and analysis of prenylation signal sequences.' Methods in Enzymology 250, 105–121; Shirataki, H., Kaibuchi, K., Hiroyoshi, M., Araki, S., Sasaki, T., & Takai, Y. (1991) 'Inhibition of the action of the stimulatory GDP/GTP exchange protein for smg p21 by the geranylgeranylated synthetic peptides designed from its C-terminal region.' J. Biol. Chem. 266, 20672–20677).

Fatty acylation of proteins is a dynamic post-translational modification which is critical for the biological activity of many proteins, as well as their interactions with other proteins and with membranes. Thus, for a large number of proteins, the location of the protein within a cell can be controlled by its state of prenylation (fatty acid modification) as can its ability to interact with effector enzymes (Ras and MAP kinase, Itoh, T., Kaibuchi, T., Masuda, T., Yamamoto, T., Matsuura, Y., Maeda, A., Shimizu, K., & Takai, Y. (1993) J. Biol. Chem. 268, 3025-; Ras and adenylate cyclase (in yeast) Horiuchi, H., Kaibuchi, K., Kawamura, M., Matsuura, Y., Suzuki, N., Kuroda, Y., Kataoka, T., & Takai, Y. (1992) Mol. Cell. Biol. 12, 4515-) or with regulatory proteins (Shirataki et al., 1991, above). The prenylation status of Ras is important for its oncogenic properties (Cox, 1995, above) thus interference with the prenylation status of Ras is considered a valuable anti-cancer strategy (Hancock, J. F. (1993) Current Biology 3, 770)

An engineered heterodimeric coiled coil is designed to produce a homodimeric reporter molecule capable of monitoring geranylgeranylation. The features are (i) a short coiled-coil structure to achieve a coiled coil oligomer of reasonable stability; (ii) modified C-terminal residues as necessary to comply with the substrate recognition features of the enzyme under study, geranylgeranyl transferase (GG-Tase I).

Immobilised Substrate Polypeptide

```
                                        (SEQ ID NO. 58)
HHHHHHGGIAQLEQEIAQLEQENKQLECIAL         Peptide 5

Binding partner polypeptide
                                        (SEQ ID NO. 59)
IAQLKQKIAQLKQKNACLKQKIA                 Peptide 5a
```

The recognition site is detailed in bold, the underlined cysteine (C) is the site of geranylgeranylation. The concomitant proteolytic removal of the C-terminal residues (IAL) will result in destabilisation of the coiled-coil structure and will prompt dissociation of the oligomer. This can be used as an indirect measure of fatty acylation. A change in the C-terminal amino acid (to Ser, Met, Ala or Gln) alters the specificity of this reporter to measure farnesylation (Protein prenyltransferases, Casey, P. J & Seabra, M. C., Journal of Biological Chemistry (1996) 271 5289–5292).

Labelling for FRET is achieved in two ways: by N-terminal capping and mutation of the existing K to R, thus providing a primary amine to which a fluorophore may be attached, or by incorporation of fluorescent residues during peptide synthesis (see below).

Peptides 5 and 5a are labelled as in Example 1, peptide 5 is immobilised as in Example 3. Association is assayed using FRET under the conditions of Example 2.

Geranylgeranylation is then performed by incubating immobilised peptide 5 with 25 ml rabbit reticulocyte lysate (or the equivalent quantity of either a purified geranylgeranyltransferase or a test sample) and 40 mM geranylgeranyl pyrophosphate in a final volume of at least 50 ml (Cox 1995, above). Peptide 5a is then added at a concentration or 50 mM and the modification of the reporter is followed by observation of acceptor/donor fluorescence emission upon excitation of the donor fluorophore at an appropriate wavelength. A decrease in this ratio indicates a loss of FRET which is a measure of the geranylgeranylation of the reporter.

EXAMPLE 13

Protection of the Reporter from Promiscuous Modification

In order to configure the assays of the invention not only to monitor chemical modification in defined systems, but also to screen for activities in complex environments (e.g. whole cell lysates) it may be necessary to protect the reporter molecule from proteolysis at sites other than those engineered into the structure. The vast majority of naturally occurring enzymes will not recognise as substrates polypeptides comprising D amino acids. The specificity of the reporter group is increased by limiting the use of L amino acids (recognised by enzymes) to residues involved in recognition by the protease. This greatly reduces the probability of unplanned proteolysis at additional sites by other proteases in, for example, a cell extract.

Proteins or peptides composed of D amino acids have a structure which is the exact mirror image of that formed with L amino acids (Identification of D-peptide ligands through mirror image phage display, Schumacher, T. N. M., Mayr, L. M., Minor, D. L. Jnr., Milhollen, M. A., Burgess, M. W., Kim, P. S., Science (1996) 271 1854–1857). We therefore conclude that a coiled coil reporter designed in this way will have a structure of the form shown in the diagram below

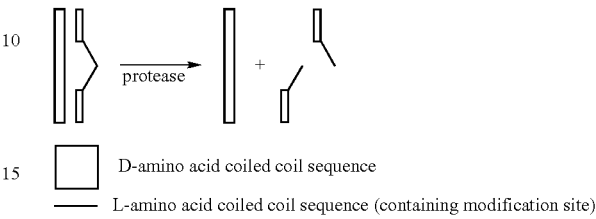

☐ D-amino acid coiled coil sequence

— L-amino acid coiled coil sequence (containing modification site)

---

The invention claimed is:

1. A method for detecting, in a sample, the presence of a modifying enzyme which covalently modifies a polypeptide, the method comprising the steps of:
   a) providing a polypeptide pair comprising a first polypeptide and a second, binding partner polypeptide, capable of associating with said first polypeptide, wherein said second, binding partner polypeptide is not a phospho-specific antibody, and wherein the association of the polypeptides is detectable, and covalent modification of at least one of the polypeptides results in modulation of the association and wherein said covalent modification comprises one of the group consisting of phosphorylation, acylation, glycosylation, ubiquitination, prenylation, sentrinization, and ADP-ribosylation;
   b) providing a modifying group substrate, wherein said substrate, in the presence of a modifying enzyme, results in the covalent modification of said first polypeptide or said second binding partner polypeptide;
   c) immobilizing the first polypeptide to a physical plasmon resonance support;
   d) contacting said immobilized polypeptide and said second binding partner polypeptide in the presence of said sample and said modifying group substrate; and
   e) measuring the association of the second, binding partner polypeptide to the first polypeptide, thereby determining the covalent modification of at least one of said polypeptides, whereby the presence of said modifying enzyme is detected; wherein said association is measured by monitoring the molecular mass of the binding partner by surface plasmon resonance.

2. A method for detecting, in a sample, the presence of a modifying enzyme which covalently modifies a polypeptide, the method comprising the steps of:
   a) providing a polypeptide pair comprising a first polypeptide and a second, binding partner polypeptide, capable of associating with said first polypeptide, wherein said second, binding partner polypeptide is not a phospho-specific antibody, and wherein the association of the polypeptides is detectable, and covalent modification of at least one of the polypeptides results in modulation of the association and wherein said covalent modification comprises one of the group consisting of phosphorylation, acylation, glycosylation, ubiquitination, prenylation, sentrinization, and ADP-ribosylation;
   b) providing a modifying group substrate, wherein said substrate, in the presence of a modifying enzyme, results in the covalent modification of said first polypeptide or said second binding partner polypeptide;

c) immobilizing the first polypeptide to a physical support;

d) contacting said immobilized polypeptide and said second binding partner polypeptide in the presence of said sample and said modifying group substrate; and e) measuring the association of the second, binding partner polypeptide to the first polypeptide, thereby determining the covalent modification of at least one of said polypeptides, whereby the presence of said modifying enzyme is detected; wherein said association is measured by monitoring the molecular mass of the binding partner by scintillation proximity assay.

3. A method for detecting, in a sample, the presence of a modifying enzyme which covalently modifies a polypeptide, the method comprising the steps of:

a) providing a polypeptide pair comprising a first polypeptide and a covalently modified second, binding partner polypeptide capable of associating with said first polypeptide, wherein said second, binding partner polypeptide is not a phospho-specific antibody, and wherein said association of the polypeptides is detectable, and wherein removal of the covalent modification from said second, binding partner polypeptide by a modifying enzyme results in modulation of the association and wherein said covalent modification comprises one of the group consisting of phosphorylation, acylation, glycosylation, ubiquitination, prenylation, sentrinization, and ADP-ribosylation;

b) immobilizing the first polypeptide to a physical plasmon resonance support;

c) contacting said immobilized polypeptide and said second binding partner polypeptide in the presence of said sample; and d) measuring the association of the second, binding partner polypeptide to the first polypeptide, thereby determining the removal of said covalent modification from said second binding partner polypeptide, whereby the presence of said modifying enzyme is detected; wherein said association is measured by monitoring the molecular mass of the binding partner by surface plasmon resonance.

4. A method for detecting, in a sample, the presence of a modifying enzyme which covalently modifies a polypeptide, the method comprising the steps of:

a) providing a polypeptide pair comprising a first polypeptide and a covalently modified second, binding partner polypeptide capable of associating with said first polypeptide, wherein said second, binding partner polypeptide is not a phospho-specific antibody, and wherein said association of the polypeptides is detectable, and wherein removal of the covalent modification from said second, binding partner polypeptide by a modifying enzyme results in modulation of the association and wherein said covalent modification comprises one of the group consisting of phosphorylation, acylation, glycosylation, ubiquitination, prenylation, sentrinization, and ADP-ribosylation;

b) immobilizing the first polypeptide to a physical support;

c) contacting said immobilized polypeptide and said second binding partner polypeptide in the presence of said sample; and d) measuring the association of the second, binding partner polypeptide to the first polypeptide, thereby determining the removal of said covalent modification from said second binding partner polypeptide, whereby the presence of said modifying enzyme is detected; wherein said association is measured by monitoring the molecular mass of the binding partner by scintillation proximity assay.

* * * * *